US008771678B2

(12) United States Patent
Hedrick et al.

(10) Patent No.: US 8,771,678 B2
(45) Date of Patent: *Jul. 8, 2014

(54) METHODS OF USING ADIPOSE TISSUE-DERIVED CELLS IN AUGMENTING AUTOLOGOUS FAT TRANSFER

(75) Inventors: Marc H. Hedrick, Encintias, CA (US); John K. Fraser, San Diego, CA (US)

(73) Assignee: Cytori Therapeutics, Inc., San Diego, CA (US)

( * ) Notice: Subject to any disclaimer, the term of this patent is extended or adjusted under 35 U.S.C. 154(b) by 58 days.

This patent is subject to a terminal disclaimer.

(21) Appl. No.: 13/588,989

(22) Filed: Aug. 17, 2012

(65) Prior Publication Data
US 2012/0308536 A1   Dec. 6, 2012

Related U.S. Application Data

(60) Continuation of application No. 12/694,103, filed on Jan. 26, 2010, now Pat. No. 8,246,947, which is a division of application No. 10/871,503, filed on Jun. 18, 2004, now Pat. No. 7,651,684, which is a continuation-in-part of application No. 10/316,127, filed on Dec. 9, 2002, now abandoned.

(60) Provisional application No. 60/479,418, filed on Jun. 18, 2003, provisional application No. 60/338,856, filed on Dec. 7, 2001.

(51) Int. Cl.
*C12N 5/00* (2006.01)

(52) U.S. Cl.
USPC .............. 424/93.7; 435/366; 606/1; 606/131; 604/19; 604/22

(58) Field of Classification Search
None
See application file for complete search history.

(56) References Cited

U.S. PATENT DOCUMENTS

| | | |
|---|---|---|
| 4,000,275 A | 12/1976 | Lunn |
| 4,418,691 A | 12/1983 | Yannas et al. |
| 4,458,678 A | 7/1984 | Yannas et al. |
| 4,734,269 A | 3/1988 | Clarke et al. |
| 4,820,626 A | 4/1989 | Williams et al. |
| 4,834,703 A | 5/1989 | Dubrul et al. |
| 4,883,755 A | 11/1989 | Carabasi et al. |
| 4,897,185 A | 1/1990 | Schuyler et al. |
| 4,963,489 A | 10/1990 | Naughton et al. |
| 5,034,135 A | 7/1991 | Fischel |
| 5,035,708 A | 7/1991 | Alchas et al. |
| 5,079,160 A | 1/1992 | Lacy et al. |
| 5,087,244 A | 2/1992 | Wolinsky et al. |
| 5,092,883 A | 3/1992 | Eppley et al. |
| 5,131,907 A | 7/1992 | Williams et al. |
| 5,143,063 A | 9/1992 | Fellner |
| 5,158,867 A | 10/1992 | McNally et al. |
| 5,226,914 A | 7/1993 | Caplan et al. |
| 5,234,608 A | 8/1993 | Duff |
| 5,261,612 A | 11/1993 | Ftaiha |
| 5,312,380 A | 5/1994 | Alchas et al. |
| 5,372,945 A | 12/1994 | Alchas et al. |
| 5,409,833 A | 4/1995 | Hu et al. |
| 5,436,135 A | 7/1995 | Tayot et al. |
| 5,470,307 A | 11/1995 | Lindall |
| 5,486,359 A | 1/1996 | Caplan et al. |
| 5,521,087 A | 5/1996 | Lee et al. |
| 5,562,646 A | 10/1996 | Goldman et al. |
| 5,591,625 A | 1/1997 | Gerson et al. |
| 5,641,622 A | 6/1997 | Lake et al. |
| 5,653,689 A | 8/1997 | Buelna et al. |
| 5,654,186 A | 8/1997 | Cerami et al. |
| 5,686,262 A | 11/1997 | Fink et al. |
| 5,686,289 A | 11/1997 | Humes et al. |
| 5,688,531 A | 11/1997 | Benayahu |
| 5,713,860 A | 2/1998 | Kaplan et al. |
| 5,728,739 A | 3/1998 | Ailhaud et al. |
| 5,736,396 A | 4/1998 | Bruder et al. |
| 5,744,360 A | 4/1998 | Hu et al. |
| 5,783,408 A | 7/1998 | Hamilton et al. |
| 5,785,965 A | 7/1998 | Pratt et al. |
| 5,786,207 A | 7/1998 | Katz et al. |
| 5,811,094 A | 9/1998 | Caplan et al. |

(Continued)

FOREIGN PATENT DOCUMENTS

| | | |
|---|---|---|
| CN | 1287166 A | 3/2001 |
| EP | 0 399 340 | 11/1990 |

(Continued)

OTHER PUBLICATIONS

Abbate, A., Biondi-Zoccai, G.G. and Baldi, A. (2002) "Pathophysiologic role of myocardial apoptosis in post-infarction left ventricular remodeling" J Cell Physiol 193, 145-53.

Aharinejad, S., Mars, S.C., Jr., Bock P., Mason-Savas, A., MacKay, C.A. Larson, E.K., Jackson, M.E., Luftensteiner, M. and Weisbauer, E. (1995) "CSF-1 treatment promotes angiogenesis in the metaphysics of osteopetrotic (toothless, tl) rats" Bone 16, 315-324.

Ahrens, Patricia Buckley et al., "Stage-Related Capacity for Limb Chondrogenesis in Cell Culture," *Developmental Biology*, 1977, 60:69-82.

Ailhaud, et al., 1983, "Hormonal requirements for growth and differentiation of OB17 preadipocyte cells in vitro," *Diabete & Metabolisme*, vol. 9:125-133.

Ailhaud, et al., 1985, "Lipoprotiene lipase et differenciation adipocytaire," *Reprod. Nutr. Develop.*, vol. 25:153-158.

Alameddine, Hala S. et al., "Regeneration of Skeletal Muscle Fibers from Autologous Satellite Cells Multiplied In Vitro. An Experimental Model for Testing Cultured Cell Myogenicity,"*Muscle & Nerve*, 1989, 12:544-55.

(Continued)

*Primary Examiner* — Blaine Lankford
(74) *Attorney, Agent, or Firm* — Knobbe Martens Olson & Bear LLP

(57) ABSTRACT

Methods of treating patients for conditions such as breast augmentation, soft tissue defects, and urinary incontinence, are described. The methods include removing adipose tissue from a patient, processing a portion of the adipose tissue to obtain a substantially isolated population of cells comprising disaggregated adipose-derived stem cells, mixing the concentrated population of adipose-derived cells comprising disaggregated adipose-derived cells with a portion of unprocessed, intact, non-disaggregated adipose tissue to form a composition, and administering the composition to the patient from which the adipose tissue was removed.

14 Claims, 21 Drawing Sheets

(56) References Cited

U.S. PATENT DOCUMENTS

| | | |
|---|---|---|
| 5,817,050 A | 10/1998 | Klein |
| 5,827,735 A | 10/1998 | Young et al. |
| 5,827,740 A | 10/1998 | Pittenger |
| 5,827,897 A | 10/1998 | Ailhaud et al. |
| 5,830,714 A | 11/1998 | Swaminathan et al. |
| 5,830,741 A | 11/1998 | Dwulet et al. |
| 5,837,235 A | 11/1998 | Mueller et al. |
| 5,837,444 A | 11/1998 | Shah et al. |
| 5,837,539 A | 11/1998 | Caplan et al. |
| 5,851,832 A | 12/1998 | Weiss et al. |
| 5,854,292 A | 12/1998 | Ailhaud et al. |
| 5,869,037 A | 2/1999 | Crystal et al. |
| 5,906,934 A | 5/1999 | Grande et al. |
| 5,908,784 A | 6/1999 | Johnstone et al. |
| 5,916,743 A | 6/1999 | Lake et al. |
| 5,952,215 A | 9/1999 | Dwulet et al. |
| 5,968,356 A | 10/1999 | Morsiani |
| 5,980,887 A | 11/1999 | Isner et al. |
| 6,001,642 A | 12/1999 | Tsao |
| 6,010,696 A | 1/2000 | Caplan et al. |
| 6,020,196 A | 2/2000 | Hu et al. |
| 6,030,836 A | 2/2000 | Thiede et al. |
| 6,043,066 A | 3/2000 | Mangano et al. |
| 6,086,582 A | 7/2000 | Altman et al. |
| 6,090,121 A | 7/2000 | Weber et al. |
| 6,139,757 A | 10/2000 | Ohmura |
| 6,197,325 B1 | 3/2001 | MacPhee et al. |
| 6,200,606 B1 | 3/2001 | Peterson et al. |
| 6,206,873 B1 | 3/2001 | Paolini et al. |
| 6,221,315 B1 | 4/2001 | Giesler et al. |
| 6,238,908 B1 | 5/2001 | Armstrong et al. |
| 6,251,295 B1 | 6/2001 | Johnson |
| 6,261,549 B1 | 7/2001 | Fernandez et al. |
| 6,277,060 B1 | 8/2001 | Neumann |
| 6,316,247 B1 | 11/2001 | Katz et al. |
| 6,322,784 B1 | 11/2001 | Pittenger et al. |
| 6,355,239 B1 | 3/2002 | Bruder et al. |
| 6,368,356 B1 | 4/2002 | Zhong et al. |
| 6,387,369 B1 | 5/2002 | Pittenger et al. |
| 6,429,013 B1 | 8/2002 | Halvorsen et al. |
| 6,436,639 B1 | 8/2002 | Kiefer et al. |
| 6,451,207 B1 | 9/2002 | Sterman et al. |
| 6,475,764 B1 | 11/2002 | Burtscher et al. |
| 6,517,526 B1 | 2/2003 | Tamari |
| 6,576,464 B2 | 6/2003 | Gold et al. |
| 6,589,728 B2 | 7/2003 | Csete et al. |
| 6,623,959 B2 | 9/2003 | Harris |
| 6,689,352 B2 | 2/2004 | Achen et al. |
| 6,777,231 B1 | 8/2004 | Katz et al. |
| 6,804,558 B2 | 10/2004 | Haller et al. |
| 7,078,230 B2 | 7/2006 | Wilkison |
| 7,390,484 B2 | 6/2008 | Fraser et al. |
| 7,514,075 B2 | 4/2009 | Hedrick et al. |
| 7,585,670 B2 | 9/2009 | Hedrick et al. |
| 7,651,684 B2 * | 1/2010 | Hedrick et al. ............ 424/93.7 |
| 7,767,452 B2 | 8/2010 | Kleinsek |
| 7,771,716 B2 | 8/2010 | Hedrick et al. |
| 7,887,795 B2 | 2/2011 | Fraser et al. |
| 7,901,672 B2 | 3/2011 | Fraser et al. |
| 8,053,248 B2 | 11/2011 | Bakaltcheva et al. |
| 8,105,580 B2 | 1/2012 | Fraser et al. |
| 8,119,121 B2 | 2/2012 | Fraser et al. |
| 8,163,276 B2 | 4/2012 | Hedrick et al. |
| 8,246,947 B2 * | 8/2012 | Hedrick et al. ............ 424/93.7 |
| 8,404,229 B2 | 3/2013 | Fraser et al. |
| 2001/0000802 A1 | 5/2001 | Soykan et al. |
| 2001/0009757 A1 | 7/2001 | Bischof et al. |
| 2002/0103542 A1 | 8/2002 | Bilbo |
| 2002/0111694 A1 | 8/2002 | Ellingsen et al. |
| 2002/0182211 A1 | 12/2002 | Peach et al. |
| 2003/0014126 A1 | 1/2003 | Patel et al. |
| 2003/0026759 A1 | 2/2003 | Ferrell et al. |
| 2003/0054331 A1 | 3/2003 | Fraser et al. |
| 2003/0069168 A1 | 4/2003 | Xu et al. |
| 2003/0075516 A1 | 4/2003 | Rothman et al. |
| 2003/0082152 A1 | 5/2003 | Hedrick et al. |
| 2003/0100105 A1 | 5/2003 | Poo et al. |
| 2003/0152558 A1 | 8/2003 | Luft et al. |
| 2003/0161816 A1 | 8/2003 | Fraser et al. |
| 2003/0161817 A1 | 8/2003 | Young et al. |
| 2003/0162707 A1 | 8/2003 | Fraser et al. |
| 2003/0211085 A1 | 11/2003 | Sanberg et al. |
| 2003/0211602 A1 | 11/2003 | Atala |
| 2003/0212024 A1 | 11/2003 | Keating et al. |
| 2004/0067218 A1 | 4/2004 | Casteilla et al. |
| 2004/0197304 A1 | 10/2004 | Chen et al. |
| 2005/0008626 A1 | 1/2005 | Fraser et al. |
| 2005/0084961 A1 | 4/2005 | Hedrick et al. |
| 2005/0271636 A1 | 12/2005 | Oliver et al. |
| 2006/0025338 A1 | 2/2006 | Alitalo et al. |
| 2006/0088532 A1 | 4/2006 | Alitalo et al. |
| 2007/0111935 A1 | 5/2007 | Franco et al. |
| 2007/0116674 A1 | 5/2007 | Casteilla et al. |
| 2007/0148766 A1 | 6/2007 | Yoshimura et al. |
| 2007/0212676 A1 | 9/2007 | Takakura et al. |
| 2007/0233038 A1 | 10/2007 | Pruitt et al. |
| 2007/0274960 A1 | 11/2007 | Harman et al. |
| 2008/0206208 A1 | 8/2008 | Casteilla et al. |
| 2009/0104159 A1 | 4/2009 | Prosper et al. |
| 2010/0015104 A1 | 1/2010 | Fraser et al. |
| 2013/0060338 A1 | 3/2013 | Hedrick et al. |
| 2013/0108592 A1 | 5/2013 | Pinkernell et al. |
| 2013/0121974 A1 | 5/2013 | Fraser et al. |

FOREIGN PATENT DOCUMENTS

| | | |
|---|---|---|
| EP | 0 418 979 | 3/1991 |
| EP | 0 446 450 | 9/1991 |
| EP | 0 448 770 | 10/1991 |
| EP | 0 512 769 | 11/1992 |
| EP | 0 515 726 | 12/1992 |
| EP | 0 570 331 | 11/1993 |
| EP | 0 987 325 | 3/2000 |
| EP | 1 077 254 | 2/2001 |
| EP | 1 011 752 | 10/2004 |
| EP | 1 712 616 | 10/2006 |
| EP | 1 678 295 | 3/2013 |
| JP | 59-090649 | 5/1984 |
| JP | 01-141583 | 6/1989 |
| JP | 02-002884 | 1/1990 |
| JP | 02-295484 | 12/1990 |
| JP | 04-183381 | 6/1992 |
| JP | 04-267873 | 9/1992 |
| JP | 7-255469 | 10/1995 |
| JP | 08-208401 | 8/1996 |
| JP | 08-259604 | 10/1996 |
| JP | 9-255588 | 9/1997 |
| JP | 10-17310 | 1/1998 |
| JP | 11-4682 | 1/1999 |
| JP | 11-57731 | 3/1999 |
| JP | 2000-325068 | 11/2000 |
| JP | 2003-024040 | 1/2003 |
| JP | 2001-231539 | 8/2003 |
| JP | 2004-99471 | 4/2004 |
| JP | 2004-272762 | 9/2004 |
| KR | 10-2004-0063167 | 7/2004 |
| WO | WO 86/01111 | 2/1986 |
| WO | WO 87/03812 | 7/1987 |
| WO | WO 94/02156 | 2/1994 |
| WO | WO 94/03645 | 2/1994 |
| WO | WO 94/27698 | 12/1994 |
| WO | WO 96/38482 | 12/1996 |
| WO | WO 97/18299 | 5/1997 |
| WO | WO 97/26326 | 7/1997 |
| WO | WO 97/39104 | 10/1997 |
| WO | WO 97/40137 | 10/1997 |
| WO | WO 97/41208 | 11/1997 |
| WO | WO 97/49827 | 12/1997 |
| WO | WO 98/04682 | 2/1998 |
| WO | WO 98/20731 | 5/1998 |
| WO | WO 98/32333 | 7/1998 |
| WO | WO 98/51317 | 11/1998 |
| WO | WO 99/01145 | 1/1999 |
| WO | WO 99/02654 | 1/1999 |

(56) References Cited

FOREIGN PATENT DOCUMENTS

| | | |
|---|---|---|
| WO | WO 99/03973 | 1/1999 |
| WO | WO 99/11789 | 3/1999 |
| WO | WO 99/28444 | 6/1999 |
| WO | WO 00/53795 | 9/2000 |
| WO | WO 01/21767 | 3/2001 |
| WO | WO 01/62901 | 8/2001 |
| WO | WO 02/055678 | 7/2002 |
| WO | WO 02/064157 | 8/2002 |
| WO | WO 02/068010 | 9/2002 |
| WO | WO 02/075302 | 9/2002 |
| WO | WO 02/081007 | 10/2002 |
| WO | WO 03/001329 | 1/2003 |
| WO | WO 03/022988 | 3/2003 |
| WO | WO 03/024215 | 3/2003 |
| WO | WO 03/039481 | 5/2003 |
| WO | WO 03/053346 | 7/2003 |
| WO | WO 03/053362 | 7/2003 |
| WO | WO 03/073998 | 9/2003 |
| WO | WO 03/080801 | 10/2003 |
| WO | WO 2004/013275 | 2/2004 |
| WO | WO 2004/029230 | 4/2004 |
| WO | WO 2004/052418 | 6/2004 |
| WO | WO 2004/072828 | 8/2004 |
| WO | WO 2004/074457 | 9/2004 |
| WO | WO 2004/093934 | 11/2004 |
| WO | WO 2004/101015 | 11/2004 |
| WO | WO 2005/012480 | 2/2005 |
| WO | WO 2005/025584 | 3/2005 |
| WO | WO 2005/034843 | 4/2005 |
| WO | WO 2005/035738 | 4/2005 |
| WO | WO 2005/063967 | 7/2005 |
| WO | WO 2006/014156 | 2/2006 |
| WO | WO 2005/035742 | 4/2007 |
| WO | WO 2007/135284 | 11/2007 |
| WO | WO 2009/076548 | 6/2009 |

OTHER PUBLICATIONS

Alhadlaq et al. "Engineered adipose tissue from human mesenchymal stem cells maintains predefined shape and dimension: implications in soft tissue augmentation and reconstruction." Tissue Eng 11, 556-566 (2005).

Angele, P. et al., "Engineering of Osteochondral Tissue with Bone Marrow Mesenchymal Progenitor Cells in a Derivatized Hyaluronan-Gelatin Composite Sponge," Tissue Engineering, 1999, 5:545-53.

Ankrom et al., 1998, Age-related changes in human oestrogen receptor function and levels in osteoblasts, Biochem J. 333:787-794.

Aragona, F. L. D'Urso et al (1998) "Immunologic aspects of bovine injectable collagen in humans. A review" Eur Urol 33(2): 129-33.

Arvidsson, A., Collin, T., Kirik, D., Kokaia, Z., and Lindvall, O. (2002) "Neuronal replacement from endogenous precursors in the adult brain after stroke" Nat Med 8, 963-70.

Ashjian et al., 2003, In vitro differentiation of human processed lipoaspirate cells into early neural progenitors Plast Reconstr Surg 111 1922-1931.

Asken, S. (1990) "Microliposuction and autologous fat transplantation for aesthetic enhancement of the aging face" J Dermatol Surg Oncol 16(10): 965-72.

Aso et al., Aug. 15, 1995, A Preadipocyte Clonal Line from bovine Intramuscular Adipose Tissue: Nonexpression of GLUT-4 protein during Adipocyte Differentiation, Biochem. Biophys. Res. Commun. 213:369-375.

Asou, Y., Riffling, S.R., Yoshitake, H., Tsuji, K., Shinomiya, K., Nifuji, A., Denhardt, D.T., and Noda, M. (2001) "Osteopontin facilitates angiogenesis, accumulation of osteoclasts, and resorption in ectopic bone" Endocrinology 142, 1325-1332.

Assady, S., Maor, G., Amit, M., Itskovitz-Eldor, J., Skorecki, K.L., and Tzukerman, M. (2001) "Insulin production by human embryonic stem cells" Diabetes 50, 1691-7.

Assmus et al., 2002, Transplantation of Progenitor Cells and Regeneration Enhancement in Acute Myocardial Infarction (TOPCARE-AMI) Circulation 106, pp. 3009-3017.

Athanasopoulos, T., Fabb, S., and Dickson, G. (2000) "Gene therapy vectors based on adeno-associated virus: characteristics and applications to acquired and inherited diseases (review)" Int J Mol Med 6, 363-75.

ATTC Preservation Methods: Freezing and Free-Drying, ATCC, 2nd Edition, 1991.

Avital, I., D. Inderbitzin, et al. (2001) "Isolation, characterization and transplantation of bone marrow-derived hepatocyte stem cells" Biochem Biophys Res Commun 288(1): 156-64.

Badiavas, et al. "Participation of bone marrow derived cells in cutaneous would healing." Journal of Cellular Physiology. 196(2): 245-250 (2003).

Bagnato et al., Jan. 2002, Emerging role of endothelin-1 in tumor angiogenesis, Trends in Endocrinology and Metabolism, 14(1):44-50.

Bailey, A. J. et al., "Age-Related Changes in the Biochemical Properties of Human Cancellous Bone Collagen: Relationship to Bone Strength," Calcified Tissue International, 1999, 65:203-10.

Banfi, A., Bianchi, G., Galotto, M., Cancedda, R., and Quarto, R. (2001) "Bone marrow stromal damage after chemo/radiotherapy: occurrence, consequences and possibilities of treatment" Leuk Lymphoma 42, 863-70.

Barghorn, A. et al., "a-Smooth Muscle Actin Distribution in the Pulmonary Vasculature Comparing Hypoplastic and Normal Fetal Lungs," Pediatric Pathology & Laboratory Medicine, 1998, 18:5-22.

Barker et al., 2001, Survival after transplantation of unrelated donor umbilical cord blood is comparable to that of huan leukocyte antigen-matched unrelated donor bone marrow: results of a matched-pair analysis, Blood, 97:2957-61.

Barry, F.P., Boynton, R.E., Haynesworth, S., Murphy, J.M., and Zaia, J. (1999) "The monoclonal antibody SH-2, raised against human mesenchymal stem cells, recognizes an epitope on endoglin (CD105)" Biochem Biophys Res Commun 265, 134-9.

Bartynski, J.M., S. Marion et al. (1990) "Histopathologic evaluation of adipose autografts in a rabit ear model" Otolaryngol Hea Neck Surg 102(4): 314-21.

Bastard, J. P. et al., "A Mini-Liposuction Technique Adapted to the Study of Human Adipocyte Glucose Transport System," Diabetologia, 36(Suppl. 1):A135, 1993.

Baylink, David J., "Glucocorticoid-Induced Osteoporosis," The New England Journal of Medicine, 1983, 309:306-8.

Becerra, José et al., "Demineralized Bone Matrix Mediates Differentiation of Bone Marrow Stromal Cells In Vitro: Effect of Age of Cell Donor," Journal of Bone and Mineral Research, 1996, 11:1703-14.

Beecken, W.D., Kramer, W., and Jonas, D. (2000) "New molecular mediators in tumor angiogenesis" J Cell Mol Med 4, 262-269.

Beiser, Ian H. and Irvin O. Kanat, "Subchondral Bone Drilling: A Treatment for Cartilage Defects," Journal of Foot Surgery, 1990, 29:595-601.

Bennett, JH, et al., 1991 J. Cell Sci. "Adipocytic cells cultured from marrow have osteogenic potential," 99(Pt1):131-139.

Berdel et al., 1982, Purification of human monocytes by adherence to polymeric fluorocarbon. Characterization of the monocyte-enriched cell fraction, Immunobiology, 163:511-520.

Beresford, et al., 1986 Endo. "1,25-Dihydroxyvitamin D3 and Human Bone-Derived Cells in Vitro: Effects on Alkaline Phosphatase, Type I Collagen and Proliferation," 119:1776-1785.

Bergeon, M.T. (1967) "Collagen: a review" J Okla State Med Assoc 60(6): 330-2.

Bernlohr, David A. et al., "Tissue Specific Expression of p422 protein, A putative Lipid Carrier, In Mouse Adipocytes," Biochem. Biophys. Res. Comun. 1985 132:850-855.

Bianco et al., Apr. 2008, Mesenchymal stem cells: revisiting history, concepts, and assays, Cell Stem Cell, 2:313-319.

Bickenbach, J.R. and Dunnwald, M. (2000) "Epidermal stem cells: characteristics and use in tissue engineering and gene therapy" Adv Dermatol 16, 159-83.

Bjornson, et al., 1999 Science "Turning Brain into Blood: A Hematopoetic Fate Adopted by Adult Neural Stem Cells in Vivo," 283:534-537.

(56) References Cited

OTHER PUBLICATIONS

Björntrop, et al. "Isolation and characterization of cells from rat adipose tissue developing into adipocytes." J. Lipid Res. 19:316-324 (1978).
Black et al., 2000, Adult Rat and Human Bone Marrow Stromal cells Differentiate Into Neurons, *J. Neurosci. Res. Science* 61:364-370.
Block, C.A., C.S. Cooper (2003) "Long-term Efficacy of periurethral collagen injection for the treatment of urinary incontinence secondary to myelomeningocele" J Urol 169(1): 327-329.
Boering, G. and A.J. Huffstadt (1967) "The use of derma-fat grafts in the face" Br J Plast Surg 20(2): 172-8.
Boerner, C.F. (1988) "Allergic response to a porcine collagen corneal shield. Case report" Arch Opthalmol 106(2): 171.
Bond et al., 1999, "Human Subcutaneouspreadipocytes Differentiate Into osteoblasts," *FASEB Journal* 13:600A.
Bonner-Weir, S. and Sharma, A. (2002) "Pancreatic stem cells" J Pathol 197, 519-526.
Boskey, et al., 1985, "The Effect of Osteocalcin on In Vitro Lipid-Induced Hydroxyapatite Formation and Seeded Hydroxyapatite Growth," *Calc. Tiss. Int.* 37:75.
Breen, Ellen C. et al., "TGFb Alters Growth and Differentiation Related Gene Expression in Proliferating Osteoblasts In Vitro, Preventing Development of the Mature Bone Phenotype," *Journal of Cellular Physiology*, 1994, 160:323-35.
Bruder, et al., 1997 J. Cell Biochem. "Growth Kinetics, Self-Renewal, and the Osteogenic Potential of Purified Human Mesenchymal Stem Cells During Extensive Subcultivation and Following Cryopreservation," 64:278-294.
Bruder, Scott P. et al., "Bone Regeneration by Implantation of Purified, Culture-Expanded Human Mesenchymal Stem Cells," *Journal of Orthopaedic Research*, 1998, 16:155-62.
Bulleid, J.J., D.C. John et al (2000) "Recombinant expression systems for the production of collagen" Biochem Soc Trans 28(4): 350-3.
Burres, S. (2001) "Soft-tissue augmentation with fascian" Clin Plast Surg 28(1): 101-10.
Buschmann, I.R. Busch, H.J., Mies, G., and Hossmann, K.A. (2003) "Therapeutic induction of arteriogenesis in hypoperfused rat brain via granulocyte-macrophage colony-stimulating factor" Circulation 108, 610-615.
Butler-Browne, et al., 1990 *Anat. Embryol.* (*Berl*) "Myosin heavy and light chain expression during human skeletal muscle development and precocious muscle maturation induced by thyroid hormone," 181:513-522.
Butnariu-Ephrat, Miriam et al., "Resurfacing of Goat Articular Cartilage by Chondrocytes Derived From Bone Marrow," *Clinical Orthopaedics and Related Research*, 1996, 330:234-43.
Campion, Dennis R., "The Muscle Satellite Cell: A Review," *Internationals Review of Cytology*, 1984, 87:225-51.
Caplan, A.I. and Bruder, S.P. (2001) "Mesenchymal stem cells: building blocks for molecular medicine in the 21st century" Trends Mol Med 7, 259-64.
Caplan, Arnold I., "Mesenchymal Stem Cells," *Journal of Orthopaedic Research*, 1991, 9:641-50.
Caplan, Arnold I., "The Mesengenic Process," *Clinics in Plastic Surgery*, 21:429-35, 1994.
Carano, R.A. and Filvaroff, E.H. (2003) "Angiogenesis and bone repair" Drug Discov. Today 8, 980-989.
Carmeliet, P. (2000) "Mechamisms of angiogenesis and arteriogenesis" Nat Med 6, 389-395.
Carmeliet, P. and A. Luttun (2001) "The emerging role of the bone marrow-derived stem cells in (therapeutic angiogenesis)" Thromb Haemost 86(1): 289-97.
Carpandena, C.A. "Collagen alterations in adipose autograft's." Aesthetic Plastic Surgery vol. 18, 11-15 (1994).
Carranza-Bencano, A. et al., "Comparative Study of the Reconstruction of Articular Cartilage Defects with Free Costal Perichondrial Grafts and Free Tibial Periosteal Grafts: An Experimental Study on Rabbits," *Calcified Tissue International*, 1999, 65:402-7.

Casteilla et al., Apr. 26, 2011, Adipose-derived stromal cells: their identity and uses in clinical trials, an update, World J. Stem Cells, 3(4):25-33.
Castro, et al. "Failure of Bone Marrow Cells to Transdifferentiate into Neural Cells in Vivo." Science. 297:1299 (2002).
Castro, et al. "Response to Comment on 'Failure of Bone Marrow Cells to Transdifferentiate into Neural Cells in Vivo'." Science. 299:1184c (2003).
Castro-Malaspina, H., W. Ebell, et al. (1984) "Human bone marrow fibroblast colony-forming units (CFU-F" Prog Clin Ciol Res 154: 209-36.
Cheifetz et al., 1988, Analysis of intracellular osteopontin as a marker of osteoblastic cell differentiation and mesenchymal cell migration, European Journal of Oral Sciences, 106(Supp. 1):401-7.
Cheifetz, S. et al., "Endoglin is a Component of the Transforming Growth Factor-β Receptor System in Human Endothelial Cells," *J. Biol. Chem.*, 1992 267:19027-19030.
Chen, J. et al. Intravenous Administration of Human Bone Marrow Stromal Cells Induces Angiogenesis in the Ischemic Boundary Zone After Stroke in Rats, Circulation Research, Apr. 2003, vol. 92, pp. 692-699.
Chen, J. et al. Intravenous Bone Marrow Stromal Cell Therapy Reduces Apoptosis and Promotes Endogenous Cell Proliferation After Stroke in Femal Rat, J. Neuroscience Research, Sep. 2003, vol. 73 pp. 778-786.
Chen, Theresa L. et al., "1α,25-Dihydroxyvitamin D3 Receptors in Cultured Rat osteoblast-like Cells," J. Biol. Chem. 1983 258:4350-4355.
Chen, Xiaoli et al., "Differentiation-dependent expression of obese (ob) gene by preadipocytes and adipocytes in primary cultures of porcine stromal-vascular cells," *Biochimica et Biophysica Acta*, 1997, 1359:136-42.
Cheng S-L., et al., 1994 *Endo* "Differentiation of Human Bone Marrow Osteogenic Stromal Cells in Vitro: Induction of the Osteoblast Phenotype by Dexamethasone," 134: 277-286.
Chimal-Monroy et al., 1999, Expression of N-cadherin, N-CAM, fibronectin tenascin is stimulated by TGF-b1, b2, b3 and b5 during the formation of precartilage condensations, *The International Journal of Developmental Biology*, 43:59-67.
Cho,S.W. et al. "Engineering of volume-stable adipose tissues." *Biomaterials* 26, 3577-3585 (2005).
Cho,S.W. et al. "Enhancement of adipose tissue formation by implantation of adipogenic-differentiated preadipocytes." *Biochem Biophys Res Commun* 345, 588-594 (2006).
Choi et al. "Adipose tissue engineering using mesenchymal stem cells attached to injectable PLGA spheres." *Biomaterials* 26, 5855-5863 (2005).
Choi,Y.S. et al. "Adipogenic differentiation of adipose tissue derived adult stem cells in nude mouse." *Biochem Biophys Res Commun* 345, 631-637 (2006).
Chyun, et al., 1984 *Endo*. "Cortisol Decreases Bone Formation by Inhibiting Periosteal Cell Proliferation," 114:477-480.
Civin, C.I., Strauss, L.C., Fackler, M.J., Trischmann, T.M., Wiley, J.M., and Loken, M.R. (1990) "Positive stem cell selection-basic science" Prog Clin Biol Res 333, 387-401.
Clarke, D. and Frisen, J. (2001) "Differentiation potential of adult stem cells" Curr Opin Genet Dev 11, 575-80.
Clavijo-Alvarez,J.A. et al. "A novel perfluoroelastomer seeded with adipose-derived stem cells for soft-tissue repair." *Plast Reconstr Surg* 118, 1132-1142 (2006).
Coleman III, et al. "Autologous Collagen? Lipocytic Dermal Augmentation. A Histopathologic Study". J. Dermatol Surg Oncol. vol. 19, 1032-1040 (1993).
Coleman, S.R. (1995) "Long-term survival of fat transplants: controlled demonstrations" Aesthetic Plast Surg 19(5): 421-5.
Coleman, S.R. (2001). "Structural fat grafts: the ideal filler?" Clin Plast Surg 28(1): 111-9.
Coleman, W.P., 3rd (1991) "Autologous fat transplantation" Plast Reconstr Surg 88(4): 736.
Commons, G.W., Halperin, B., and Chang, C.C. (2001) "Large-volume liposuction: a review of 631 consecutive cases over 12 years" Plast Reconstr Surg 108, 1753-63.

(56) References Cited

OTHER PUBLICATIONS

Conget, PA and JJ Minguell 1999 *J. Cell. Physiol* "Phenotypical and Functional Properties of Human Bone Marrow Mesenchymal Progenitor Cells," 181:67-73.

Connolly, J.F. (1998) "Clinical use of marrow osteoprogenitor cells to stimulate osteogenesis" Clin Orthop(355 Suppl): S257-66.

Considine, et al., "Paracrine stimulation of preadipocyte-enriched cell cultures by mature adipocytes," *American Journal of Physiology* 1996 270(5) E895-E899.

Cooper, et al., 1999 *J. Endocrinol*. "Glucocorticoid activity, inactivity and the osteoblast," 163: 159-164.

Crandall, David L. et al., "Identification of Estrogen Receptor b RNA in Human Breast and Abdominal Subcutaneous Adipose Tissue," *Biochemical and Biophysical Research Communications*, 248:523-6, 1998.

Crevensten et al. "Intervertebral Disc Cell Therapy for Regeneration: Mesenchymal Stem Cell Implantation in Rat Intervertebral Discs." Annals of Biomedical Engineering. 32(3):430-434 (2004).

Cronin, K.J. et al. "New murine model of spontaneous autologous tissue engineering, combining an arteriovenous pedicle with matrix materials." *Plast Reconstr Surg* 113, 260-269 (2004).

Dani, et al., "Differentiation of embryonic stem cells into adipocytes in vitro," *J. Cell Sci*. 1997 110, 1279-1285.

Davis, P.F. and Z.M. Mackie (1981) "A simple procedure for the separation of insoluble collagen and elastin" Anal Biochem 115(1): 11-7.

De Ugarte et al., 2003, Future of fat as raw material for tissue regeneration, Ann Plast Surg 50, 215-9.

Deng, Weiwen et al., "In Vitro Differentiation of Human Marrow Stromal Cells into Early Progenitors of Neural Cells by Conditions That Increase Intracellular Cyclic AMP," *Biochemical and Biophysical Research Communications*, 2001, 282:148-52.

Dengler T et al. 2002. Stem Cell Therapy for the Infarcted Heart ("Cellular Cardiomyoplasty"), Herz 27:598-610.

Denker, A.E., et al., 1995 *Differentiation* "Formation of cartilage-like spheroids by micromass cultures of murine C3H10l/2 cells upon treatment with transforming growth factor-b1," 59: 25-34.

Denker, et al., 1999 *Differentiation* "Chondrogenic differentiation of murine C3H10T1/2 multipotential mesenchymal cells: I. Stimulation by bone morphogenetic protein-2 in high-density micromass cultures," 64:67-76.

Dennis, James E. et al., "A Quadripotential Mesenchymal Progenitor Cell Isolated from the Marrow of an Adult Mouse," *Journal of Bone and Mineral Research*, 1999, 14:700-9.

Dias, Peter et al., "The Molecular Basis of Skeletal Muscle Differentiation," *Seminars in Diagnostic Pathology*, 1994, 11:3-14.

Diefenderfer, David L. and Carl T. Brighton, "Microvascular Pericytes Express Aggrecan Message Which is Regulated by BMP-2," *Biochemical and Biophysical Research Communications*, 2000, 269:172-8.

Dimri, et, al., 1995 *Proc. Natl. Acad. Sci. USA* "A biomarker that identifies a senescent human cells in culture and in aging skin in vivo," 92: 9363-9367.

D'Ippolito, G., Schiller, P.C., Ricordi, C., Roos, B.A., and Howard, G.A. (1999) "Age-related osteogenic potential of mesenchymal stromal stem cells from human vertebral bone marrow" J Bone Miner Res 14, 1115-22.

Donovan, D., Brown, N.J., Bishop, E.T. and Lewis, C.E. (2001) "Comparison of three in vitro human 'angiogenesis' assays with capillaries formed in vivo" Angiogenesis 4, 113-121.

Dragoo et al. "Tissue-engineered cartilage and bone using stem cells from human infrapatellar fat pads." The Journal of Bone and Joint Surgery. 85(5):740-747 (2003).

Ducy, et, al., 1997 *Cell* "Osf2/Cbfa1: A Transcriptional Activator of Osteoblast Differentiation," 89:747-754.

Eisenberg, Shlomo, "High density lipoprotein metabolism," *Journal of Lipid Research*, 1984, 25:1017-58.

Engleholm, S.A., Spang-Thomsen, M., Brunner N., Nohr, I., and Vindelov, L.L. (1985) "Disaggregation of human solid tumors by combined mechanical and enzymatic methods" Br J Cancer 51, 93-8.

Enomoto, Hirayuki et al., "Cbfal is a Positive Regulatory Factor in Chondrocyte Maturation," J. Biol. Chem. 2000 275:8695-8702.

Entenmann, et al., "Relationship between replication and differentiation cultured human adipocyte precursor cells," *American Phys. Soc.* 1996 270,C1011-C1016.

Eppley, B.L., Smith, P.G., Sadove, A.M., and Delvino, J.J. (1990) "Experimental effects of graft revascularization and consistency on cervicofacial fat transplant survival" J Oral Maxillofac Surg 48, 54-62.

Eremia, S. and N. Newman (2000). "Long-term follow-up after autologous fat grafting: analysis of results from 116 patients followed at least 12 months after receiving the last of a minimum of two treatments" Dermatol Surg 26(12): 1150-8.

Erickson et al. "Chondrogenic potential of adipose tissue derived stromal cells in vitro and in vivo." Biochemical and Biophysical Research Communications. 290(2):763-769 (2002).

Ersek, Robert A. "Transplantation of Purified Autologous Fat: A 3-Year Follow-Up is Disappointing." Plast. Reconst. Surg. 87(2):219-228 (1991).

Eschenhagen, T., Didie, M., Muzel, FI, Schubert, P., Schneiderbanger, K., and Zimmermann, W.H. (2002) "3D engineered hear tissue for replacement therapy" Basic Res Cardiol 97 Suppl 1, 1146-1152.

Fain et al. "Comparison of the Release of Adipolines by Adipose Tissue, Adipose Tissue Matrix, and Adipocytes from Visceral and Subcutaneous Abdominal Adipose Tissues of Obese Humans." Endocrinology. 145(5):2273-2282, at 2278, col. 2 (2004).

Fajas, Lluis, et al., "Transcriptional control of adipogenesis," *Current Opinion in Cell Biology*, 1998, 10:165-73.

Falla, N., Van V., Bierkens, J., Borremans, B., Schoeters, G., and Van Gorp, J. (1993) "Characterization of a 5-flurorouracil-enriched osteoprogenitor population of the murine bone marrow" Blood 82, 3580-91.

Farndale, Richard W. et al., "Improved quantitation and discrimination of sulphated glycosaminoglycans by use of dimethylene blue," *Biochimica et Biophysica Acta*, 1986, 883:173-7.

Ferrari G., et al., 1998 *Science* "Muscle Regeneration by Bone Marrow-Derived Myogenic Progenitors," 279: 1528-1530.

Folkman, J. (1995) "Angiogenesis in cancer, vascular, rheumatoid and other disease" Nat Med 1, 27-31.

Ford, C.N., P.A. Staskowski et al. (1995) "Autologous collagen vocal fold injection: a preliminary clinical study" Laryngoscope 105(9 Pt 1): 944-8.

Formanek et al., 1998, Magnetic cell separation for purification of human oral keratinocytes: an effective method for functional studies without prior cell subcultivation, Eur Arch Otorhinolaryngol, 255:211-215.

Fortier, Lisa, et al., 2000, "Isolation and chondrocytic differentiation of equine bone marrow-derived mesenchymal stem cells," *Am. J. Vet. Res*. 59:1182-1187.

Fraser et al. "Adult Stem Cell Therapy for the Heart." The International Journal of Biochemistry & Cell Biology. 36(4):658-666 (2004).

Fraser JK. Adipose Tissue: Challenging the Marrow Monopoly. Cytotherapy. 4(6):509-510 (2002).

Frederikson and McKay 1988 *J. Neurosci*. "Proliferation and Differentiation of Rat Neuroepithelial Precursor Cells in vivo," 8:1144-1151.

Fridman, et al., 1992 *Int. J. Cancer* "Malignant Transformation of NIH-3T3 Cells After Subcutaneous co-Injection With A Reconstituted Basement Membrane (Matrigel)," 51(5), 740-44.

Fukuda, K. (2001). "Development of regenerative cardiomyocytes from mesenchymal stem cells for cardiovascular tissue engineering" Artif Organs 25(3): 187-93.

Fülöp, Csaba et al., "Expression of Alternatively Spliced Epidermal Growth Factor-like Domains in Aggrecans of Different Species," *The Journal of Biological Chemistry*, 1993, 268:17377-83.

Fulton et al., "Fat Grafting" *Fundamentals of Cosmetic Surgery*. 19(3):523-530 (Jul. 2001).

Ganey et al. "A potential role for cell-based therapeutics in the treatment of intervertebral disc herniation." Eur Spine J. 11(Suppl. 2):S206-214 (2002).

(56) References Cited

OTHER PUBLICATIONS

Ganey et al. "Intervertebral Disc Repair Using Adipose Tissue-Derived Stem and Regenerative Cells." 34(21):2297-2304 (2009).
Garcia-Olmo et al., "Autologous Stem Cell Transplantation for Treatment of Rectovaginal Fistula in Perianal Crohn's Disease: A New Cell-Based Therapy", Int. J Colorectal Dis (2003), 18:451-454.
Gaustad, K.G., Boquest, A.C., Anderson, B.E., Gerdes, A.M., and Collas, P. (2004) "Differentiation of human adipose tissue stem cells using extracts of rat cardiomyocytes" Biochem. Biophys. Res Commun. 314, 420-427.
Geiselhart, A., Neu, S., Buchholz, F., Lang, P., Niethammer, D., and Handgretinger, R. (1996) "Postive selection of CD56+ lymphocytes by magnetic cell sorting" Nat Immun. 15, 227-233.
Gimble et al. "Adipose-Derived Adult Stem Cells: Isolation, Characterization, and Differentiation Potential." Cytotherapy. 5(5):362-369 (2003).
Gimble, Jeffery M. et al., "Adipose tissue-derived therapeutics," *Expert Opin. Biol.*, 2003, 3(5)705-713.
Glowacki, J., "Influence of Age on Human Marrow," *Calcified Tissue International*, 1995, 56(Supp. 1):S50-1.
Greenberg, A.W. and Hammer, D.A. (2001) "Cell separation mediated by differential rolling adhesion" Biotechnol Bioeng 73 111-24.
Grigoradis A., et al., 1988 *J. Cell Biol.* "Differentiation of Muscle, Fat, Cartilage, and Bone from Progenitor Cells Present in a Bone-derived Clonal Cell Population: Effect of Dexamethasone," 106: 2139-2151.
Grigoriadis, Agamemnon E. et al., "Analysis of chondroprogenitor frequency and cartilage differentiation in a novel family of clonal chondrogenic rat cell lines," *Differentiation*, 1996, 60:299-307.
Groutz, A., J.G. Blavias et al (2000) "Outcome results of transurethral collagen injection for female stress incontinence: assessment by urinary incontinence score" J Urol 164(6): 2006-9.
Guerrerosantos, J., A. Gonzalez-Mendoza, et al. (1996). "Long-term survival of free fat grafts in muscle: an experimental study in rats." Aesthetic Plast Surg 20(5): 403-8.
Guerriero, V and JR Florini 1980 *Endocrinology* "Dexamethasone Effects on Myoblast Proliferation and differentiation," 106:1198-1202.
Haab, F., P.E. Zimmern et al (1997) Urinary stress incontinence due to intrinsic sphincteric deficiency: experience with fat and collagen periurethral injections: J Urol 157(4): 1283-6.
Hagege, A.A., Carrion, C., Menasche, P., Vilquin, J.T., Duboc, D., Marolleau, J.P., Desnos, M., and Bruneval, P. (2003) "Viability and differentiation of autologous skeletal myoblast grafts in ischaemic cardiomyopathy" Lancet 361, 491-2.
Hak et al., "Toxic effects of DMSO on cultured beating heart cells at temperatures above zero," Cryobiology, 1973, 10:244-250.
Hall, BK 1981 "Intracellular and extracellular control of differentiation of cartilage and bone," Histochem. J. 13:599-614.
Hamano et al. The induction of angiogenesis by the implantation of autologous bone marrow cells: A novel and simple therapeutic method. Surgery. 130(1):44-54 (2001).
Hamel, M., T. Shaarawy et al (2001) "Deep sclerectomy with collagen implant in patients with glaucoma and high myopia" J Cataract Refract Surg 27(9): 1410-7.
Hardingham, Tim et al., "Studies on the Synthesis, Secretion and Assembly of Proteoglycan Aggregates by Chondrocytes," *Matrices and Cell Differentiation*, 1984, 151:17-29.
Hauner et al. "Cultures of Human Adipose Precursor Cells." Methods in Molecular Biology. 155(1):239-247 (2001).
Hauner H. et al., "Glucocorticoids and Insulin Promote the Differentiation of Human Adipocyte Precursor Cells into Fat Cells," *Journal of Clinical Endocrinology and Metabolism*, 64:832-5, 1987.
Hauner, et al., "Endothelin-1 Inhibits the Adipose Differentiation of Cultured Human Adipocyte Precursor Cells," *Metabolism* 1994 43(2) pp. 227-232.
Hauner, Hans et al., "Promoting Effect of Glucocorticoids on the Differentiation of Human Adipocyte Precursor Cells Cultured in a Chemically Defined Medium," *Journal of Clinical Investigation*, 84:1663-70, 1989.
Hausman, et al., "The Influence of Extracellular Matrix Substrata on Preadipocyte Development in Serum-Free Cultures of Stromal-Vascular Cells," *J. Anim.Sci.* 1996 74(9), 2117-2128.
Haynesworth, S. E. et al., "Cell Surface Antigen on Human Marrow-Derived Mesenchymal Cells are Detected by Monoclonal Antibodies," *Bone*, 1992, 13:69-80.
Hemmrich, K. et al. "Implantation of preadipocyte-loaded hyaluronic acid-based scaffolds into nude mice to evaluate potential for soft tissue engineering." *Biomaterials* 26, 7025-7037 (2005).
Hemstreet, G.P. 3, Enoch, P.G., and Pretlow, T.G. 2 (1980) "Tissue disaggregation of human renal cell carcinoma with further isopyknic and isokinetic gradient purification" Cancer Res 40, 1043-9.
Herman, Ira M. and Patricia D'Amore, "Microvascular Pericytes Contain Muscle and Nonmuscle Actins," *J. Cell Biol.* 1985 101:43-52.
Hess, D.C. et al. Hematopoietic Origin of Microglial and Perivascular Cells in Brain, Experimental Neurology, Apr. 2004, vol. 186, pp. 134-144.
Hironori et al. The Japan Endocrine Society Journal. 80(1):90 (Apr. 2004).
Hong et al. "Adipose tissue engineering by human adipose-derived stromal cells." *Cells Tissues Organs* 183, 133-140 (2006).
Horwitz et al., 2005, Clarification of the nomenclature for MSC: The International Society for Cellular Therapy position statement, 7(5):393-395.
Horwitz, E. M., D.J. Prockop, et al. (1999). "Transplantability and therapeutic effects of bone marrow-derived mesenchymal cells in children with osteogenesis imperfecta." Nat Med 5(3): 309-13.
Horwitz et al, 2001, Clinical responses to bone marrow transplantation in children with severe osteogenesis imperfecta, Blood, 97(5):1227-31.
Hsiung, M. W., P. Woo et al (2000) "Fat augmentation for glottic insufficiency" Laryngoscope 110(6): 1026-33.
Huang, J.I., S.R. Beanes, et al. (2002) "Rat extramedullary adipose tissue as a source of osteochondrogenic progenitor cells" Plast Reconstr Surg 109(3): 1033-41; discussion 1042-3.
Huibregtse, Barbara, et al., 1998, "Effect of Age and Sampling Site on the Chondro-Osteogenic Potential of Rabbit Marrow-derived Mesenchymal Progenitor Cells," *Journal of Orthopaedic Research*. 18:18-24.
Hur et al. Akt is a Key Modulator of Endothelial Progenitor Cell Trafficking in Ischemic Muscle. Stem Cells. 25:1769-1778 (2007).
Huss, Ralf, "Isolation of Primary and Immortalized CD34–Hematopoietic and Mesenchymal Stem Cells from Various Sources," *Stem Cells*, 2000, 18:1-9.
Hutley, L.J., A.C. Herington, et al. (2001) "Human adipose tissue endothelial cells promote preadipocyte proliferation" Am J. Physiol Endocrinol Metab 281(5): E1037-44.
Iwasaki, Motoki et al., "Regulation of Proliferation and Osteochondrogenic Differentiation of Periosteum-Derived Cells by Transforming Growth Factor-b and Basic Fibroblast Growth Factor," *Journal of Bone and Joint Surgery*, 1995, 77A:543-54.
Jackson et al. Regeneration of ischemic cardiac muscle and vascular endothelium by adult stem cells. Journal Clinical Investigation. 107(11): 1395-1402 (2001).
Jaiswal, et al., 1997 "Osteogenic Differentiation of Purified, Culture-Expanded Human Mesenchymal Stem Cells In Vitro," J. Cell Biochem. 64:295-312.
Jaiswal et al., 2000, Adult human mesenchymal stem cell differentiation to the osteogenic or adipogenic lineage is regulated by mitogen-activated protein kinase, J Biol Chem, 275:9645-52.
Jiang, Y., Jahagirdar, B.N., Reinhardt, R.L., Schwartz, R.E., Keene, C.D., Ortiz-Gonzalez, X.R., Reyes, M. Lenvik, T., Lund, T., Blackstad, M., Du, J., Aldrich, S., Lisberg, A., Low, W.C., Largaespada, D.A., and Verfaillie, C.M. (2002a) "pluripotency of mesenchymal stem cells derived from adult marrow" Nature 418, 41-9.
Jiang, Y., Vaessen, B., Lenvik, T., Blackstad, M., Reyes, M., and Verfaillie, C.M. (2002b) "Multipotent progenitor cells can be isolated from postnatal murine bone marrow, muscle, and brain" Exp Hematol 30, 896-904.

(56) References Cited

OTHER PUBLICATIONS

Johnson, P. R. et al., "Uncontrolled adipocyte proliferation is not the primary lesion in the genetically-obese obese Zucker rat," *International Journal of Obesity*, 5:563-70, 1981.
Johnstone B., et al., 1998 "In Vitro Chondrogenesis of Bone Marrow-Derived Mesenchymal Progenitor Cells," Exp. Cell Res. 238: 265-272.
Joyner, C.J., Triffitt, J., Puddle, B., and Athanasou, N.A. (1999) "Development of a monoclonal antibody to the aP2 protein to identify adipocyte precursors in tumours of adipose differentiation" Pathol. Res Pract. 195, 461-466.
Jurgens et al. "Effect of tissue-harvesting site on yield of stem cells derived from adipose tissue: implications for cell-based therapies." Cell Tiss. Res. 332:415-426 (2008).
Kale et al. "Bone marrow stem cells contribute to repair of the ischemically injured renal tubule" J. Clinical Investigation, vol. 112, No. 1 42-49 (Jul. 2003).
Kamer, F.M. and M.M. Churukian (1984) "Clinical use of injectable collagen. A three-year retrospective review" Arch Otolaryngol 110(2): 93-8.
Kamihata et al. "Improvement of collateral perfusion and regional function by implantation of peripheral blood mononuclear cells into ischemic hibernating myocardium." Thromb Vascular Biology. 22:1804-1810 (2002).
Kang et al. "Improvement of neurological deficits by intracerebral transplantation of human adipose tissue-derived stromal cells after cerebral ischemia in rats." Experimental Neurology. 183(2):355-366 (2003).
Kang et al. "Interactions between human adipose stromal cells and mouse neural stem cells in vitro." Developmental Brain Research. 145(1): 141-149 (2003).
Kania, et al., 1990 "The *Drosophila* segmentation gene *runt* encodes a novel nuclear regulatory protein that is also expressed in the developing nervous system," Genes Dev. 4:1701-1713.
Karlsson et al., "Long-term storage of tissues by cryopreservation: critical issues," Biomaterials 1996, 17(3):243-256.
Katz, A.J., Hedrick, M.H., Llull, R., and Futrell, J.W. (2001) "A novel device for the simple and efficient refinement of liposuctioned tissue" Plast Reconstr Surg 107, No. 2, 595-597.
Katz, Adam J. et al., "Emerging Approaches to the Tissue Engineering of Fat," *Clinics in Plastic Surgery*, 1999, 26:587-603.
Katz, B.E., Bruck, M.C. and Coleman, W. P. 3 (2001b) "The benefits of powered liposuction versus traditional liposuction: a paired comparison analysis" Dermatol Surg 27, 863-7.
Kaushal et al., 2001, Functional small-diameter neovessels cretaed using endothelial progenitor cells expanded ex vivo, Nat Med 7:1035-40.
Kawamoto et al., 2003, Intramyocardial transplantation of autologous endothelial progenitor cells for therapeutic neovascularization of myocardial ischemia, Circulation 107:461-8.
Kehlen, A. et al., 2000 *J. Cell Biochem*. "Increased Lymphocytic Aminopeptidase N/CD13 Promoter Activity After Cell-Cells Contact," 80:115-123.
Kern, P.A., A. Knedler, et al. (1983) Isolation and culture of microvascular endothellium from human adipose tissue: J Clin Invest 71(6): 1822-9.
Killinger, D. W. et al., "Influence of Adipose Tissue Distribution on the Biological Activity of Androgens," *Annals New York Academy of Sciences*, 595:199-211, 1990.
Killinger, Donald W. et al., "The Relationship Between Aromatase Activity and Body Fat Distribution," *Steroids*, 50:61-72, 1987.
Kim, et al. "Wound healing effect of adipose-derived stem cells: A critical role of secretory factors on human dermal fibroblasts." Journal of Dermatological Science. 48(1): 15-24 (2007).
Kimura et al. "Adipose tissue engineering based on human preadipocytes combined with gelatin microspheres containing basic fibroblast growth factor." *Biomaterials* 24, 2513-2521 (2003).
Kirsch, Thorsten and Klaus von der Mark, "Remodelling of collagen types I, II and X and calcification of human fetal cartilage," *Bone and Mineral*, 1992, 18:107-17.

Klein, A.W. (2001) "Skin filling. Collagen and other injectables of the skin" Dermatol Clin 19(3): 491-508, ix.
Kosher, RA, et al., 1986 *J. Cell Biol*. "Collagen Gene Expression During Limb Cartilage Differentiation," 102:1151-1156.
Kosher, Robert A. and Michael Solursh, "Widespread Distribution of Type II Collagen during Embryonic Chick Development," *Developmental Biology*, 1989, 131:558-66.
Koufman, J.A. (1991) "Lipoinjection for vocal cord paralysis" Laryngoscope 101(12 Pt 1): 1385.
Kuri-Harcuch et al., 1984, Extracellular matrix production by mouse 3T3-F442A cells during adipose differentiation in culture, Differentiation, 28:173-178.
Lafontan, M. et al., "Réflexions sur une nouvelle approche de chirurgie plastique réparatrice: la réimplantation de fragments de tissu adipeux prélevés par liposuccion," *Ann. Chir. Plast. Esthet.*, 34:77-81, 1989.
Lam, Anson and Ronald Moy, "The Potential for Fat Transplantation," *J. Dermatol. Surg. Oncol.*, 18:432-4, 1992.
Lamouille, S., Mallet, C., Feige, J.J., and Bailly, S. (2002) "Activin receptor-like kinase 1 is implicated in the maturation phase of angiogenesis" Blood 100, 4495-4501.
Lanier, L.L. et al, 1991 *J. Immunol*. "Molecular and Functional Analysis of Human Natural Killer Cell-Associated Neural Cells Adhesion Molecule (N-Cam/CD56)," 146:4421-4426.
Lasch, J., Kullertz, G., and Opalka, J.R. (2000) "Separation of erythrocytes into age-related fractions by density or size? Counterflow centrifugation" Clin Chem Lab Med 38, 629-632.
Latoni, J.D., D.M. Marshall et al (2000 "Overgrowth of fat autotransplanted for correction of localized steroid-induced atrophy" Plast Reconstr Surg 106(7): 1566-9.
Lawson-Smith, M.J. and McGeachie, J.K. 1998 *J. Anat*. "The identification of myogenic cells in skeletal muscle, with emphasis on the use of tritiated thymidine autoradiography and desmin antibodies," 192:161-171.
Lazarus, Hillard M. et al., "Human Bone Marrow-Derived Mesenchymal (Stromal) Progenitor Cells (MPCs) Cannot Be Recovered from Peripheral Blood Progenitor Cell Collections," *Journal of Hematotherapy*, 1997, 6:447-55.
Leboy, et al., 1991 *J. Cell Physiol*. "Dexamethasone Induction of Osteoblast mRNAs in Rat Marrow Stromal Cell Cultures," 146:370-378.
Leboy, Phoebe S. et al., "Ascorbic Acid Induces Alkaline Phosphatase, Type X Collagen, and Calcium Deposition in Cultured Chick Chondrocytes," *The Journal of Biological Chemistry*, 1989, 264:17281-6.
Lecoeur, L. and J. P. Ouhayoun, "In vitro induction of osteogenic differentiation from non-osteogenic mesenchymal cells," *Biomaterials*, 18:989-93, 1997.
Lee et al., 1992, Adhesion Molecules in Skeletogenesis: I. Transient Expression of Neural Cell Adhesion Molecules (NCAM) in Osteoblasts During Endochondral and Intramembranous Ossification, *Journal of Bone and Mineral Research*, 7:1435-46.
Lee, J. H., Z. Ilic, et al. (1996) "Cell kinetics of repair after allyl alcohol-induced liver necrosis in mice" Int J Exp Pathol 77(2): 63-72.
Lee, P.E., R.C. Knug, et al. (2001) "Periurethral autologous fat injection as treatment for female stress urinary incontinence: a randomized double-blind controlled trial" J Urol 165(1): 153-8.
Lehner, M. and Holter, W. (2002) "Endotoxin-free purification of monocytes for dendritic cell generation via discontinuous density gradient centrifugation based on diluted Ficoll-Paque Plus" Int Arch Allergy Immunol 128, 73-76.
Lendahl, et al., 1990 *Cell* "CNS Stem Cells Express a New Class of Intermediate Filament Protein," 60:585-595.
Lennon et al., 1995, A chemically defined medium supports in vitor proliferation and maintains the osteochondral potential of rat marrow-derived mesenchymal stem cells, Exp Cell Res, 219:211-22.
Lennon, Donald P. et al., "Human and Animal Mesenchymal Progenitor Cells from Bone Marrow: Identification of Serum for Optimal Selection and Proliferation," *In Vitro Cell. Dev. Biol.—Animal*, 1996, 32:602-11.
Lenoir, N. 2000 *Science* "Europe Confronts the Embryonic Stem Cell Research Challenge," 287:1425-1427.

(56) References Cited

OTHER PUBLICATIONS

Lev, Robert and S. S. Spicer, "Specific Staining of Sulphate Groups with Alcian Blue at Low pH," *J. Histochem. Cytochem.*, 1964, 12:309-10.

Lin, et al. "Hematopoietic Stem Cells Contribute to the Regeneration of Renal Tubules After Renal Ischmia-Reperfusion Injury in Mice." Journal of the American Society of Nephrology. 14: 1188-1199 (2003).

Linsenmayer, Thomas et al., 1998, "Type X Collagen: A Hypertrophic Cartilage-Specific Molecule," *Pathol. Immunopathol.* 7:14-19.

Liu, S.H., R.S. Yang et al (1995) "Collagen in tendon, ligament and bone healing. A current review" Clin Orthop (318): 265-78.

Loncar, 1992, Ultrastructural analysis of differentiation of rat endoderm in vitro. Adipose vascular-stromal cells induce endoderm differentiation, which in turn induces differentiation of the vascular-stromal cells into chondrocytes, *J. Submicrosc. Cytol. Pathol.*, 24:509-19.

Long, Michael W. et al., "Age-Related Phenotypic Alterations in Populations of Purified Human Bone Precursor Cells," *The Journals of Gerontology*, 1999, 54A:B54-62.

Lucas, P. A. et al., "Isolation of Putative Mesenchymal Stem Cells from Rat Embryonic and Adult Skeletal Muscle," *In Vitro Cell Dev. Biol.*, 1992, 28:154A.

Lucas, Paul A. et al., "Mesenchymal Stem Cells From Granulation Tissue," *J. Cell Biochem*, 1993 17E:122, R212.

Lumelsky, N., et al. 2001 *Science* "Differentiation of Embryonic Stem Cells to Insulin-Secreting Structures Similar to Pancreatic Islets," 292:1389-1394.

Lund et al. "Granulocyte colony-stimulating factor mobilized CFU-F can be found in the peripheral blood but have limited expansion potential." Haematologica. 93(6):908-912 (2008).

Luskey, B.D., Lim, B., Apperley, J.F., Orkin, S.H., and Williams, D.A. (1990) "Gene transfer into murine hematopoietic stem cells and bone marrow stromal cells" Ann NY Acad Sci 612, 398-406.

Luttun et al., 2002, Revascularization of ischemic tissues by PIGF treatment, and inhibition of tumor angiogenesis, arthritis and atherosclerosis by anti-Fltl, Nat Med 8:831-40.

Lynch, et al., 1995, The Influence of Type I Collagen on the Development and Maintenance of the Osteoblast Phenotype in Primary and Passaged Rat Calvarial Osteoblasts: Modification of Expression of Genes Supporting Cell Growth, Adhesion, and Extracelluar Matrix Mineralization, Exp. Cell Res, 216:35-45.

MacDougald, Ormond A. and M. Daniel Lane, "Transcriptional Regulation of Gene Expression During Adipocyte Differentiation," *Annu. Rev. Biochem.*, 1995, 64:345-73.

Mainwaring, G. and Rowley, A.F. (1985) "Separation of leucocytes in the dogfish (*Scyliorhinus canicula*) using density gradient centrifugation and differential adhesion to glass coverslips" Cell Tissue Res 241, 283-90.

Majeska, Robert J. and Gideon A. Rodan, "The Effect of 1,25(OH)2D3 on Alkaline Phosphates in Osteoblastic Osteosarcoma Cells," *J. Biol. Chem.* 1982 257:3362-3365.

Majumdar, Mx., Thiede, M.A., Mosca, J.D., Moorman, M., and Gerson, S.L. (1998) "Phenotypic and functional comparison of cultures of marrow-derived mesenchymal stem cells (MSCs) and stromal cells" J Cell Physiol 176, 57-66.

Malaval, et al., 1994 *J. Cell. Physiol.* "Cellular Expression of Bone-Related Proteins During In Vitro Ostegenesis in Rat Bone Marrow Stromal Cell Culture," 158:555-572.

Manduca, et al., 1992 *Eur. J. Cell Biol*."Chondrogenic differentiation in chick embryo osteoblast cultures," 57:193-201.

Manetti et al. (2000) "Fibroblast growth factors and their inhibitors" Curr. Pharm. Des 6, 1897-1924.

Marchlinski et al., 1987,Experimental myocardial cryoinjury: local electromechanical changes, arrhythmogenicity, and methods for determining depth of injury, Pacing Clin Electrophysiol 10:886-901.

Marko, et al., "Isolation of a Preadipocyte Cell Line from Rat Bone Marrow and Differentiation to Adipocytes," *Endocrinology* 1995 136(10), 4582-4588.

Martin, et al., 1999 *Exp. Cell Res*. "Mammalian Chondrocytes Expanded in the Presence of Fibroblast Growth Factor 2 Maintain the Ability to Differentiate and Regenerate Three-Dimensional Cartilaginous Tissue," 253:681-688.

Martinez-Estrada et al. "Human adipose tissue as a source of Flk-1 <+> cells: new method of differentiation and expansion." Cardiovascular Research. 65(2):328-333 (2005).

Masuda et al. "Novel strategy for soft tissue augmentation based on transplantation of fragmented omentum and preadipocytes." *Tissue Eng* 10, 1672-1683 (2004).

Masuda,et al. "Photocured, styrenated gelatin-based microspheres for de novo adipogenesis through corelease of basic fibroblast growth factor, insulin, and insulin-like growth factor I." *Tissue Eng* 10, 523-535 (2004).

Megeney, et al., 1996 *Genes Dev*. "MyoD is required for myogenic stem cell function in adult skeletal muscle," 10:1173-1183.

Mezey, et al. "Comment on 'Failure of Bone Marrow Cells to Transdifferentiate into Neural Cells in Vivo.'" Science. 299:1184b (2003).

Miller, J.J. and J.C. Poop (2002) "Fat hypertrophy after autologous fat transfer" Opthal Plast Reconstr Surg 18(3): 228-31.

Mills, J.D., Fischer, D., and Villanueva, F.S. (2000) "Coronary collateral development during chronic ischemia: serial assessment using harmonic myocardial contrast echocardiography" J Am Coll Cardiol 36(2):618-24.

Miranville et al. "Human adipose tissue-derived stem cells improve postnatal neovascularization." International Journal of Obesity. 28(Suppl 1):S100 (May 2004).

Miranville et al. "Human adipose tissue-derived stem cells improve blood flow in the ischemic mouse hind-limb" Circulation, vol. 108, No. 17, Supp. IV, 164 (Oct. 2003).

Miranville, et al. "Improvement of postnatal neovascularization by human adipose tissue-derived stem cells." Circulation, American Heart Association. 110(3):349-355 (2004).

Mizuno, H., P.A. Zuk, et al. (2002) "Myogenic differentiation by human processed lipoaspirate cells" Plast Reconstr Surg 109(1): 199-209; discussion 210-1.

Mohr et al., 2001, Simultaneous immunomagnetic CD34+ cell selection and B-cell depletion in peripheral blood progenitor cell samples of patients suffering from B-cell non-Hodgkin's lymphoma Clin Cancer Res 7:51-57.

Molkentin and Olson 1996 *Curr. Opin. Genet. Dev.* "Defining the regulatory networks for muscle development," 6:445-453.

Monteiro, P., Antunes, A., Goncalves, L.M., and Providencia, L.A. (2003) "Long-term clincal impact of coronary-collateral vessels after acute myocardial infarction" Rev. Port. Cardiol 22, 1051-1061.

Morizono, K., De Ugarte, D.A., Zhu, M., Zuk, P., Elbarbary, A., Ashjian, P., Benhaim, P. Chen, I.S., and Hedrick, M.H. (2003) "Multilineage cells from adipose tissue as gene delivery vehicles" Hum Gene Ther 14, 59-66.

Mosca et al., 2000, Mesenchymal stem cells as vehicles for gene delivery, Clin Orthop, 379S:71-90.

Mullen, Richard J. et al., "NeuN, a neuronal specific nuclear protein in vertebrates," *Development*, 1992, 116:201-11.

Muller et al. "Selection of ventricular-like cardiomyocytes from ES cells in vitro." The FASEB Journal. 14:2540-2548 (2000).

Mullins et al., 1996, Allergic reactions to oral, surgical and topical bovine collagen. Anaphylactic risk for surgeons, Aust N Z J Ophthalmol 24(3):257-260.

Mundlos, et al., 1997 *Cell* "Mutations Involving the Transcription Factor CBFA12 Cause Cleidocranial Dysplasia," 89:773-779.

Muramatsu, T., Nakamura, A., and Park, H.M. (1998) "In vivo electroportion: a powerful and convenient means of nonviral gene transfer to tissues of living animals (Review)" Int J Mol Med 1, 55-62.

Murayama, T., O.M. Tepper, et al. (2002) "Determination of bone marrow-derived endothelial progenitor cells significance in angiogenic growth factor-induced neovascularization in vivo" Exp Hematol 30(8): 967-72.

Murry CE et al. 2004. Hematopoietic stem cells do not transdifferentiate into cardiac myocytes in myocardial infarcts. Nature 428: 664-668.

Murry et al., 1996, Skeletal myoblast transplantation for repair of myocardial necrosis, J Clin Invest 98(11):2512-2523.

(56) References Cited

OTHER PUBLICATIONS

Muschler, G.F., Nitto, H., Boehm, C.A., and Easley, K.A. (2001) "Age-and gender-related changes in the cellularity of human bone marrow and the prevalence of osteoblastic progenitors" J Orthop Res 19(1), 117-25.
Myllyharju, J. (2000) "Recombinant collagen trimers from insect cells and yeast" Methods Mol Biol 139: 39-48.
Nagle, R. B. et al., "Factor VII-Associated Antigen in Human Lymphatic Endothelium," *Lymphology*, 1987, 20:20-4.
Nagy, J.A., Dvorak, A. M., and Dvorak, H.F. (2003) VEGF-A (164/165) and PIGF: roles in angiogenesis and arteriogenesis: Trends Cardiovasc Med 13, 169-175.
Nakahara, H. et al., "Bone and Cartilage Formation in Diffusion Chambers by Subcultured Cells Derived from the Periosteum," *Bone*, 1990, 11:181-8.
Nakajima, I. et al., 1998, "Adipose tissue extracellar matrix: newly organized by adipocytes during differentiation," *Differentiation* 63:193-200.
Nakano, Hirotaka et al., "RT-PCR Suggests Human Skeletal Muscle Origin of Alveolar Soft-Part Sarcoma," *Oncology*, 2000, 58:319-23.
Nambu et al. Japanese Society for Biomaterials, Conference Proceedings. 25:96 (2003).
Nathan, Suresh et al. "Cell-Based Therapy in the Repair of Osteochrondral Defects: A Novel Use for Adipose Tissue", Tissue Engineering, vol. 9, No. 4, 2003.
Nehls, A. and D Drenckhahn 1991 *J. Cell Biol.* "Heterogeneity of Microvascular Pericytes for Smooth Muscle Type Alpha-Actin," 113:147-154.
Nerem, R.M. and Ensely, A.E. (2004) "The tissue engineering of blood vessels and the heart" Am J Transplant 4 Supp 6, 36-42.
Nguyen, A., K.A. Pasyk et al. (1990) "Comparative study of survival of autologous adipose tissue taken and transplanted by different techniques" Plast Reconstr Surg 85(3): 378-86; discussion 387-9.
Nishimori, M. Yamada, Y., Hoshi, K., Akiyama, Y., Hosi, Y., Morishima, Y., Tsuchida, M., Fukuhara, S., and Kodera,Y. (2002) "Health-related quality of life of unrelated bone marrow donors in Japan" Blood 99(6), 1995-2001.
Novakofski, Jan E., "Primary Cell Culture of Adipose Tissue," *Biology of the Adipocyte: Research Approaches*, Van Nostrand Reinhold Company, NY, 1987 160-97.
O'Driscoll, Shawn W., "Current Concepts Review: The Healing and Regeneration of Articular Cartilage," *Journal of Bone and Joint Surgery*, 1998, 80A:1795-812.
Odorico, J.S., Kaufman, D.S., and Thomson, J.A. (2001) "Multilineage differentiation from human embryonic stem cells lines" Stem Cells 19, 193-204.
Ohgushi, H. and Caplan, A.I. (1999) "Stem cell technology and bioceramics: from cell to gene engineering" J Biomed Mater Res 48, 913-27.
Olson, E. N. et al., "Know Your Neighbors: Three Phenotypes in Null Mutants of the Myogenic bHLH Gene MRF4," *Cell*, 1996, 85:1-4.
Ooi, K., M.P. Lacy et al (1991) "salt-soluble collagen and elastin in the human aorta and pulmonary artery" Exp Mol Pathol 55(1): 25-9.
Orlic, D., J. Kajstura, et al. (2001) "Bone marrow cells regenerate infarcted myocardium" Nature 410(6829): 701-5.
Orlic, D., J. Kajstura, et al. (2001) "Transplanted adult bone marrow cells repair myocardial infarcts in mice" Ann N Y Acad Sci 938: 221-9, discussion 229-30.
Owen et al., 1990, Progressive Development of the Rat Osteoblast Phenotype in Vitro: Reciprocal Relationships in Expression of Genes Associated with Osteoblast Proliferation and Differentiation During Formation of the Bone Extracellular Matrix, J. Cell Physiol., 143:420-430.
Pairault, Jacques and Howard Green, "A study of the adipose conversion of suspended 3T3 cells by using glycerophosphate dehydrogenase as differentiation marker," *Proc. Natl. Acad. Sci. USA*, 1979, 76:5138-42.
Palma, P.C., C.L. Riccetto, et al. (1997) "Repeated lipoinjections for stress urinary incontinence" J Endourol 11(1): 67-70.
Park, S. R. et al., "Interconversion Potential of Clone Human Marrow Adipocytes in Vitro," *Bone*, 1999, 24:549-54.
Patrick et al. "Long-term implantation of preadipocyte-seeded PLGA scaffolds." Tissue Eng. 8(2):283-93 (2002).
Patrick et al. "Preadipocyte Seeded PLGA Scaffolds for Adipose Tissue Engineering." Tissue Eng. 5(2): 139-151 (1999).
Paul S.R., et al., 1991 *Blood* "Stromal Cell-Associated Hematopoiesis: Immortalization and Characterization of Primate Bone Marrow-Derived Stromal Cell Line," 77: 1723-33.
Pedersen, S. B. et al., "Identification of oestrogen receptors and oestrogen receptor mRNA in human adipose tissue," *European Journal of Clinical Investigation*, 26:262-9, 1996.
Pera, M.F., Reubinoff, B., and Trounson, A. (2000) "Human embryonic stem cells" J Cell Sci 113 (Pt 1) 5-10.
Periasamy, Muthu et al., "Regulation of myosin heavy-chain gene expression during skeletal-muscle hypertrophy," *Biochem. J.* 1989 257:691-698.
Perin et al. "Transendocardial, autologous bone marrow cell transplantation for severe, chronic ischemic heart failure." Circulation. 107(18):2294-2302 (2003).
Pettengell et al. "Peripheral Blood Progenitor Cell Transportation in Lymphoma and Leukemia Using a Single Apheresis." Blood. 82:3770-3777 (1993).
Pettersson, Per et al., "Adipocyte Precursor Cells in Obese and Nonobese Humans," *Metabolism*, 34:808-12, 1985.
Pettersson, Per et al., "Cells in Human Adipose Tissue Developing into Adipocytes," *Acta Med Scand*, 1984, 215:447-51.
Pierelli, Luca et al., "CD34+/CD105+ cells are enriched in primitive circulating progenitors residing in the G0 phase of the cell cycle and contain all bone marrow and cord blood CD34+/CD38low/− precursors," *British Journal of Haematology*, 2000, 108:610-20.
Piersma et al. "Migration of fibroblastoid stromal cells in murine blood." Cell Tissue Kinet. 18:589-595 (1985).
Pipp et al., 2003, VEGFR-1-selective VEGF homologue PIGF is arteriogenic: evidence for a monocyte-mediated mechanism, Circ. Res 92:378-385.
Pittenger, M.F., A.M. Mackay, et al. (1999) "Multilineage potential of adult human mesenchymal stem cells" Science 284(5411): 143-7.
Planat-Benard et al. "Spontaneous Cardiomyocyte Differentiation from Adipose Tissue Stroma Cells." Circulation Research. 94(2):223-229 (2004).
Planat-Bernard, et al. "Plasticity of Human Adipose Lineage Cells toward Endothelial Cells Physiological and Therapeutic Perspectives." Circulation, American Heart Association. 109(5):656-663 (2004).
Poliard, a. et al., "Controlled Conversion of an Immortalized Mesodermal progenitor Cell Towards osteogenic, Chondrogenic, or Adipogenic Pathways," *J. Cell Biol.* 1995 130;1461-1472.
Price, Paul A. and Sharon A. Baukol, "1,25-Dihydroxyvitamin D3 Increases Synthesis of the Vitamin K-dependent Bone Protein by Osteosarcoma Cells," *The Journal of Biological Chemistry*, 1980, 255:11660-3.
Price, Paul A. et al., "Matrix GLA Protein, A New γ-Carboxyglutamic Acid-Containing Protein Which is Associated With the Organic Matrix of Bone," *Biochem. Biophys. Res. Commun.*, 1983 117:765-771.
Price, Paul A., "GLA-Containing Proteins of Bone," *Connective Tissue Research*, 1989, 21:51-60.
Prince et al., 2002, Isolex 300i CD34-selected cells to support multiple cycles of high-dose therapy, Cytotherapy 4:137-45.
Probst, M. et al., "Homologous bladder augmentation in dog with the bladder acellular matrix graft," *BJU International*, 2000, 85:362-71.
Prockop D.J. 1997 *Science* "Marrow Stromal Cells as Stem Cells for Nonhematopoietic Tissues," 276: 71-74.
Prockop, D.J., S.A. Azizi, et al. (2000) Potential use of marrow stromal cells as therapeutic vectors for diseases of the central nervous system: Prog Brain Res 128:293-7.
Purna, S.K. and M. Babu (2000) "Collagen based dressings—a review" Burns 26(1): 54-62.
Qian, X., Jin, L., and Lloyd, R.V. (1998) Percoll Density Gradient-Enriched Populations of Rat Pituitary Cells: Interleukin 6 Secretion, Proliferative Activity, and Nitric Oxide Synthase Expression: Endocr. Pathol. 9, 339-346.

(56) References Cited

OTHER PUBLICATIONS

Quirici, N., Soligo, D., Bossolasco, P., Servida, F., Lumini, C., and Deliliers, G.L. (2002) "Isolation of bone marrow mesenchymal stem cells by anti-nerve growth factor receptor antiobidies" Exp Hematol 30, 783-91.

Rajnoch, C., Chachques, J.C., Berrebi, A., Bruneval, P., Benoit, M.O., and Carpentier, A. (2001) "Cellular therapy reverses myocardial dysfunction" J Thorac Cardiovasc Surg 121(5), 871-8.

Ramsay, T. G. et al., "Pre-Adipocyte Proliferation and Differentiation in Response to Hormone Supplementation of Decapitated Fetal Pig Sera," *J. Anim. Sci.*, 64:735-44, 1987.

Rando, et al., 1995 *Exp. Cell Res.* "The Fate of Myoblasts Following Transportation into Mature Muscle," 220:383-389.

Rando, Thomas A. and Helen M. Blau, "Primary Mouse Myoblast Purification, Characterization, and Transplantation for Cell-mediated Gene Therapy," *J. Cell Biol* 1994 125:1275-1287.

Rangappa et al., 2003, Transformation of adult mesenchymal stem cells isolated from the fatty tissue into cardiomyocytes, Ann Thorac. Surg 75, 775-779.

Rehman, et al. "Angiogenic potential of subcutaneous adipose stromal cells for autologous cell therapy." Journal of the American College of Cardiology. 41(6)(Suppl A): 308A (Mar. 19, 2003).

Rehman, et al. "Secretion of angiogenic and antiapoptotic factors by human adipose stromal cells." Circulation. 109(10):1292-1298 (2004).

Reinecke H et al. 2002. Skeletal muscle stem cells do not transdifferentiate into cardiomyocytes after cardiac grafting. J. Mol. Cell. Cardiol. 34: 241-249.

Remacle, M., G. Lawson et al (1999) "Correcting vocal fold immobility by autologous collagen injection for voice rehabilitation. A short-term study." Ann Otol Rhinol Laryngol 108(8): 788-83.

Remme, W.J. (2000) "Overview of the relationship between ischemia and congestive heart failure" Clin Cardiol 23, 4-8.

Reyes, M., Lund, T., Lenvik, T., Aguiar, D., Koodie, L., and Verfaillie, C.M. (2001) "Purification and ex vivo expansion of postnatal human marrow mesodermal progenitor cells" Blood 98, 2615-2625.

Richardson, J. B. et al., "Repair of human articular cartilage after implantation of autologous chondrocytes," *The Journal of Bone and Joint Surgery*, 1999, 81:1064-8 ).

Rickard, David J. et al., "Isolation and Characterization of Osteoblast Precursor Cells from Human Bone Marrow," *Journal of Bone and Mineral Research*, 1996, 11:312-24.

Rodriguez et al. "The human adipose tissue is a source of multipotent stem cells." Biochimie. 87(1):125-128 (2005).

Rubens, F. D. et al., "Tissue Factor Expression by Cells Used for Sodding of Prosthetic Vascular Grafts," *Journal of Surgical Research*, 72:22-8, 1997.

Russell, S.W., Doe, W.F., Hoskins, R.G. and Cochrane, C.G. (1976) "inflammatory cells in solid murine neoplasms. I. Tumor disaggregation and identification of constituent inflammatory cells" Int J Cancer 18, 322-30.

Saalbach, A., et al., 1997 *Cell and Tiss. Res.* "The Fibroblast-specific MAb AS02: a novel tool for detection and elimination of human fibroblasts," 290:593-599.

Safford et al. "In vivo engraftment and differentiation of murine adipose derived stromal cells" Blood, vol. 100, No. 11, 731a, (Nov. 2002).

Safford, Kristine M. et al., "Neurogenic differentiation of murine and human adipose-derived stromal cells," *Biochemical and Biophysical Research Communications*, 2002, 371-379.

Saito et al. "Transcoronary implantation of bone marrow stromal cells ameliorates cardiac function after myorcardial infarction." The Journal of Thoracic and Cardiovascular Surgery. 126(1):114-122 (2003).

Sanchez-Ramos, et al., 2000 "Adult Bone Marrow Stromal Cells Differentiate into Neural Cells in Vitro," Exp. Neurol. 164:247-256.

Sarnat, Harvey B. et al., "Neuronal nuclear antigen (NeuN): a marker of neuronal maturation in the early human fetal nervous system," *Brain & Development*, 1998, 20:88-94.

Sattler et al. "Liporecycling: a technique for facial rejuvination and body contouring" Dermantol. Surg. vol. 26, No. 12, 1140-1144 (Dec. 2000).

Savitz et al. "Cell Transplantation for stroke." Annals of Neurology. 52(3):266-275 (2002).

Scherberich, A. and A. Beretz (2000) "Culture of vascular cells in tridimensional (3-D) collagen: a methodological review" Therapie 55(1): 35-41.

Schoeller et al. "Histomorphologic and volumetric analysis of implanted autologous preadipocyte cultures suspended in fibrin glue: a potential new source for tissue augmentation." Aesthetic Plastic Surgery. 25(1):57-63 (2001).

Scholz, D., Cai, W.J., and Schaper, W. (2001) "Arteriogenesis, a new concept of vascular adaptation in occlusive disease" Angiogenesis 4, 247-257.

Scholz, D., Elasaesser, H., Sauer, A., Friedrich, C., Luttun, A., Carmeliet, P., and Schaper, W. (2003) "Bone marrow transplantation abolishes inhibition of arteriogenesis in placenta growth factor (PlGF)—mice" J Mol Cell Cardiol 35, 177-184.

Scholz,D., Ziegelhoeffer, T., Helisch, A., Wagner, S., Friedrich, C., Podzuweit, T. and Schaper, W. (2002) "Contribution of arteriogenesis and angiogenesis to postocculsive hindlimb perfusion in mice" J Mol Cell Cardiol 34, 775-787.

Schwartz et al., 2002, Multipotent adult progenitor cells from bone marrow differentiate into functional hepatocyte-like cells J Clin Invest 109:1291-302.

Schwartzmann, M. (2000) "Use of collagen membranes for guided bone regeneration: a review" Implant Dent 9(1): 63-6.

Schweitzer, C.M., Van Der, Schoot, Ce, Drager, A.M., Van der Valk, P., Zevenbergen, A., Hooibrink, B., Westra, A.H., and Langenhuijsen, M.M. (1995) "Isolation and culture of human bone marrow endothelial cells" Exp Hematol 23, 41-8.

Sclafani, A.P. and T. Romo, 3rd (2001) "Collagen, human collagen and fat: the search for a three-dimensional soft tissue filler" Facial Plast Surg 17(1): 79-85.

Sclafani, A.P., T. Romo, 3rd et al. (2002) "Rejuvenation of the aging lip with an injectable acellular dermal graft (cymetra)" Arch Facial Plast Surg 4(4): 252-7.

Scott, Douglas M. et al., "Collagen Synthesis in Cultured Osteoblast-like Cells," *Archives of Biochemistry and Biophysics*, 1980, 201:384-91.

Seale and Rudnicki 2000 *Dev. Biol.* "A New Look at the Origin, Function, and "Stem-Cell" Status of Muscle Satellite Cells," 218:115-124.

Sekiya, I., Larson, B.L., Smith, J.R., Pochampally, R., Cui, J.G., and Prockop, D.J. (2002) "Expansion of human adult stem cells from bone marrow stroma: conditions that maximize the yields of early progenitors and evaluate their quality" Stem Cells 20, 530-541.

Sergeant, P., Blackstone, E., and Meyns, B. (1997) "Early and late outcome after CABG in patients with evolving myocardial infarction" Eur J Cardiothorac. Surg 11, 848-856.

Shalhoub, Victoria et al., "Downregulation of Cell Growth and Cell Cycle Regulated Genes during Chick Osteoblast Differentiation with the Reciprocal Expression of Histone Gene Variants," *Biochemistry*, 1989, 28:5318-22.

Shi, Q., S. Rafil, et al. (1998) "Evidence for circulating bone marrow-derived endothelial cells" Blood 92(2): 362-7.

Shigematsu, S., Yamauchi, K., Nakajima, K., Iijima, S., Aizawa, T., and Hashizume, K. (1999) "IGF-1 regulates migration and angiogenesis of human endothelial cells" Endocr. J 46 Suppl, S59-S62.

Shillabeer, et al., "A novel method for studying preadipocyte differentiation in vitro," *Intl. J. Obesity* 1996 20(Supp. 3), S77-S83.

Shore, J.W. (2000) "Injectable lyophilized particulate human fascia lata (Fascian) for lip, perioral and glabellar enhancement" Opthal Plast Reconstr Surg 16(1): 23-7.

Shukunami C., et. al., 1996 *Journ. Of Cell Bio.* "Chondrogenic Differentiation of Clonal Mouse Embryonic Cell Line ATDC5 In Vitro: Differentiation-dependent Gene Expression of Parathyroid Hormone (PTH)/PTH-related Peptide Receptor," 133:2:457-468.

Shukunami, C., et al., 1998 *Exp. Cell Res.* "Sequential Progression of the Differentiation Program by Bone Morphogenetic Protein-2 in Chondrogenic Cell Line ATDC5," 241:1-11.

(56) References Cited

OTHER PUBLICATIONS

Siffert, Robert S., "The Role of Alkaline Phosphatase in Osteogenesis," *The Journal of Experimental Medicine*, 1951, 93:415-26.
Silberstein, L., et al., 1986 *Cell* "Developmental Progression of Myosin Gene Expression in Cultured Muscle Cells," 46:1075-1081.
Silver, F.H. and G. Pins (1992) "Cell growth on collagen: a review of tissue engineering using scaffolds containing extracellular matrix" J Long Term Eff Med Implants 2(1): 67-80.
Sivan-Loukianova et al. "CD34+ Blood cells accelerate vascularization and healing of diabetic mouse skin wounds" J. Vascular Research, vol. 40, No. 4, 368-377 (Jul.-Aug. 2003).
Šmahel, J., "Aspiration lipectomy and adipose tissue injection: pathophysiologic commentary," *European Journal of Plastic Surgery*, 14:126-31, 1991.
Smith et al., 2000, "Mesenchymal Stem Cells Derived From Bone Marrow and Human Adipose Tissue Exhibit Multilineage Potential," *Journal of Investigative Medicine*, 95A.
Smith, J.W. (1997) "Apheresis techniques and cellular immunomodulation" Ther. Apher. 1, 203-206.
Smith et al., 1995, A mononuclear cell dose of 3×10(8)/kg predicts early multilineage recovery in patients with malignant lymphoma treated with carmustine, etoposide, Ara-C and melphalan (BEAM) and peripheral blood progenitor cell transplantation, Exp Hematol 23:1581-1588.
Smits, G., Holzgreve, W., and Hahn, S. (2000) "An examination of different Percoll density gradients and magnetic activated cell sorting (MACS) for the enrichment of fetal erythroblasts from maternal blood" Arch. Cynecol. Obstet. 263, 160-163.
Soda, et al., 1983, "Adipocyte stem cell: A brief review," *Int. J. of Cell Cloning*, 1:79-84.
Sodian, R., Lemke, T., Fritsche, C., Hoerstrup, S.P, Fu, P., Potapov, E.V., Hausmann, H., and Hetzer, R. (2002) "Tissue-engineering bioreactors: a new combined cell-seeding and perfusion system for vascular tissue engineering" Tissue Eng 8, 863-870.
Soli et al., 2001, A multicentre evaluation of a new filtration protocol for leucocyte depletion of high-haematocrit red blood cells collected by an utomated blood collection system, Vox Sang. 81:108-112.
Sommer et al. "Current Concepts of Fat Graft Survival: Histology of Aspirated Adipose Tissue and Review of the Literature." Dermatologic Surgery. 26(12):1159-1166 (2000).
Sorisky et al., "From preadipocyte to Adipocyte: Differentiation-Directed Signals of Insulin from the Cell Surface to the Nucleus," *Critical Review in Clinical Laboratory Sciences* 1999 36(1), 1-34.
Speranza, M.L. and G. Valentini (1986) "A simple procedure for the purification of neutral salt soluble type I collagen from skin" Ital J Biochem 35(1): 42-8.
Springhorn, Jeremy P. et al., "Human Capillary Endothelial Cells from Abdominal Wall Adipose Tissue: Isolation Using an Anti-Pecam Antibody," *In Vitro Cellular & Developmental Biology-Animal*, 31:473-81, 1995.
Stamm, C., Westphal, B., Kleine, H.D., Petzsch, M., Kittner, C., Klinge, H., Schumichen, C., Nienaber, C.A., Freund, M. and Steinhoffm G. (2003) "Autologous bone-marrow stem-cell transplantation for myocardial regeneration" Lancet 4, 45-46.
Stashower et al., 1999, "Stromal progenitor cells present within liposuction and reduction abdominoplasty fat for autologous transfer to aged skin," *Dermatologic Surgery*, 25:12:945-949.
Stosich et al. "Adipose tissue engineering from human adult stem cells: clinical implications in plastic and reconstructive surgery." *Plast Reconstr Surg* 119, 71-83 (2007).
Strauer, B.E., M. Brehm, et al. (2002) "Repair of infarcted myocardium by autologous intracoronary mononuclear bone marrow cell transplantation in humans" Circulation 106(15): 1913-8.
Strutt et al., 1996, "Growth and differentiation of human adipose stromal cells in culture," *methods in Molecular Medicine: Human Cell Culture Protools*, 41-51.
Su et al., "Increased expression of G in mouse embryo stem cells promotes terminal differentiation to adipocytes," *American Physiological Society* 1993 265(6), C1729-C1735.

Suga, S., et al., 1996,"*Eur. J. Cell Biol.* "Intracellular localization of antigens recognized by anti-vimentin monoclonal antibodies (mAbs): Cross-reactivities of anti-vimentin mAbs with other cellular components 70:84-91.
Sundberg et al., 2002, Stable expression of antiopoietin-1 and other markers by cultured pericytes: phenotypic similarities to a subpopulation of cells in maturing vessels during later stages of angiogenesis in vivo, Lab invest 82:387-401.
Syrjälä, M. et al., "A flow cytometric assay of CD34-postitive cell populations in the bone marrow," *British Journal of Haematology*, 1994, 88:679-84.
Tabata,Y. et al. "De novo formation of adipose tissue by controlled release of basic fibroblast growth factor." *Tissue Eng.* 6:6279-289 (2000).
Tacchetti, C, et al., 1992 *Exp Cell Res.* "Cell Condensation in Chondrogenic Differentiation," 200:26-33.
Tacchetti, C. et al., "In Vitro Morphogenesis of Chick Embryo Hypertrophic Cartilage," *The Journal of Cell Biology*, 1987, 105:999-1006.
Takahashi, T., C. Kalka, et al. (1999) "Ischemia and cytokine-induced mobilization of bone marrow-derived endothelial progentiro cells for neovascularization" Nat Med 5(4): 434-8.
Takasaki, et al (1995) "Human type VI collagen: purification from human subcutaneous fat tissue and an immunohistochemical study of morphea and systemic sclerosis" J Dermatol 22(7): 480-5.
Tapscott, et al., 1988 *Science* "MyoD1: A Nuclear Phosphoprotein Requiring a Myc Homology Region to Convert Fibroblasts to Myoblasts," 242:405-411.
Tavassoli et al., 1981, "The Nature of Fibroblasts Derived From Adipose Tissue In-Vitro," *Clinical Research*, 29:5:871A.
Tavassoli, Mehdi, "In Vivo Development of Adipose Tissue Following Implantation of Lipid-Depleted Cultured Adipocyte," *Experimental Cell Research*, 137:55-62, 1982.
Thomas, E.D. (1994) "Stem Cell Transplantation: Past, Present and Future" Stem Cells 12: 539-544.
Thornell, et al., 1984 *J. Neurol. Sci.* "Development of Fiber Types in Human Fetal Muscle," 66:107-115.
Toma, J.G., Akhavan, M., Fernandes, K.J., Barnabe-Heider, F., Sadikot, A., Kaplan, D.R. and Miller, F.D. (2001) "Isolation of multipotent adult stem cells from the dermis of mammalian skin" Nat Cell Biol 3, 778-84.2.
Tontonoz, Peter et al., "mPPARg2: tissue-specific regulator of an adipocyte enhancer," *Genes & Development*, 1994, 8:1224-34.
Torio-Padron et al. "Engineering of adipose tissue by injection of human preadipocytes in fibrin." *Aesthetic Plast Surg* 31, 285-293 $(2007)_3$.
Tosh, et al. "Conversion of pancreatic cells to hepatocytes." Biochem Soc Trans 30:51-55 (2002).
Totonoz, et al., 1995 *Nucl. Acid Res* "mPPARg2: tissue-specific regulator of an adipocyte enhancer.".
Trayhurn, P. and Margaret Ashwell, "Control of white and brown adipose tissues by the autonomic nervous system," *The Proceedings of the Nutrition Society*, 1987, 46:135-42.
Tsonis and Goetinck 1990 *Exp. Cell Res.* "Cell Density Dependent Effect of a Tumor Promoter on Proliferation and Chondrogenesis of Limb Bud Mesenchymal Cells," 190:247-253.
Twentyman, P.R. and Yuhas, J.M. (1980) "Use of bacterial neutral protease for disaggregation of mouse tumours and multicellular tumor spheroids" Cancer Lett 9, 225-8.
Uitto, J. (1971) "Collagen biosynthesis in human skin. A review with emphasis on scleroderma" Ann Clin Res 3(5): 250-8.
Urban, et al. "Degeneration of the intervertebral disc." Arthritis Research & Therapy. 5(3):120-130 (2003).
Urbich et al. "Endothelial Progenitor Cells." Trends in Cardiovascular Medicine. 14(8):318-322 (2004).
Van et al., 1978, "Complete Differentiation of Adipocyte Precursors," *Cell Tissue*, 195:317-329.
Van Merris, V., Meyer, E., Dosogne, H., and Burvenich, C. (2001) "Separation of bovine bone marrow into maturation-related myeloid cell fractions" Vet. Immunol. Immunopathol. 83, 11-17.

(56) References Cited

OTHER PUBLICATIONS

Vandenburgh, Herman H. and Patricia Karlisch, "Longitudinal Growth of Skeletal Myotubes In Vitro in a New Horizontal Mechanical Cell Stimulator," *In Vitro Cellular & Developmental Biology*, 1989, 25:607-16.
Varzaneh et al., 1994, Extracellular Matrix Components Secreted by Microvascular Endothelial Cells Stimulate Preadipocyte Differentiation In Vitro, Metabolism 43(7):906-912.
von der Mark, et al., 1977 *Nature* "Relationship between cell shape and type of collagen synthesised as chondrocytes lose their cartilage phenotype in culture," 267:531-532.
von Heimburg, D. et al. "Human preadipocytes seeded on freeze-dried collagen scaffolds investigated in vitro and in vivo." *Biomaterials* 22, 429-38 (2001).
Vukicevic et al., 1992, Identification of Multiple Active Growth factors in Basement Membrane Matrigel Suggests Caution in Interpretation of Cellular Activity Related to Extracellular Matrix Components, Exp. Cell Res, 202(1):1-8.
Wabitsch, et al., "Biological Effects of Human Growth Hormone in Rat Adipocyte Precursor Cells and Newly Differentiated Adipocytes in primary Culture," *Metabolism* 1996 vol. 45,No. 1 pp. 34-42.
Wakitani, Shigeyuki et al., "Mesenchymal Cell-Based Repair of Large, Full-Thickness Defects of Articular Cartilage," *The Journal of Bone and Joint Surgery*, 1994, 76A:579-92.
Wakitani, Shigeyuki et al., "Myogenic Cells Derived from Rat Bone Marrow Mesenchymal Stem Cells Exposed to 5-Azacytidine," *Muscle & Nerve*, 1995, 18:1417-26.
Walther, W. and Stein, U. (2000) Viral vectors for gene transfer: a review of their use in the treatment of human diseases: Drugs 609, 249-71.
Walton et al. "De novo adipose formation in a vascularized engineered construct." *Microsurgery* 24, 378-384 (2004).
Wang, L., Zeng, H., Wang, P., Soker, S., and Mukhopadhyay, D. (2003) "Neuropilin-1 mediated vascular permeability factor/vascular endothelial growth factor-dependent endothelial cell migration" J Biol Chem 278, 48848-48860.
Watts et al., 2002, Variable product purity and functional capacity after CD34 selection: a direct comparison of the CliniMACS (v2.1) and Isolex 300i(v2.5) clinical scale devices, Br J Haematol 118:117-23.
Weiner, Francis R. et al. "Regulation of collagen Gene Expression in 3T3-L1 Cells. Effects of Adipocyte Differentiation and Tumor necrosis Factor a," Biochem 1989 28:4094-4099.
Weintraub, et al., 1991 *Science* "The *myo*D Gene Family: Nodal Point During Specification of the Muscle Cell Lineage," 251:761-766.
Weintraub, Harold et al. "Tissue-specific gene activation by MyoD: determination of specificity by *cis*-acting repression elements," *Genes & Development*, 1994, 8:2203-11.
Werlich, T., K.J. Stiller, et al. (1999) "Experimental studies on the stem cell concept of liver regeneration II" Exp Toxicol Pathol 51(1): 93-8.
Williams, Irene H. and S. Efthimios Polakis, "Differentiation of 3T3-L1 Fibroblasts to Adipocytes, the Effect of Indomethacin, Prostaglandin $E_1$ and Cyclic AMP on the Process of Differentiation" *Biochem Biophys. Res.Commun.* 1977 77:175-186.
Williams, John T. et al., "Cells Isolated from Adult Human Skeletal Muscle Capable of Differentiating into Multiple Mesodermal Phenotypes," *The American Surgeon*, 65:22-6, 1999.
Williams, S.K., McKenney, S. and Jarrell, B.E. (1995) "Collagenase lot selection and purification for adipose tissue digestion" Cell Transplant 4, 281-9.
Williams, Stuart K. et al., "Liposuction-derived human fat used for vascular graft sodding contains endothelial cells and not mesothelial cells as the major cell type," *Journal of Vascular Surgery*, 19:916-23, 1994.
Wise, Leigh S. and Howard Green, "Participation of One Isozyme of Cytosolic Glycerophosphate Dehydrogenase in the Adipose Conversion of 3T3 Cells," *J. Biol. Chem.* 1979 254:273-275.

Wtodarski, Krzysztof H., "Section III. Basic Science and Pathology. Properties and Origin of Osteoblasts," *Clinical Orthopaedics and Related Research*, 252:276-93, 1990.
Wollert et al. "Intracoronary autologous bone-marrow cell transfer after myocardial infarction: the BOOST randomised controlled clinical trial." The Lancet Limited. 364(9429):141-148 (2004).
Wu et al. "Preparation and assessment of glutaraldehyde-crosslinked collagen-chitosan hydrogels for adipose tissue engineering." *J Biomed Mater Res A* 81, 59-65 (2007).
Xiong, B., Gong, L.L., Zhang, F., Hu, M.B. and Yuan, H.Y. (2002) "TGF betal expression and angiogenesis in colorectal cancer tissue" World J Gastroenterol. 8, 496-498.
Yavorkovsky, L., E. Lai, et al. (1995) "Participation of small intraportal stem cells in the restitutive response of the liver to periportal necrosis induced by allyl alochol" Hepatology 21(6): 1702-12.
Ye, Q., Zund, G., Benedikt, P., Jockenhoevel, S., Hoerstrup, S.P., Sakyama, S., Hubbell, J.A. and Turina, M. (2000) "Fibrin gel a three dimensional matrix in cardiovascular tissue engineering" Eur J Cardiothorac Surg 17, 587-91.
Yin, L., D. Lynch, et al. (1999) "Participation of different cell types in the restitutive response of the rat liver to periportal injury induced by allyl alcohol" J Hepatol 31(3): 497-507.
Yokoyama, T., N. Yoshimural et al (2001) "Persistence and survival of autologous muscle derived cells versus bovine collagen as potential treatment of stress urinary incontinence" J Urol 165(1): 271-6.
Yoo, Jung U. and Brian Johnstone, "The Role of Osteochondral Progenitor Cells in Fracture Repair," *Clinical Orthopaedics and Related Research*, 1998, 355S:S73-81 ).
Yoon, Kyonggeun et al., "Characterization of the Rat osteocalcin Gene: Stimulation of Promoter Activity by 1,25-Dihydroxyvitamin D3," *Biochem.* 1988 27:8521-8526.
Young et al., "Mesenchymal Stem Cells Reside Within the Connective Tissues of Many Organs," *Developmental Dynamics* 1995 202(2), 137-144.
Young, "A Time for Restraint", 2000 Science 287:1424.
Young et al., 2001, Human reserve pluripotent mesenchymal stem cells are present in the connective tissues of skeletal muscle and dermis derived from fetal, adult and geriatric donors, Anat Rec 264:51-62.
Young, Henry E. et al., "Human Pluripotent and Progenitor Cells Display Cell Surface Cluster Differentiation Markers CD10, CD13, CD56, and MHC Class-I," *Proc. Soc. Exp. Biol. Med.*, 1999, 221:63-71.
Zalin, Rj 1987 *Exp. Cell Res.* "The Role of Hormones and Prostanoids in the in Vitro Proliferation and differentiation of Human Myoblasts," 172:265-281.
Zezulak, Kathleen M. and Howard Green, "Specificity of Gene Expression in Adipocytes," *Molecular and Cellular Biology*, 1985, 5:419-21.
Zimmerman, W.H., Diddie, N., Wasmeier, G.H. Nixdorff, U., Hess, A., Meinychenko, I., Boy, O., Neuhuber, W.L., Weyand, M., and Eschenhagen, T. (2002) "Cardiac grafting of engineered heart tissue in syngenic rats" Circulation 106, 1151-1157.
Zimmermann, W.H., Melnychenko, I., and Eschenhagen, T. (2004) "Engineered heart tisue for regeneration of diseased hearts" Biomaterials 25, 1639-1647.
Zuk, Patricia A. et al., "Human Adipose Tissue is a Source of Multipotent Stem Cells," *Molecular Biology of the Cell*, 2002, 13:4279-4295.
Zuk, Patricia Z. et al., "Multilineage Cells from Human Adipose Tissue: Implication for Cell-Based Therapies," *Tissue Engineering*, Apr. 2001, 7:211-28.
Zvaifler, et al., 2000, "Mesenchymal precursor cells in the blood of normal individuals," *Arthritis Res.* 2:477-488.
Supplemental European Search Report for European Patent Application No. EP 02805648 dated Sep. 5, 2006.
International Search Report for International Patent Application No. PCT/US02/29207 dated Dec. 17, 2002.
International Search Report for International Patent Application No. PCT/US02/39465 dated Jun. 22, 2006.
International Search Report for International Patent Application No. PCT/US02/40921dated Jul. 30, 2003.

(56) References Cited

OTHER PUBLICATIONS

International Search Report for International Patent Application No. PCT/US04/20594 dated Apr. 6, 2005.
International Search Report for International Patent Application No. PCT/USO4/21391 dated Apr. 4, 2005.
International Preliminary Report on Patentability for PCT/US04/21415 dated Jan. 18, 2007, containing Written Opinion dated Dec. 30, 2005.
International Search Report for International Patent Application No. PCT/US04/21417 dated Apr. 12, 2005.
International Search Report for International Patent Application No. PCT/US04/21418 dated Dec. 22, 2005.
International Search Report for International Patent Application No. PCT/US04/21480 dated Apr. 4, 2005.
International Preliminary Report on Patentability for International Patent Application No. PCT/US04/21483 dated Jan. 18, 2007, containing Written Opinion dated Apr. 13, 2006.
International Preliminary Report on Patentability for International Patent Application No. PCT/US04/21549 dated Jan. 18, 2007, containing Written Opinion dated Feb. 7, 2006.
International Search Report for International Patent Application No. PCT/US2004/005117 dated Apr. 6, 2006.
Supplemental Partial European Search Report for European Patent Application No. 2805565.5 dated Mar. 6, 2007.
Supplemental European Search Report for European Patent Application No. 4777155.5 dated Aug. 4, 2006.
Examination Report for European Patent Application No. 4756641.9 dated Jan. 19, 2007.
Supplemental European Search Report for European Patent Application No. 4756641.9 dated Oct. 18, 2006.
International Search Report for International Patent Application No. PCT/US2006/021017 dated Oct. 20, 2006.
International Search Report for International Patent Application No. PCT/US2006/040221 dated Feb. 27, 2007.
International Search Report for International Patent Application No. PCT/US2005/001267 dated Apr. 28, 2006.
Supplemental Partial European Search Report for European Patent Application No. 04777586.1 dated Jun. 5, 2007.
Supplemental European Search Report for European Patent Application No. 2805565.5 dated Jul. 4, 2007.
International Search Report for International Patent Application No. PCT/US2005/046296 dated Jun. 26, 2007.
Supplemental European Search Report for European Patent Application No. 4777586.1 dated Aug. 3, 2007.
Supplemental European Search Report for European Patent Application No. 04713403.6 dated Jul. 30, 2007.
Supplemental European Search Report for European Patent Application No. 04756623.7 dated Oct. 10, 2007.
Supplemental European Search Report for European Patent Application No. 04756607.0 dated Nov. 14, 2007.
European Search Report for European Application No. 07124088.1 dated Apr. 25, 2008.
International Search Report for International Application No. PCT/US05/18605 dated Jul. 3, 2008.
International Search Report for International Application No. PCT/US04/21419 dated Jul. 3, 2008.
Supplemental European Search Report for European Application No. 04777546.5 dated Jun. 10, 2009.
Supplemental European Search Report for European Application No. 04756626.0 dated Sep. 2, 2009.
Supplemental European Search Report for European Application No. 04776784.3 dated Nov. 5, 2009.
Supplemental European Search Report for European Application No. 05754073.4 dated Aug. 7, 2009.
Partial European Search Report for European Application No. 10183850.6 dated Jun. 17, 2011.
Extended European Search Report for European Application No. 10184623.6 dated May 26, 2011.
Extended European Search Report for European Application No. 10183690.6 dated Aug. 22, 2011.
Extended European Search Report for European Application No. 10183737.5 dated Aug. 22, 2011.
Anderson, Apr. 30, 1998, Human Gene Therapy, Nature, 392 Supp (6679):25-30.
Arts et al., 2002, Contaminants from the Transplant Contribute to Intimal Hyperplasia Associated with Microvascular Endothelial Cell Seeding, Eur. J. Endovasc. Surg. 23:29-38.
Banerji et al., Feb. 22, 1999, LYVE-1, a New Homologue of the CD44 Glycoprotein, is a Lymph-specific Receptor for Hyaluronan, J. Cell Biology, 144(4):789-801.
Baron et al., 1999, Acute Necrotizing Pancreatitis, The New Engl. J. Med. 340:1412-1417.
Bender et al., 1991, Identification and comparison of CD34-positive cells and their subpopulations from normal peripheral blood and bone marrow using multicolor flow cytometry, Blood 77(12): 2591-2596.
Bergan et al., 1996, Blood, 88(2):731-741.
Berry et al., 2005, The Establishment of a Predictive Mutational Model of the Forkhead Domain through the Analyses of FOXC2 Missense Mutations Identified in Patients with Hereditary Lymphedema with Distichiasis, Human Molecular Genetics 14(18):2619-2627.
Bjorntorp et al., 1980, Differentiation and function of rat adipocyte precursor cells in primary culture, J. Lipid Research 21:714-723.
Boghossian et al, 2005, Suppression of fat deposition for the life time with gene therapy, Peptides 26(8):1512-1519.
Breiteneder-Geleff et al., Feb. 1999, Angiosarcomas Express Mixed Endothelial Phenotypes of Blood and Lymphatic Capillaries, Am. J. Path. 154(2): 385-394.
Cavallini, 2007, Autologous Fibroblasts to Treat Deep and Complicated Leg Ulcers in Diabetic Patients, Wound Repair Regen. 15(1):35-8.
Chang et al., Jan. 2006, Characterization of two populations of mesenchymal progenitor cells in umbilical cord blood, Cell Biology International, 40:495-499.
Chen et al., Dec. 2005, Novel Expression and Characterization of Lymphatic Vessel Endothelial Hyaluronate Receptor 1 (LYVE-1) by Conjunctival Cells, Invest. Ophthalmol. Vis. Sci. 46(12):4536-4540.
Colombo et al., Feb. 7, 2003, Opposite effects of background genotype on muscle and liver insulin sensitivity of lipoatrophic mice, J Biol Chern. 278(6):3992-3999.
Cousin, et al. (2003), "Reconstitution of Lethally Irradiated Mice by Cells Isolated From Adipose Tissue", Biochem. Biomed. Res. Comm. 310:1016-1022.
Dawra et al., Apr. 2007, Development of a new mouse model of acute pancreatitis induced by administration of L-arginine, Am J Physiol Gastrointest Liver Physiol. 292(4):G1009-1018.
de la Fuente et al., 2004, Dedifferentiated adult articular chondrocytes: a population of human multipotent primitive cells, Exp. Cell Res. 297(2): 313-28.
De Ugarte, "Comparison of Multi-Lineage Cells from Human Adipose Tissue and Bone Marrow," Cells Tissues Organs, 2003.
De Ugarte et al., 2003, Differential expression of stem cell mobilization-associated molecules on multi-lineage cells from adipose tissue and bone marrow, Immunology Letters, 89:267-270.
Dragoo et al., 2003, Bone induction by BMP-2 transduced stem cells derived from human fat, J. Orth. Res., 21:622-629.
Duan, "Treatment of Myocardial Ischemia with Bone Marrow-Derived Mesenchymal Stem Cells Overexpressing Hepatocyte Growth Factor," Molecular Therapy, 2003.
Duxbury et al., 2004, Lymphangiogenesis in tissue-engineered small intestine, Transplantation 77(8):1162-6.
El-Ghalbzouri et al., 2004, Cutaneous biology: human adipose tissue-derived cells delay re-epithelialization in comparison with skin fibroblasts in organotypic skin culture, British Journal of Dermatology, 150(3):444-454.
Fraser et al., Mar. 1992, Proliferation of totipotent hematopoietic stem cells in vitro with retention of long-term competitive in vivo reconstituting ability, Cell Biology, 89(5):1968-72.
Friedmann, 1989, Progress toward human gene therapy, Science, 244(4910):1275-1281.
Fukumura, "Adipogenesis paracrine regulation of angiogenesis and adipocyte differentiation during in vivo," Circ Res. 2003.

(56) References Cited

OTHER PUBLICATIONS

Fukuda, et al. (2006), "Stem Cells as a Source of Regenerative Cardiomyocytes", Circ. Res. 98:1002-1013.
Garrafa et al., 2006, Isolation and characterization of lymphatic microvascular endothelial cells from human tonsils, J Cell Physiol 207(1):107-113.
Gelse et al., Feb. 2003, Articular cartilage repair by gene therapy using growth factor-producing mesenchymal cells, Arthritis Rheum. 48:430-441.
Goldman et al., 2005, Overexpression of VEGF-C causes transient lymphatic hyperplasia but not increased lymphangiogenesis in regenerating skin, Circ. Res. 96(11):1193-1199.
Harvey et al., 2005, Lymphatic Vascular Defects Promoted by *Prox1* Haploinsufficiency Cause Adult-Onset Obesity, Nature Genetics 37[10]:1072-1081.
Hausman et al., 2001, The biology of white adipocyte proliferation, Obesity Reviews, 2(4):239-254.
Hausman et al., 2004, Adipose tissue angiogenesis, Journal of Animal Science 82:925-934.
Hess, "Bone Marrow as a Source of Endothelial Cells an NeuN-Expressing Cells After Stroke," Stroke, 2002.
Hewitson et al., 2006, Histochemical localization of cell proliferation using in situ hybridization for histone mRNA, Methods Mol. Biol. 326:219-26.
Houtgraff, et al. (2011), "First Experience in Humans Using Adipose-Derived Regenerative Cells in the Treatment of Patents With STSegment Elevation Myocardial infarction", J. Am. Coll. Cardiol. 59:539-540.
Huard et al, 2002, Muscle-derived cell-mediated ex vivo gene therapy for urological dysfunction, Gene Therapy, 9:1617-1626.
Ito et al., 2001, A new continuous-flow cell separation method based on cell density: principle, apparatus, and preliminary application to separation of human buffy coat, Journal of Clinical Apheresis, 16(4):186-191.
Ji, 2006, Lymphatic Endothelial Cells, Lymphangiogenesis, and Extracellular Matrix, Lymphat. Res. Biol. 4(2):83-100.
Karkkainen et al., 2002, Lymphatic endothelial regulation, lymphoedema, and lymph node metastasis, Semin Cell Dev Biol 13(1):9-18.
Katz et al. 2005, Cell surface and transcriptional characterization of human adipose-derived adherent stromal (hADAS) cells, Stem Cells 23(3):412-23.
Kerjaschki et al., 2006, Lymphatic endothelial progenitor cells contribute to de novo lymphangiogenesis in human renal transplants, Nature Medicine 12(2):230-4.
Kim et al., 2002, Ex vivo gene delivery of IL-1Ra and soluble TNF receptor confers a distal synergistic therapeutic effect in antigen-induced arthritis, Mol. Ther. 6:591-600.
Klar et al., 2005, RAR-related orphan receptor a isoform 1 (RORa1) is disrupted by a balanced translocation t(4;15)(q22.3;121.3) associated with severe obesity, Eur. J. Hum. Genet. 13(8):928-934.
Klein et al., 2006, Adipose tissue as source and target for novel therapies, Trends Endocrin. Metab., 17(1):26-32.
Kong et al., 2005, Effect of cardiac lymph flow obstruction on cardiac collagen synthesis and interstitial fibrosis, Physiol Res. 55:253-258.
Kriehuber et al., 2001, Isolation and characterization of dermal lymphatic and blood endothelial cells reveal stable and functionally specialized cell lineages, J Exp Med 194(6):797-808.
Lambert et al., 1993, Local drug delivery catheters: functional comparison of porous and microporous designs, Coron. Artery Dis. 4:469-475.
Lee et al., Jan. 2006, Human adipose-derived stem cells display myogenic potential and perturbed function in hypoxic conditions, Biochemical and Biophysical Research Communications, 341:882-888.
Leo et al., 2004, In vivo bioluminescent imaging of virus-mediated gene transfer and transduced cell transplantation in the interverebral disc, Spine, 29(8):838-844.
Lincoff et al., 1994, Local drug delivery for the prevention of restenosis. Fact, fancy, and future, Circulation, 90:2070-2084.

Maruyama et al., Apr. 2007, Decreased Macrophage Number and Activation Lead to Reduced Lymphatic Vessel Formation and Contribute to Impaired Diabetic Wound Healing, Am J Pathol. 170(4):1178-1191.
Massi et al., 2006, Tumour lymphangiogenesis is a possible predictor of sentinel lymph node status in cutaneous melanoma: a case-control study, J Clin Pathol, 59(2):166-173.
Mazo et al. (2008), "Transplantation of Adipose-Derived Stromal Cells is Associated With Functional Improvement in a Rat Model of Chronic Myocardial Infarction", Eur. J. Heart Failure 10:454-462.
Mazur et al., 1994, Coronary restenosis and gene therapy, Texas Heart Institute Journal, 21:104-111.
McMurray, Jan. 21, 2010, Systolic heart failure, The New England Journal of Medicine, 362(3):228-238, Supplementary Appendix.
Mehlhorn et al., 2001, Myocardial Fluid Balance, Eur. J. Cardiothoracic Surg. 20:1220-1230.
Miller, 1992, Human gene therapy comes of age, Nature, 357:455-460.
Moitra et al., 1998, Life without white fat: a transgenic mouse, Genes Dev. 12(20):3168-3181.
Muskhelishvili et al., 2003, Evaluation of cell proliferation in rat tissues with BrdU, PCNA, Ki-67(MIB-5) immunohistochemistry and in situ hybridization for histone mRNA, J. Histochem. & Cytochem. 51(12):1681-1688.
Ng et al., Nov. 2004, Interstitial flow differentially stimulates blood and lymphatic endothelial cell morphogenesis in vitro, Microvasc Res. 68(3):258-64.
Ogawa, 2006, The importance of adipose-derived stem cells and vascularized tissue regeneration in the field of tissue transplantation, Current Stem Cell Research & Therapy, 1:13-20.
Orlic, "Bone marrow stem cells regenerate infarcted myocardium," Pediatric Transplantation, 2003.
Orlic, "Stem Cell Repair in Ischemic Heart Disease: An Experimental Model," International Journal of Hematology, Supplement I, 2002.
Pajvani et al., 2005, Fat apoptosis through targeted activation of caspase 8: a new mouse model of inducible and reversible lipoatrophy, Nature Medicine, 11(7):797-803.
Patrick et al., 2000, Adipose tissue engineering: the future of breast and soft tissue reconstruction following tumor resection, Semin. Surg. Oncol. 19(3):302-11.
Pavcnik et al., 2004, Second-generation percutaneous bioprosthetic valve: a short-term study in sheep, Eur. J. Endovasc. Surg. 40:1223-1227.
Perbeck et al., Mar. 2006, Lymph Circulation in the Breast after Radiotherapy and Breast Conservation, Lymphology, 39(1):33-40 (abstract).
Podgrabinska et al., Dec. 10, 2002, Molecular characterization of lymphatic endothelial cells, PNAS 99(25):16069-16074.
Ponce, 2001, 14. In vitro Matrigel Angiogenesis Assays, in Methods in Molecular Medicine, vol. 46: Angiogenesis Protocols, Edited by JC Murray, Humana Press, Totowa, NJ, pp. 205-209.
Ramirez-Zacarias et al., 1992, Quantitation of adipose conversion and triglycerides by staining intracytoplasmic lipds with Oil red O, Histochemistry 97(6):493-497.
Reitman et al., 2000, A-ZIP/F-1 mice lacking white fat: a model for understanging lipoatrophic diabetes, Int. J. Obes. Relat. Metab. Disord. 24 (Suppl4):S11-S14.
Religa et al., 2005, Presence of bone marrow-derived circulating progenitor endothelial cells in the newly formed lymphatic vessels, Blood 106(13):4184-4190.
Rim et al., 2005, Mesenchymal stem cells from the outer ear: a novel adult stem cell model system for the study of adipogenesis, FASEB J. 19(9):1205-1207.
Rupnick et al., 2002, Adipose tissue mass can be regulated through the vasculature, PNAS 99(16):10730-10735.
Ryden et al., Jan. 11, 2002, Mapping of early signaling events in tumor necrosis factor-alpha-mediated lipolysis in human fat cells, J. Biol. Chem. 277(2):1085-1091.
Sallam et al., 1973, A new surgical approach to myocardial revascularization-internal mammary artery to coronary vein anastomosis, Thorax, 28:613-616.

(56) References Cited

OTHER PUBLICATIONS

Saluja et al., Mar. 2003, Pancreatitis and associated lung injury: when MIF miffs, Gastroenterology, 124(3):844-847.
Salven et al., 2003, VEHFR-3 and CD133 identify a population of CD34+ lymphatic/vascular endothelial precursor cells, Blood 101(1):168-172.
Schenke-Layland et al., May 15, 2009, Adipose tissue-derived cells improve cardiac function following myocardial infarction, Journal of Surgical Research, 153(2):217-223.
Schmidt et al., Jan. 1992, A better model of acute pancreatitis for evaluating therapy, Ann Surg. 215(1):44-56.
Sekiya et al., 2004, Adipogenic differentiation of human adult stem cells from bone marrow stroma (MSCs), J. Bone and Min. Res. 19(2):256-264.
Strem et al., 2005, Multipotential differentian of adipose tissue-derived stem cells, Keio J. Med 54(3):132-141.
Symmons et al., 2006, The world of biologics, Lupus, 15(3):122-126.
Tafech et al., 2006, Destroying RNA as a Therapeutic Approach, Current Medicinal Chemistry, 13(8):863-81.
Tang et al., 2004, Commitment of C3H10T1/2 pluripotent stem cells to the adipocyte lineage, PNAS 101(26):9607-9611.
Tintut et al., 2003, Multilineage potential of cells from the artery wall, Circulation, 108(20):2505-2510.
Trujillo et al., 2005, Apoptosis through targeted activation of Caspase8 ("ATTAC-mice"): novel mouse models of inducible and reversible tissue ablation, Cell Cycle 4(9):1141-1145.
Urs et al., 2004, Gene expression profiling in human preadipocytes and adipocytes by microarray analysis, J. Nutr. 134:762-770.
Van, "Cytological and enzymological characterization of adult human adipocyte precursors in culture," J Clin Invest 1976.
Vassaux et al., 1994, Proliferation and differentiation of rat adipose precursor cells in chemically defined medium: differential action of anti-adipogenic agents, Journal of Cellular Physiology, 161(2):249-256.
Verma (1990), "Gene therapy." Scientific American 263(5): 68-84.
Vojtassak, et al., 2006; "Autologous Biograft and Mesenchymal Stem Cells in Treatment of the Diabetic Foot," Neuro Endocrinol Lett. 27 Suppl 2:134-7.
Wagner et al., 2005, Comparative characteristics of mesenchymal stem cells from human bone marrow, adipose tissue, and umbilical cord blood, Experimental Hematology 33:1402-1416.
Wang "Human Progenitor cells from bone marrow or adipose tissue produce VEGF, HGF, and IGF-1 in response to TNF by a p38 MAPK-dependent mechanism." Am J. Physiol/Regul Integ 2006.
Wilting et al., 2007, The Proepicardium Delivers Hemangioblasts but not Lymphangioblasts to the Developing Heart, Developmental Biology 305:451-459.
Wilting et al., Aug. 2002, The transcription factor Prox1 is a marker for lymphatic endothelial cells in normal and diseased human tissues, The FASEB Journal, 16:1271-1273.
Wolinsky et al., Feb. 1990, Use of a perforated balloon catheter to deliver concentrated heparin into the wall of the normal canine artery, J. Am. Coll. Cardiol. 15(2):475-481.
Xie et al., 2006, Preparation of bupleurum nasal spray and evaluation on its safety and efficacy, Chem. Pharm. Bull., 54(1):48-53.
Young, 2000 Science "A Time for Restraint," 287:1424.
Yuksel et al., Apr. 2000, De novo adipose tissue generation through long-term, local delivery of insulin and insulin-like growth factor-1 by PLGA/PEG microspheres in an in vivo rat model: a novel concept and capability, Plastic and Reconstructive Surgery, 105:1721-1729.
Zhang, "Bone marrow-derived endothelial progenitor cells participate in cerebral neovascularization after focal cerebral ischemia in the adult mouse," Circ Res. (2002) 90:284-288.
BD Biosciences, Feb. 15, 2002, Product Specification Sheet; BD Matrigel™ Basement Membrane Matrix, 3 pp.
Bhagavati, et al., 2004, Isolation and enrichment of skeletal muscle progenitor cells from mouse bone marrow, Biochem. Biophys. Res. Comm. 318(1):318-24.
Caplan and Goldberg, 1999, Principles of tissue engineered regeneration of skeletal tissues, Clin Orthop Suppl. 367: 12-16.
Cousin et al., Jul. 2009, Adult stromal cells dervied from human adipose tissue provoke pancreatic cancer cell death both in vitro and in vivo, PLoS One, 4(7), e6278.
Craiu, et al., 2005, Flowing cells through pulsed electric fields efficiently purges stem cell preparations of contaminating myeloma cells while preserving stem cell function, Blood 105(5):2235-2238.
Cui, et al', 2006, Effects of low-intensity ultrasound on chondrogenic differentiation of mesenchymal stem cells embedded in polyglycolic acid: an in vivo study, Tissue Eng. 12(1):75-82.
Di Carlo, et al., 2004, Hypoxia inhibits myogenic differentiation through accelerated MyoD degradation, The Journal of Biological Chemistry, 279(16):16332-338.
Ebisawa, et al., 2004, Ultrasound enhances transforming growth factor B-mediated chondrocyte differentiation of human mesenchymal stem cells, Tissue Eng. 10(5-6):921-9.
Eichler, et al., 2003, Engraftment capacity of umbilical cord blood cells processed by either whole blood preparation or filtration, Stem Cells 21:208-216.
Eppich, et al., 2000, Pulsed electric fields for selection of hematopoietic cells and depletion of tumor cell contaminants, Nature Biotechnology 18:882-887.
Fink, et al., 2004, Induction of adipocyte-like phenotype in human mesenchymal stem cells by hypoxia, Stem Cells 22:1346-1355.
Gimble et al., 1995, Bone morphogenetic proteins inhibit adipocyte differentiation by bone marrow stromal cells, J. Cell Biochem. 58(3):393-402.
Gimble et al., 2007, Adipose-derived stem cells for regenerative medicine, Circulation Research, 100:1249-1260.
Graepler et al., 1998, Magnetic cell sorting for parietal cell purification using a new monoclonal antibody without influence on cell function, J. Biochem. Biophys. Methods 36(2-3):143-55.
Gronthos et al., 2001, Surface protein characterization of human adipose tissue-derived stromal cells, Journal of Cellular Physiology, 189:54-63.
Haynes, 1988, Principles of flow cytometery, Cytometry Supplement, 3:7-17.
Herzenberg et al., 2002, The history and future of the fluorescence activated cell sorter and flow cytometry: a view from Stanford, Clinical Chemistry, 48(10):1819-1827.
Kawamoto et al., 2001, Therapeutic potential of ex vivo expanded endothelial progenitor cells for myocardial ischemia, Circulation, 103:634-637.
Kim et al., 2007, Systemic transplantation of human adipose stem cells attenuated cerebral inflammation and degeneration in a hemorrhagic stroke model, Brain Research, 1183:42-50.
Knutson, et al., 1999, Increased anticoagulant osmolality improves separation of leukocytes from red blood cells (RBC), Transfusion Science 21: 185-191.
Kobari et al., 2001, CD133+ cell selection is an alternative to CD34+ cell selection for ex vivo expansion of hematopoietic stem cells, J. Hematother. Stem Cell Res. 10(2):273-81.
Kumano et al, 1997, Effects of osmotic agents on hyaluronan synthesis in human peritoneal mesothelial cells and fibroblasts, Adv. Perit. Dial. 13:58-63.
Lennon, et al., 2001, Cultivation of rat marrow-derived mesenchymal stem cells in reduced oxygen tension: effects on in vitro and in vivo osteochondrogenesis, J. Cell Phys. 187(3):345-55.
Miyagi, et al., 2001, Application of hypothermia to autologous stem cell purging, Cryobiology 42:190-95.
Rajpurohit, et al., 2002, Phenotypic characteristics of the nucleus pulposus: expression of hypoxia inducing factor-1, glucose transporter-1 and mmp-2, Cell Tissue Res. 308(3):401-7.
Rambaldi, et al., 1998, Innovative two-step negative selection of granulocyte colony-stimulating factor-mobilized circulating progenitor cells: adequacy for autologous and allogeneic transplantation, Blood 91(6):2189-2196.
Rehman et al., 2007, Human adipose stromal cells express the angiogenic factor VEGF and its receptor VEGFR-2, Arterioscler Thromb Vasc Biol, 22:878, Poster Presentation P111, p. a-19.
Rivard et al., 1998, Angiogenesis and vasculogenesis in treatment of cardiovascular disease, Molecular Medicine, 4:429-440.

(56) References Cited

OTHER PUBLICATIONS

Rolovic, et al., 1990, Megakaryocytopoiesis in experimentally induced chronic normobaric hypoxia, Exp. Hematol. 18(3):190-4.

Saha, et al. 2006, Inhabition of human embryonic stem cell differentiation by mechanical strain, J. Cell Phys. 206(1):126-137.

Shimazaki, et al., 1998, Elimination of myeloma cells from bone marrow by using monoclonal antibodies and magnetic immunobeads, Blood 72(4):1248-54.

Steffgen et al, 2003, Osmoregulation of aldose reductase and sorbitol dehydrogenase in cultivated interstitial cells of rat renal inner medulla, Nephrol. Dial. Transplant. 18(11):2255-61.

Tondreau et al., 2004, Isolation of BM mesenchymal stem cells by plastic adhesion or negative selection: phenotype, proliferation kinetics and differentiation potential, Cytotherapy, 6(4):372-379.

Tschopp et al, 1983, Hypergravity promotes cell proliferation, Experientia 39(12):1323-9.

Wang, et al., 1992, An effective immunomagnetic method for bone marrow purging in T cell malignancies, Bone Marrow Transplant. 9(5):319-23 (abstract).

Worster et al., 2001, Chondrocytic differentiation of mesenchymal stem cells sequentially exposed to transforming growth factor-B1 in monolayer and insulin-like growth factor-I in a three dimensional matrix, J. Orthop. Res. 19(4):738-49.

\* cited by examiner

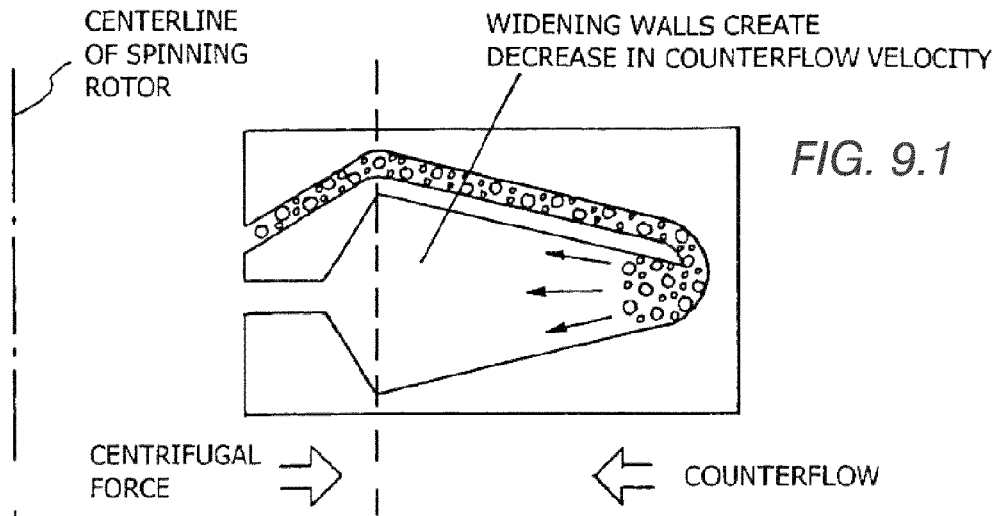
FIG. 9.1
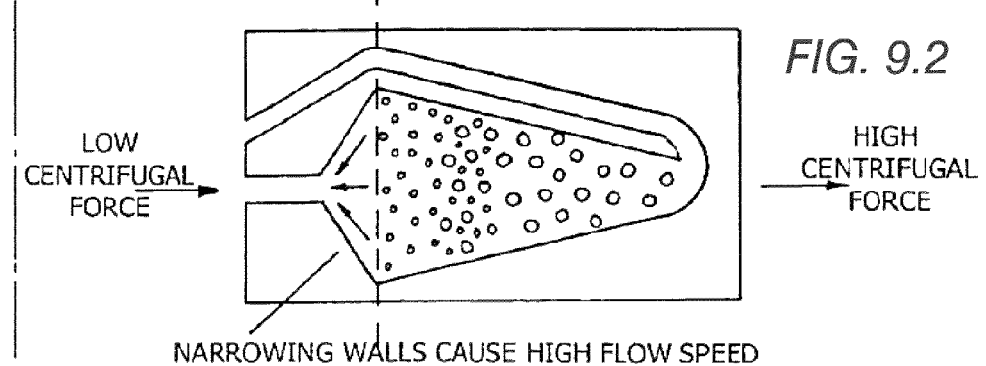
FIG. 9.2
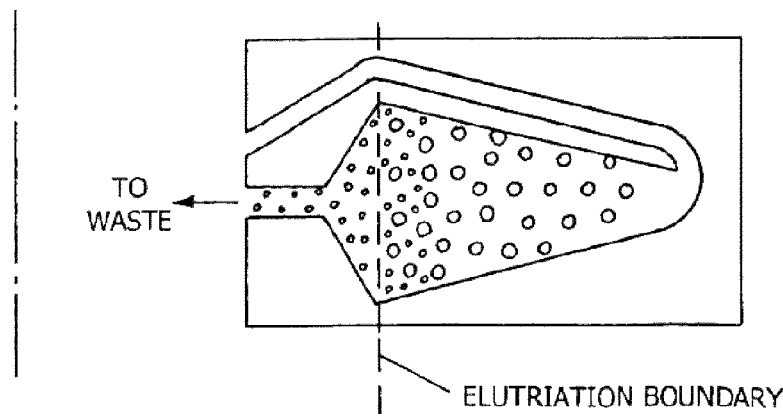
FIG. 9.3

TANGENTIAL CROSS-FLOW FILTRATION
(HIGH PERMEATE RATE)

DEAD-END FILTRATION
(LOW PERMEATE RATE)

UEA-1 Staining of ADC-derived EPC Colony

Growth of CD31-positive Vascular Structures from ADC of Normal and STZ-Treated Mice

METHODS OF USING ADIPOSE TISSUE-DERIVED CELLS IN AUGMENTING AUTOLOGOUS FAT TRANSFER

CROSS-REFERENCE TO RELATED APPLICATIONS

This application is a continuation under 35 U.S.C. §120 of U.S. patent application Ser. No. 12/694,103, entitled METHODS OF USING ADIPOSE TISSUE-DERIVED CELLS IN AUGMENTING AUTOLOGOUS FAT TRANSFER, filed Jan. 26, 2010, which is a divisional under 35 U.S.C. §121 of U.S. application Ser. No. 10/871,503, now U.S. Pat. No. 7,651,684, entitled METHODS OF USING ADIPOSE TISSUE-DERIVED CELLS IN AUGMENTING AUTOLOGOUS FAT TRANSFER, filed on Jun. 18, 2004, which is a continuation-in-part application of U.S. application Ser. No. 10/316,127, filed on Dec. 9, 2002, now abandoned, entitled SYSTEMS AND METHODS FOR TREATING PATIENTS WITH PROCESSED LIPOASPIRATE CELLS, which claims the benefit of U.S. Provisional Application No. 60/338,856, filed Dec. 7, 2001. This application also claims priority to U.S. Provisional Application No. 60/479,418, entitled METHODS OF USING ADIPOSE TISSUE DERIVED CELLS IN AUGMENTING AUTOLOGOUS FAT TRANSFER, filed Jun. 18, 2003. The contents of all the aforementioned applications are expressly incorporated herein by this reference.

BACKGROUND OF THE INVENTION

1. Field of the Invention

This invention generally relates to cells derived from adipose tissue, and more particularly, to adipose-derived regenerative cells (e.g., stem and/or progenitor cells), methods of using adipose-derived regenerative cells, compositions containing adipose-derived regenerative cells, and systems for preparing and using adipose-derived regenerative cells which are used to augment fat transfer.

2. Description of the Related Art

Fat transfer is a relatively common cosmetic, therapeutic and structural procedure involving the harvest of adipose tissue (fat) from one location and re-implantation in another location (Coleman 1995; Coleman 2001). While being largely used for repair of small cosmetic defects such as facial folds, wrinkles, pock marks and divots, fat transfer has also been used cosmetically in breast augmentation and reconstruction (Bircoll and Novack 1987; Dixon 1988). Augmentation of the buttocks has also been performed using fat transfer approaches (Cardenas-Camarena, Lacouture et al. 1999; de Pedroza 2000; Peren, Gomez et al. 2000).

Existing fat transfer methods, however, are associated with substantial side effects including infection (Castello, Barros et al. 1999; Valdatta, Thione et al. 2001) and calcifications and scarring which can interfere with mammography and other breast imaging modalities (Huch, Kunzi et al. 1998). Current fat transfer methods are also frequently associated with inconsistent engraftment, wherein for example the implanted material is fully or partially resorbed or is replaced by scar tissue (Eremia and Newman 2000). In breast augmentation mammoplasty, for example, use of fat tissue often causes loss of function of the tissue which can be attributed in part to necrosis of implanted fat tissue during the time it takes for new blood vessels to form and feed the implant (Saunders, Keller et al. 1981; Eppley, Smith et al. 1990; Nishimura, Hashimoto et al. 2000). Similarly, for the long-term correction of soft tissue defects, numerous materials, including autologous fat, have been employed for the filling of scars, wrinkles, and other soft tissue defects (Coleman 2001; Maas and Denton 2001). As described above, however, these adipose tissue transplants also suffer from a lack of neovascularization and necrosis.

Autologous fat transfer has also been applied in non-cosmetic clinical settings where a soft tissue filler or support structure is required. One example is stress urinary incontinence in which the transplanted fat is intended to support the urethral wall and urinary sphincter structures (Palma, Riccetto et al. 1997; Lee, Kung et al. 2001). However, the lack of durability of the transplanted fat has prevented widespread acceptance of this technique. A similar approach has been used in fecal incontinence, which is another sphincter disorder (Shafik 1995; Bernardi, Favetta et al. 1998). Other examples where fat transfer has been applied in non-cosmetic clinical settings include vocal cord paralysis, vocal atrophy, intubation trauma, and post-hemilaryngectomy defects, and vocal implantation (Koufman 1991; Mikaelian, Lowry et al. 1991; Hsiung, Woo et al. 2000; Perie, Ming et al. 2002), repair of soft tissue defects caused by irradiation (Jackson, Simman et al. 2001) and war injury (Ghobadi, Zangeneh et al. 1995), in lumbar disc surgery (Bernsmann, Kramer et al. 2001; Kanamori, Kawaguchi et al. 2001), and repair of atrophied tissue in the plantar foot pad (Chairman 1994; Lauf, Freedman et al. 1998). All of these approaches have encountered the problems described above for cosmetic applications.

A number of groups have looked at ways to supplement the graft in such a way as to improve long-term survival and retention. One group has reported results using a serum-free cell culture medium to enhance graft survival in an animal model (Ullmann, Hyams et al. 1998) while others have shown that augmenting transferred tissue with growth factors can enhance graft viability in another model system (Eppley, Snyders et al. 1992; Yuksel, Weinfeld et al. 2000; Yuksel, Weinfeld et al. 2000).

A different approach has been proposed by Schoeller et al. in which adipocyte precursor cells are embedded in fibrin glue and then implanted in the hope that the cells survive and generate new adipose tissue from scratch (Schoeller, Lille et al. 2001). Others have used a similar approach involving seeding artificial polymers with these cells (Patrick, Chauvin et al. 1999). Problems associated with these approaches are that the approaches may bring only one component of adipose tissue (the adipocyte) leaving new blood vessel production (angiogenesis) to endogenous mechanisms. Further, given the limited self-renewal capacity of pre-adipocytes they may be unable to deliver long-term production of adipocytes.

Accordingly, there remains a need for improved methods of administering adipose tissue to patients which reduces the problems associated with existing methods.

SUMMARY OF THE INVENTION

The present invention is based, at least in part, on the discovery that the adipose derived regenerative cells (e.g., endothelial precursor cells) of the present invention are capable of providing angiogenic support and long-term production of both vascular endothelial cells and adipocytes. Accordingly, the present invention provides methods of augmenting fat transfer, e.g., autologous fat transfer. The present invention also provides rapid and reliable devices, systems and methods for preparing adult regenerative cells from adipose tissue with increased yield, consistency and purity with a diminished or non-existent need for post-extraction manipulation. The present invention further provides compositions, methods, and systems for using cells derived from adipose tissue that may be admixed with intact adipose tissue and placed directly into a recipient along with such additives necessary to promote, engender, or support a therapeutic, structural, or cosmetic benefit.

In one embodiment, the regenerative cells prepared according to this disclosure are prepared and subsequently mixed with intact (non-disaggregated or non-processed) adipose tissue fragments to form a composition. Thus, the composition comprises a mixture of adipose tissue and regenerative cells. The composition may be implanted into the recipient to provide an autologous soft tissue filler for correction of contour defects (wrinkles, "divots," pockmarks, and larger deficits) or for providing support to damaged structures such as the urethra. The composition may also be administered to breast regions in connection with breast augmentation procedures and soft tissue defects.

The adipose tissue processing occurs in a system that maintains a closed, sterile fluid/tissue pathway. This is achieved by use of a pre-assembled, linked set of closed, sterile containers and tubing allowing for transfer of tissue and fluid elements within a closed pathway. The system may be linked to a processing device which can automate the addition of reagents, temperature, and timing of processing thus relieving operators of the need to manually manage the process. In a preferred embodiment the entire procedure from tissue extraction through processing and placement into the recipient would all be performed in the same facility, indeed, even within the same room of the patient undergoing the procedure.

In certain embodiments, a method of treating a patient includes steps of: a) providing a tissue removal system; b) removing adipose tissue from a patient using the tissue removal system, the adipose tissue having a concentration of regenerative cells; c) processing at least a part of the adipose tissue to obtain a concentration of regenerative cells other than the concentration of regenerative cells of the adipose tissue before processing; and d) administering the regenerative cells to a patient without removing the regenerative cells from the tissue removal system before being administered to the patient To thereby treat the patient.

In other embodiments, a method of treating a patient includes: a) providing an adipose tissue removal system; b) removing adipose tissue from a patient using the adipose tissue removal system, the adipose tissue having a concentration of regenerative cells; c) processing the adipose tissue to increase the concentration of regenerative cells in the adipose tissue; d) mixing the adipose tissue having the concentrated regenerative cells with another unit portion of adipose tissue; and e) administering the adipose tissue with the increased concentration of regenerative cells to a patient to thereby treat the patient.

In particular embodiments, a patient is treated for soft-tissue defects. In other embodiments, the breast of a patient is treated. In yet other embodiments, the patient is treated for urinary incontinence. The methods of treatment disclosed herein may be used to treat any cosmetic or non-cosmetic disorder which requires fat transfer both autologous and non-autologous.

In preferred embodiments, the regenerative cells used to treat are patient are stem cells or progenitor cells. In other embodiments, the regenerative cells are endothelial progenitor cells. In yet other embodiments, the regenerative cells are any population of regenerative cells as described herein. Additionally, the regenerative cell population used in the methods of treatment encompassed by the invention may be a homogenous or heterogeneous population of cells.

In accordance with yet another aspect of the invention, the regenerative cells are placed into the recipient in combination with other cells, tissue, tissue fragments, or other stimulators of cell growth and/or differentiation. For example, the regenerative cells may be combined with growth factors and/or cytokines, e.g., angiogenic or arteriogenic growth factors. The regenerative cells may also be combined with immunosuppressive drugs. These additives may be administered during or after the regenerative cells have been concentrated using the systems and methods of the invention. In yet another aspect of the invention, the regenerative cells are directed to other targets such as implant materials, surgical devices, cell culturing devices or purification devices, prior to placement into the recipient. In a preferred embodiment, the cells, with any of the abovementioned additives, are placed into the person from whom they were obtained in the context of a single operative procedure with the intention of deriving a therapeutic, structural, or cosmetic benefit to the recipient.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description.

BRIEF DESCRIPTION OF THE DRAWINGS

FIGS. 9-1, 9-2 and 9-3 illustrate an elutriation component in use with the system of the invention.

FIGS. 14-1 and 14-2 are illustrations of an exemplary re-usable component for a system of the invention.

FIGS. 15A-1 and 15A-2 are illustrations of an exemplary device of the invention assembled using a disposable set similar to FIG. 13 and a re-usable component similar to FIG. 14.

DETAILED DESCRIPTION OF THE PREFERRED EMBODIMENT

Figure 1:
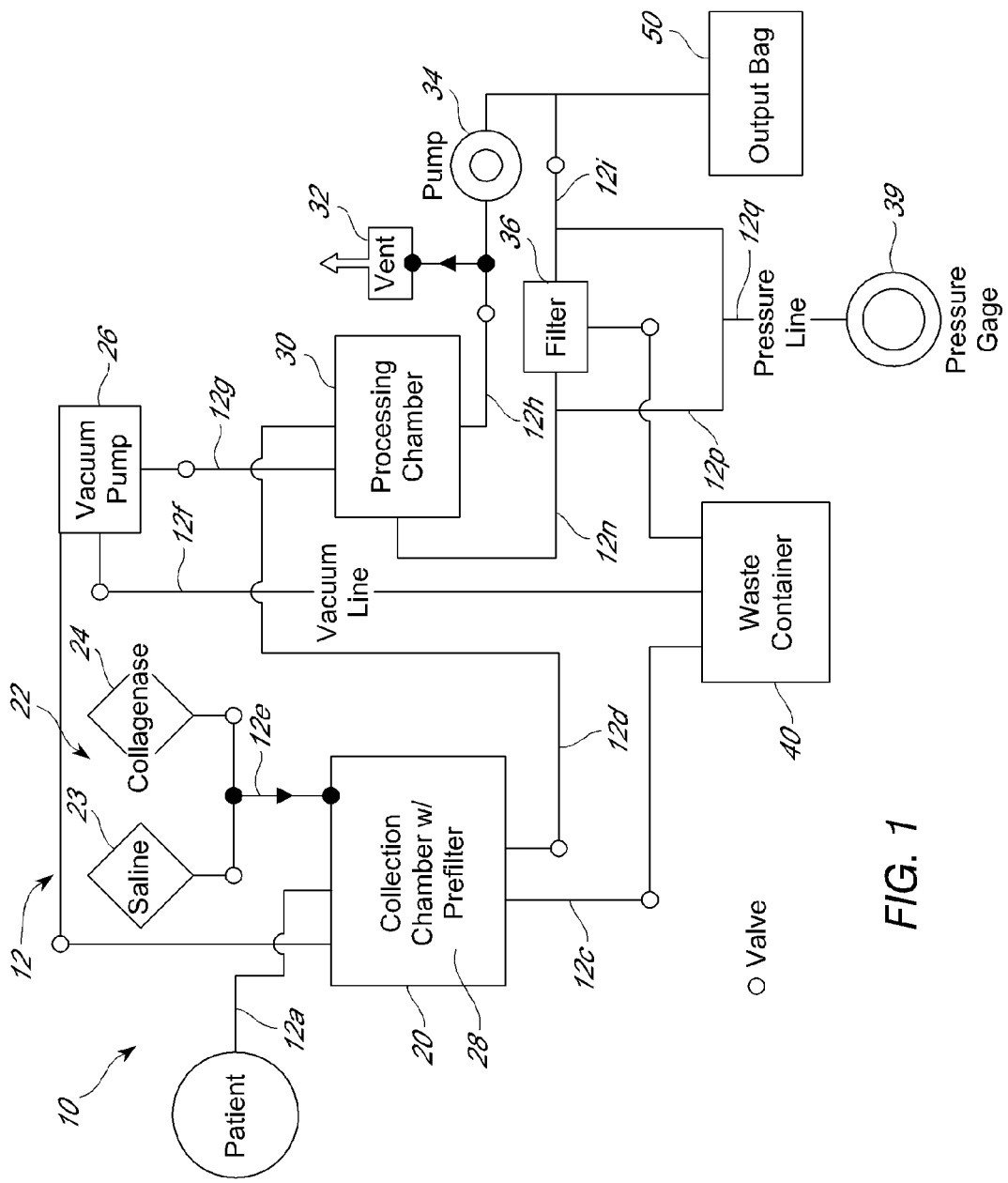
FIG. 1 is an illustration of a system for separating regenerative cells from tissue which includes one filter assembly.

The present invention provides methods for augmenting autologous fat transfer using adipose derived regenerative cells ("ADCs"). For example, the present invention demonstrates that the adipose derived regenerative cells of the invention (1) express angiogenic growth factors and cytokines, including PIGF, VEGF, bFGF, IGF-II, Eotaxin, G-CSF, GM-CSF, IL-12 p40/p70, EL-12 p70, IL-13, IL-6, IL-9, Leptin, MCP-1, M-CSF, MIG, PF4, TIMP-1, TIMP-2, TNF-α and Thrombopoetin, (2) comprise endothelial progenitor cells (EPC) which have a well-established function in blood vessel formation, (3) develop into blood vessels in vitro, and (4) support ischemic tissue survival in vivo. Accordingly, the regenerative cells are capable of augmenting autologous fat transfer by, for example, promoting neovascularization at the site of administration.

In order that the present invention may be more readily understood, certain terms are first defined. Additional definitions are set forth throughout the detailed description.

As used herein, "regenerative cell" refers to any cells obtained using the systems and methods of the present invention which cause or contribute to complete or partial regeneration, restoration, or substitution of structure or function of an organ, tissue, or physiologic unit or system to thereby provide a therapeutic, structural or cosmetic benefit. Examples of regenerative cells include: ASCs, endothelial cells, endothelial precursor cells, endothelial progenitor cells, macrophages, fibroblasts, pericytes, smooth muscle cells, preadipocytes, differentiated or de-differentiated adipocytes, keratinocytes, unipotent and multipotent progenitor and precursor cells (and their progeny), and lymphocytes.

One mechanism by which the regenerative cells may provide a therapeutic, structural or cosmetic benefit is by incorporating themselves or their progeny into newly generated, existing or repaired tissues or tissue components. For example, ASCs and/or their progeny may incorporate into newly generated bone, muscle, or other structural or functional tissue and thereby cause or contribute to a therapeutic, structural or cosmetic improvement. Similarly, endothelial cells or endothelial precursor or progenitor cells and their progeny may incorporate into existing, newly generated, repaired, or expanded blood vessels to thereby cause or contribute to a therapeutic, structural or cosmetic benefit.

Another mechanism by which the regenerative cells may provide a therapeutic, structural or cosmetic benefit is by expressing and/or secreting molecules, e.g., growth factors, that promote creation, retention, restoration, and/or regeneration of structure or function of a given tissue or tissue component. For example, regenerative cells may express and/or secrete molecules which result in enhanced growth of tissues or cells that then participate directly or indirectly in improved structure or function. Regenerative cells may express and/or secrete growth factors or cytokines, including, for example, Vascular Endothelial Growth Factor (VEGF), Placental Growth factor (PlGF), and their isoforms, which may perform one or more of the following functions: stimulate development of new blood vessels, i.e., promote angiogenesis; improve oxygen supply of pre-existent small blood vessels (collaterals) by expanding their blood carrying capacity; induce mobilization of regenerative cells from sites distant from the site of injury to thereby enhance the homing and migration of such cells to the site of injury; stimulate the growth and/or promote the survival of cells within a site of injury thereby promoting retention of function or structure; deliver molecules with anti-apoptotic properties thereby reducing the rate or likelihood of cell death and permanent loss of function; and interact with endogenous regenerative cells and/or other physiological mechanisms.

The regenerative cells may be used in their 'native' form as present in or extracted from the tissue using the systems and methods of the present invention or they may be modified by stimulation or priming with growth factors or other biologic response modifiers, by gene transfer (transient or stable transfer), by further sub-fractionation of the resultant population on the basis or physical properties (for example size or density), differential adherence to a solid phase material, expression of cell surface or intracellular molecules, cell culture or other ex vivo or in vivo manipulation, modification, or fractionation as further described herein. The regenerative cells may also be used in combination with other cells or devices such as synthetic or biologic scaffolds, materials or devices that deliver factors, drugs, chemicals or other agents that modify or enhance the relevant characteristics of the cells as further described herein.

As used herein, "regenerative cell composition" refers to the composition of cells typically present in a volume of liquid after a tissue, e.g., adipose tissue, is washed and at least partially disaggregated. For example, a regenerative cell composition of the invention comprises multiple different types of regenerative cells, including ASCs, endothelial cells, endothelial precursor cells, endothelial progenitor cells, macrophages, fibroblasts, pericytes, smooth muscle cells, preadipocytes, differentiated or de-differentiated adipocytes, keratinocytes, unipotent and multipotent progenitor and precursor cells (and their progeny), and lymphocytes. The regenerative cell composition may also contain one or more contaminants, such as collagen, which may be present in the tissue fragments, or residual collagenase or other enzyme or agent employed in or resulting from the tissue disaggregation process described herein.

As used herein, "regenerative medicine" refers to any therapeutic, structural or cosmetic benefit that is derived from the placement, either directly or indirectly, of regenerative cells into a subject. As used herein, the phrase "fat transfer" is a form of regenerative medicine and is intended to include all procedures whereby surplus fat cells are removed from one area of a body and re-implanted into another area of a body.

Fat transfer includes both autologous and non-autologous fat transfer. The phrase "autologous fat transfer" is intended to include all procedures whereby the fat removal and re-implantation are performed on the same subject. Exemplary cosmetic fat transfer procedures include fat grafts or implants to the lips, nasolabials (mouth to nose folds), wrinkles and other facial folds (depressions around the eyes, between the brows, as well as on the rest of the face), undereyes, cheeks, chin, temples, breasts, thighs, calves, arms, abdomen, buttocks as well as any other area of the body. Cosmetic fat transfer procedures may be combined with other cosmetic applications such as facial implants, blepheroplasty, brow lifts, face lifts, neck lift, botox applications, chemical peels and laser resurfacing. Non-cosmetic fat transfer procedures include implants to treat sphincter disorders, including fat implants in gastroesophageal, urethral and rectal sphincters. Fat transfer procedures may also be used to treat trauma (e.g., radiation) or disease induced soft tissue defects (e.g., abdominal hernia), hemifacial microsomia, vocal cord injury and lumbar spine disorders. Fat transfer procedures may also be used to treat adipose-related diseases or disorders, including but not limited to dyslipidimia, hypoadiponectinemia, hyperlipidemia, lipatrophy and lipohypertrophy.

As used herein, "stem cell" refers to a multipotent regenerative cell with the potential to differentiate into a variety of other cell types, which perform one or more specific functions and have the ability to self-renew. Some of the stem cells disclosed herein may be pluripotent.

As used herein, "progenitor cell" refers to a multipotent regenerative cell with the potential to differentiate into more than one cell type. "Progenitor cell", as used herein, also refers to a unipotent regenerative cell with the potential to differentiate into only a single cell type, which performs one or more specific functions and has limited or no ability to self-renew. In particular, as used herein, "endothelial progenitor cell" refers to a multipotent or unipotent cell with the potential to differentiate into vascular endothelial cells.

As used herein, "precursor cell" refers to a unipotent regenerative cell with the potential to differentiate into one cell type. Precursor cells and their progeny may retain extensive proliferative capacity, e.g., lymphocytes and endothelial cells, which can proliferate under appropriate conditions.

As used herein, the term "angiogenesis" refers to the process by which new blood vessels are generated from existing vasculature and tissue (Folkman, 1995). The phrase "repair or remodeling" refers to the reformation of existing vasculature. The alleviation of tissue ischemia is critically dependent upon angiogenesis. The spontaneous growth of new blood vessels provides collateral circulation in and around an ischemic area, improves blood flow, and alleviates the symptoms caused by the ischemia. Angiogenesis mediated diseases and disorders include acute myocardial infarction, ischemic cardiomyopathy, peripheral vascular disease, ischemic stroke, acute tubular necrosis, ischemic wounds-including AFT, sepsis, ischemic bowel disease, diabetic retinopathy, neuropathy and nephropathy, vasculitidies, ischemic encephalopathy, erectile dysfunction-physiologic, ischemic or traumatic spinal cord injuries, multiple organ system failure, ischemic gum disease, and transplant related ischemia.

As used herein, the term "angiogenic factor" or "angiogenic protein" refers to any known protein, peptide or other agent capable of promoting growth of new blood vessels from existing vasculature ("angiogenesis"). Suitable angiogenic factors for use in the invention include, but are not limited to, Placenta Growth Factor (Luttun et al., 2002), Macrophage Colony Stimulating Factor (Aharinejad et al., 1995), Granulocyte Macrophage Colony Stimulating Factor (Buschmann et al., 2003), Vascular Endothelial Growth Factor (VEGF)-A, VEGF-A, VEGF-B, VEGF-C, VEGF-D, VEGF-E (Mints et al., 2002), neuropilin (Wang et al., 2003), fibroblast growth factor (FGF)-1, FGF-2(bFGF), FGF-3, FGF4, FGF-5, FGF-6 (Botta et al., 2000), Angiopoietin 1, Angiopoietin 2 (Sundberg et al., 2002), erythropoietin (Ribatti et al., 2003), BMP-2, BMP4, BMP-7 (Carano and Filvaroff, 2003), TGF-beta (Xiong et al., 2002), IGF-1 (Shigematsu et al., 1999), Osteopontin (Asou et al., 2001), Pleiotropin (Beecken et al., 2000), Activin (Lamouille et al., 2002), Endothelin-1 (Bagnato and Spinella, 2003) and combinations thereof. Angiogenic factors can act independently, or in combination with one another. When in combination, angiogenic factors can also act synergistically, whereby the combined effect of the factors is greater than the sum of the effects of the individual factors taken separately. The term "angiogenic factor" or "angiogenic protein" also encompasses functional analogues of such factors. Functional analogues include, for example, functional portions of the factors. Functional analogues also include anti-idiotypic antibodies which bind to the receptors of the factors and, thus, mimic the activity of the factors in promoting angiogenesis and/or tissue remodeling. Methods for generating such anti-idiotypic antibodies are well known in the art and are described, for example, in WO 97/23510, the contents of which are incorporated by reference herein.

Angiogenic factors used in the present invention can be produced or obtained from any suitable source. For example, the factors can be purified from their native sources, or produced synthetically or by recombinant expression. The factors can be administered to patients as a protein composition. Alternatively, the factors can be administered in the form of an expression plasmid encoding the factors. The construction of suitable expression plasmids is well known in the art. Suitable vectors for constructing expression plasmids include, for example, adenoviral vectors, retroviral vectors, adeno-associated viral vectors, RNA vectors, liposomes, cationic lipids, lentiviral vectors and transposons.

As used herein "stem cell number" or "stem cell frequency" refers to the number of colonies observed in a clonogenic assay in which adipose derived cells (ADC) are plated at low cell density (<10,000 cells/well) and grown in growth medium supporting MSC growth (for example, DMEM/F12 medium supplemented with 10% fetal calf serum, 5% horse serum, and antibiotic/antimycotic agents. Cells are grown for two weeks after which cultures are stained with hematoxylin and colonies of more than 50 cells are counted as CFU-F. Stem cell frequency is calculated as the number of CFU-F observed per 100 nucleated cells plated (for example; 15 colonies counted in a plate initiated with 1,000 nucleated ADC cells gives a stem cell frequency of 1.5%). Stem cell number is calculated as stem cell frequency multiplied by the total number of nucleated ADC cells obtained. A high percentage (.about.100%) of CFU-F grown from ADC cells express the cell surface molecule CD 105 which is also expressed by marrow-derived stem cells (Barry et al., 1999). CD105 is also expressed by adipose tissue-derived stem cells (Zuk et al., 2002).

As used herein, the term "adipose tissue" refers to fat including the connective tissue that stores fat. Adipose tissue contains multiple regenerative cell types, including ASCs and endothelial progenitor and precursor cells.

As used herein, the term "unit of adipose tissue" refers to a discrete or measurable amount of adipose tissue. A unit of adipose tissue may be measured by determining the weight and/or volume of the unit. Based on the data identified above, a unit of processed adipose tissue, as removed from a patient, has a cellular component in which at least 0.1% of the cellular component is stem cells; that is, it has a stem cell frequency, determined as described above, of at least 0.1%. In reference to the disclosure herein, a unit of adipose tissue may refer to the entire amount of adipose tissue removed from a patient, or an amount that is less than the entire amount of adipose tissue removed from a patient. Thus, a unit of adipose tissue may be combined with another unit of adipose tissue to form a unit of adipose tissue that has a weight or volume that is the sum of the individual units.

As used herein, the term "portion" refers to an amount of a material that is less than a whole. A minor portion refers to an amount that is less than 50%, and a major portion refers to an amount greater than 50%. Thus, a unit of adipose tissue that is less than the entire amount of adipose tissue removed from a patient is a portion of the removed adipose tissue.

As used herein, the term "processed lipoaspirate" refers to adipose tissue that has been processed to separate the active cellular component (e.g., the component containing stem and progenitor cells) from the mature adipocytes and connective tissue. This fraction is referred to herein as "adipose-derived cells" or "ADC." Typically, ADC refers to the pellet of regenerative cells obtained by washing and separating the cells from the adipose tissue. The pellet is typically obtained by centrifuging a suspension of cells so that the cells aggregate at the bottom of a centrifuge chamber or cell concentrator.

As used herein, the terms "administering," "introducing," "delivering," "placement" and "transplanting" are used interchangeably herein and refer to the placement of the ADC of the invention into a subject by a method or route which results in at least partial localization of the ADC at a desired site. The ADC can be administered by any appropriate route which results in delivery to a desired location in the subject where at least a portion of the cells or components of the cells remain viable. The period of viability of the cells after administration to a subject can be as short as a few hours, e.g., twenty-four hours, to a few days, to as long as several years.

As used herein, the term "subject" includes warm-blooded animals, preferably mammals, including humans. In a preferred embodiment, the subject is a primate. In an even more preferred embodiment, the subject is a human.

Reference will now be made in detail to the presently preferred embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the appended claims. The present invention may be practiced in conjunction with various cell or tissue separation techniques that are conventionally used in the art, and only so much of the commonly practiced process steps are included herein as are necessary to provide an understanding of the present invention.

As previously set forth herein, regenerative cells, e.g., stem and progenitor cells, can be harvested from a wide variety of tissues. The system of the present invention may be used for all such tissues. Adipose tissue, however, is an especially rich source of regenerative cells. Accordingly, the system of the present invention is illustrated herein using adipose tissue as a source of regenerative cells by way of example only and not limitation.

Adipose tissue can be obtained by any method known to a person of ordinary skill in the art. For example, adipose tissue may be removed from a patient by liposuction (syringe or power assisted) or by lipectomy, e.g., suction-assisted lipoplasty, ultrasound-assisted lipoplasty, and excisional lipectomy or combinations thereof. The adipose tissue is removed and collected and processed by a system of the invention described herein for the purpose of separating and concentrating regenerative cells. The amount of tissue collected depends on numerous factors, including the body mass index and age of the donor, the time available for collection, the availability of accessible adipose tissue harvest sites, concomitant and pre-existing medications and conditions (such as anticoagulant therapy), and the clinical purpose for which the tissue is being collected. For example, the stem cell percentage of 100 ml of adipose tissue extracted from a lean individual is greater than that extracted from an obese donor (Table 1). This likely reflects a dilutive effect of the increased fat content in the obese individual. Therefore, it may be desirable, in accordance with one aspect of the invention, to obtain larger amounts of tissue from overweight donors compared to the amounts that would be withdrawn from leaner patients. This observation also indicates that the utility of this invention is not limited to individuals with large amounts of adipose tissue.

TABLE 1

Effect of Body Mass Index on Tissue and Cell Yield

| Body Mass Index Status | Amount of Tissue Obtained (g) | Total Cell Yield ($\times 10^7$) |
|---|---|---|
| Normal | 641 ± 142 | 2.1 ± 0.4 |
| Obese | 1,225 ± 173 | 2.4 ± 0.5 |
| p value | 0.03 | 0.6 |

After the adipose tissue is processed, the resulting regenerative cells are substantially free from mature adipocytes and connective tissue. Accordingly, the system of the present invention generates a heterogenous plurality of adipose derived regenerative cells which may be used for research and/or therapeutic purposes. In a preferred embodiment, the cells are suitable for placement or re-infusion within the body of the recipient. In other embodiments, the cells may be used for research, e.g., the cells can be used to establish stem or progenitor cell lines which can survive for extended periods of time and be used for further study.

Reference will now be made in detail to the presently preferred embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, front, distal, and proximal are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the appended claims. The present invention may be utilized in conjunction with various medical procedures that are conventionally used in the art.

Referring now to the Figures, a system 10 of the present invention is generally comprised of one or more of a tissue collection chamber 20, a processing chamber 30, a waste chamber 40, an output chamber 50 and a sample chamber 60. The various chambers are coupled together via one or more conduits 12 such that fluids containing biological material may pass from one chamber to another while maintaining a closed, sterile fluid/tissue pathway. The conduits may comprise rigid or flexible bodies referred to interchangeably herein as lumens or tubing. In certain embodiments, the conduits are in the form of flexible tubing, such as polyethylene tubing conventionally used in clinical settings. In other embodiments, the tubings may be constructed of silicone. The flexile tubing used should be capable of withstanding negative pressure to reduce the likelihood of collapse. The flexible tubing used should also be capable of withstanding positive pressure which is generated by, for example, a positive displacement pump, which may be used in the system.

All the chambers of the system may be comprised of one or more ports, e.g., outlet 22 or inlet 21 ports, which accept standard IV, syringe and suction tubing connections. The ports may be a sealed port such as a rubber septum closed syringe needle access port 51. The inlet ports may be coupled to one or more cannulas (not shown) by way of conduits. For example, a tissue inlet port 21 may be coupled to an integrated single use liposuction cannula and the conduit may be a flexible tubing. The conduits are generally positioned to provide fluid passageways from one chamber of the system to another. Towards this end, the conduits and ports may be coupled to, for example, a suction device (not shown) which may be manually or automatically operated. The suction device may be, e.g., a syringe or an electric pump. The suction device should be capable of providing sufficient negative pressure to aspirate tissue from a patient. Generally, any suitable suction device known to one of ordinary skill in the art, e.g., a surgeon, may be used.

The conduits 12 may further comprise one or more clamps (not shown) to control the flow of material among various components of the system. The clamps are useful for maintaining the sterility of the system by effectively sealing different regions of the system. Alternatively, the conduits 12 may comprise one or more valves 14 that control the flow of material through the system. The valves 14 are identified as open circles in the Figures. In preferred embodiments, the valves may be electromechanical pinch valves. In another embodiment, the valves may be pneumatic valves. In yet other embodiments, the valves may be hydraulic valves or mechanical valves. Such valves are preferably activated by a control system which may be coupled to levers. The levers may be manually manipulated such that the levers are activated. In automated embodiments, the control system may be coupled to the levers as well as a processing device which may activate the valves at pre-determined activation conditions. In certain automated embodiments, activation of the valves may be partially automated and partially subject to the user's preference such that the process may be optimized. In yet other embodiments, certain valves may be activated manually and others automatically through the processing device. The valves 14 may also be used in conjunction with one or more pumps, e.g., peristaltic pumps 34 or positive displacement pumps (not shown). The conduits 12 and/or the valves 14 may also be comprised of sensors 29, e.g., optical sensors, ultrasonic sensors, pressure sensors or other forms of monitors known in the art that are capable of distinguishing among the various fluid components and fluid levels that flow through the system. In a preferred embodiment, the sensors 29 may be optical sensors.

The system may also include a plurality of filters 36. In certain embodiments, the filters may be within a chamber of the system 28. Different chambers within the system may be comprised of different filters. The filters are effective to separate the regenerative cells, e.g., stem cells and/or progenitor cells, from undesirable cells and disaggregation agents that may be used in accordance with the system. In one embodiment, a filter assembly 36 includes a hollow fiber filtration device. In another embodiment, a filter assembly 36 includes a percolative filtration device, which may or may not be used with a sedimentation process. In a further embodiment, the filter assembly 36 comprises a centrifugation device, which may or may not be used with an elutriation device and process. In yet another embodiment, the system comprises a combination of these filtering devices. The filtration functions of the present invention can be two-fold, with some filters removing things from the final concentration such as collagen, free lipid, free adipocytes and residual collagenase, and with other filters being used to concentrate the final product. The filters of the system may be comprised of a plurality of pores ranging in diameters and/or length from 20 to 800 µm. In a preferred embodiment, the collection chamber 20 has a prefixed filter 28 with a plurality of pores ranging from 80 to 400 µm. In another preferred embodiment, the collection chamber 20 has a prefixed filter 28 with a plurality of 265 µm pores. In other embodiments, the filters may be detachable and/or disposable.

The system may also be comprised of one or more temperature control devices (not shown) that are positioned to adjust the temperature of the material contained within one or more chambers of the system. The temperature control device may be a heater, a cooler or both, i.e., it may be able to switch between a heater and a cooler. The temperature device may adjust the temperature of any of the material passing through the system, including the tissue, the disaggregation agents, the resuspension agents, the rinsing agents, the washing agents or the additives. For example, heating of adipose tissue facilitates disaggregation whereas the cooling of the regenerative cell output is desirable to maintain viability. Also, if pre-warmed reagents are needed for optimal tissue processing, the role of the temperature device would be to maintain the pre-determined temperature rather than to increase or decrease the temperature.

To maintain a closed, sterile fluid/tissue pathway, all ports and valves may comprise a closure that maintains the sealed configuration of the system. The closure may be a membrane that is impermeable to fluid, air and other contaminants or it may be any other suitable closure known in the art. Furthermore, all ports of the system may be designed such that they can accommodate syringes, needles or other devices for withdrawing the materials in the chambers without compromising the sterility of the system.

As set forth herein, tissue may be extracted from a patient via any art recognized method. The aspirated tissue is transferred to the collection chamber 20 via a conduit such as 12a where it is rinsed and digested. The aspirated tissue typically enters the collection chamber 20 via a sealed entry port, such as a rubber septum closed syringe needle access port (not shown on collection chamber).

The collection chamber 20 may be comprised of a plurality of flexible or rigid canisters or cylinders or combinations thereof. For example, the collection chamber 20 may be comprised of one or more rigid canisters of varying sizes. The collection chamber 20 may also be comprised of one or more flexible bags. In such systems, the bag is preferably provided with a support, such as in internal or external frame, that helps reduce the likelihood that the bag will collapse upon the application of suction to the bag. The collection chamber 20 is sized to hold the requisite amount of saline to appropriately rinse and digest the tissue prior to the wash and concentrate stage of the process performed in the processing chamber 30. Preferably, the volume of tissue or fluid present in the collection chamber 20 is easily ascertainable to the naked eye. For example, to separate and concentrate regenerative cells from adipose tissue, a suitable collection chamber has the capacity to hold 800 ml of lipoaspirate and 1200 ml of saline. Accordingly, in one embodiment, the collection chamber 20 has a capacity of at least 2 liters. In another embodiment, to separate and concentrate red blood cells from blood, the collection chamber 20 has a capacity of at least 1.5 liters. Generally, the size of the collection chamber 20 will vary depending on the type and amount of tissue collected from the patient. The collection chamber 20 may be sized to hold as little as about 5 ml to up to about 2 liters of tissue. For smaller tissue volumes, e.g., 5 mls to 100 mls, the tissue may be gathered in a syringe prior to transfer to the collection chamber 20.

The collection chamber 20 may be constructed using any suitable biocompatible material that can be sterilized. In a preferred embodiment, the collection chamber 20 is constructed of disposable material that meets biocompatibility requirements for intravascular contact as described in the ISO 10993 standard. For example, polycarbonate acrylic or ABS may be used. The fluid path of the collection chamber 20 is preferably pyrogen free, i.e., suitable for blood use without danger of disease transmittal. In one embodiment, the collection chamber 20 is constructed of a material that allows the user to visually determine the approximate volume of tissue present in the chamber. In other embodiments, the volume of tissue and/or fluid in the collection chamber 20 is determined by automated sensors 29. The collection chamber 20 is preferably designed such that the automated system can determine the volume of tissue and/or fluid within the chamber with a reasonable degree of accuracy. In a preferred embodiment, the system senses the volume within the collection chamber with an accuracy of plus or minus fifteen percent.

In a particular embodiment provided by way of example only, the collection chamber 20 is in the form of a rigid chamber, for example, a chamber constructed of a medical grade polycarbonate containing a roughly conical prefixed filter 28 of medical grade polyester with a mesh size of 265 μm. The rigid tissue collection container may have a size of approximately eight inches high and approximately five inches in diameter; the wall thickness may be about 0.125 inches. The interior of the cylinder may be accessed through, for example, one or more ports for suction tubing, one or more ports with tubing for connection through sterile docking technology, and/or one or more ports for needle puncture access through a rubber septum. The prefixed filter 28 in the interior of the collection chamber 20 is preferably structured to retain adipose tissue and to pass non-adipose tissue as, for example, the tissues are removed from the patient. More specifically, the filter 28 may allow passage of free lipid, blood, and saline, while retaining fragments of adipose tissue during, or in another embodiment after, the initial harvesting of the adipose tissue. In that regard, the filter 28 includes a plurality of pores, of either the same or different sizes, but ranging in size from about 20 μm to 5 mm. In a preferred embodiment, the filter 28 includes a plurality of 400 μm pores. In a preferred embodiment, the filter 28 is a medical grade polyester mesh of around 200 μm thickness with a pore size of around 265 μm and around 47% open area. This material holds the tissue during rinsing but allows cells to pass out through the mesh following tissue disaggregation. Thus, when the tissues are aspirated from the patient, non-adipose tissue may be separated from adipose tissue. The same functionality could be achieved with different materials, mesh size, and the number and type of ports. For example, mesh pore sizes smaller than 100 μm or as large as several thousand microns would achieve the same purpose of allowing passage of saline and blood cells while retaining adipose tissue aggregates and fragments. Similarly, the same purpose could be achieved by use of an alternative rigid plastic material, or by many other modifications that would be known to those skilled in the art The collection chamber 20 may be further comprised of a means for washing the tissue as well as a means for mixing and/or disaggregating the tissue. The tissue may be washed, mixed or disaggregated by agitation to maximize cell viability and to minimize the amount of free lipid released. In one embodiment, the tissue is agitated by rotating the entire collection chamber 20 through an arc of varying degrees (e.g., through an arc of about 45 degrees to about 90 degrees) at varying speeds, e.g., about 30 revolutions per minute. In other embodiments, the tissue is agitated by rotating the entire collection chamber 20, wherein the collection chamber 20 is comprised of one or more paddles or protrusions rigidly attached to an inside surface of the collection chamber, through an arc of varying degrees (e.g., through an arc of about 45 degrees to about 90 degrees) at varying speeds, e.g., about 30 revolutions per minute. In certain embodiments, the inside surface of the collection chamber 20 to which the paddles 25a or protrusions are rigidly attached is a prefixed filter 28. In other embodiments, the inside surface of the collection chamber 20 to which the paddles 25a or protrusions are rigidly attached is a filter cage 27 of a prefixed filter 28.

The rotation of the collection chamber 20 may be accomplished by a drive mechanism attached to or in proximity with the collection chamber 20. The drive mechanism may be a simple belt or gear or other drive mechanism known in the art. The speed of the rotation may be, for example, 30 revolutions per minute. Generally, higher speeds have been found to generate larger volumes of free lipids and may not be optimal. In other embodiments, the tissue is agitated by placing a rotatable shaft 25 inside the collection chamber 20, wherein the rotatable shaft is comprised of one or more paddles 25a or protrusions rigidly attached to the rotatable shaft 25 which pass through the mixture as the shaft is being rotated. In certain embodiments, the rotatable shaft 25 with rigidly attached 25a paddles may be rested on the bottom of the collection chamber 20. This may be accomplished, for example, by placing the paddle-like device into a spinning magnetic field (e.g., magnetic stirrer). Alternatively, agitating of the tissue may be accomplished using a simple agitator known in the art, i.e. a device implementing shaking up and down without rotation.

Figure 5:
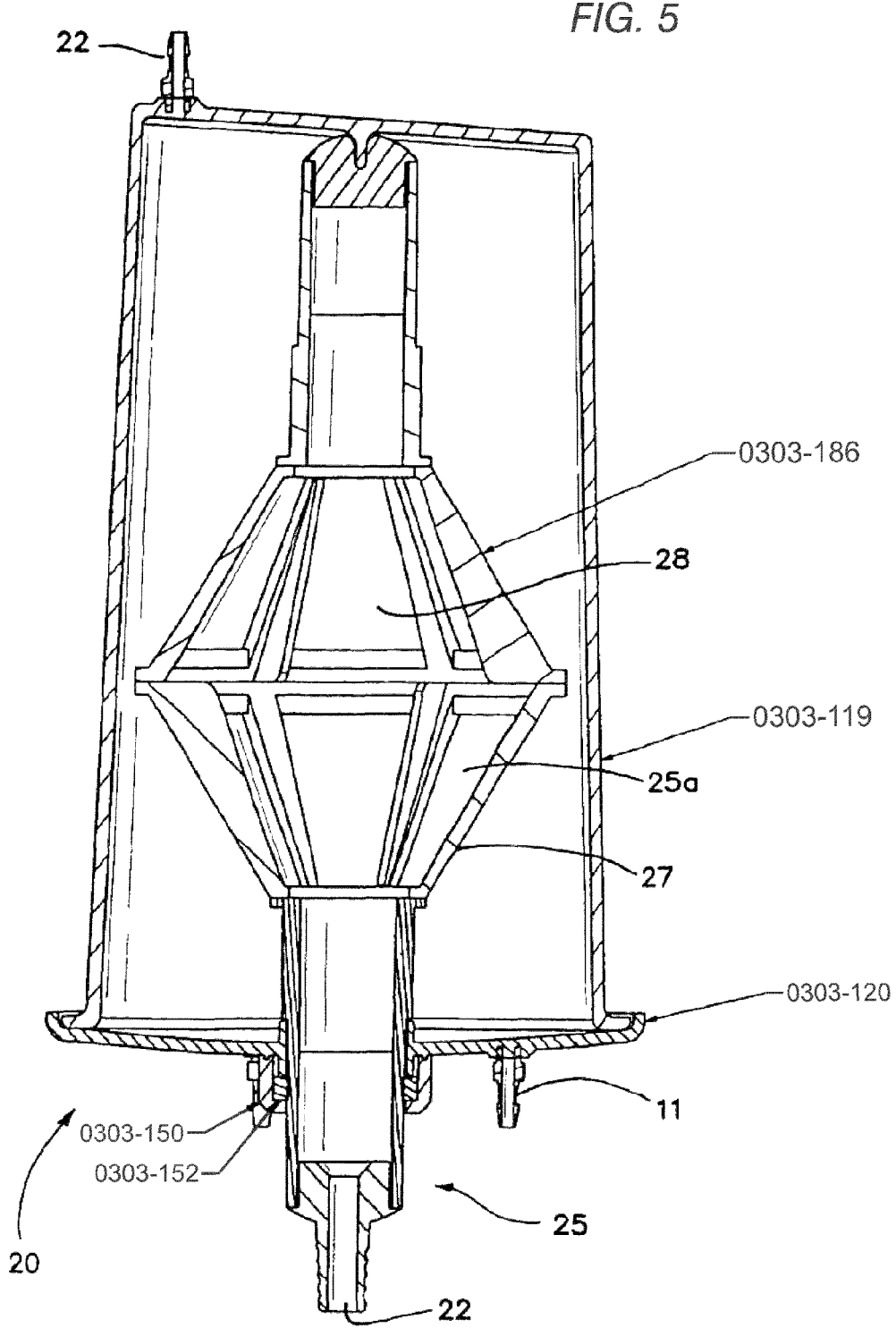
FIG. 5 is a sectional view of a collection chamber including a prefixed filter utilized in a system for separating regenerative cells from tissue.

An exemplary collection chamber 20 of the system, illustrated in FIG. 5, is comprised of a vacuum line 11 which may be used to evacuate air from the chamber which allows the user to remove tissue with a user supplied cannula; an inlet port 21; an outlet port 22 for draining or removing waste; and a rotatable shaft 25 with a paddle-like device wherein the one or more paddles 25*a* are rigidly attached to a filter cage 27 of a prefixed filter 28 for tissue agitation using a magnetic stirrer (not shown).

The system 10 may also be comprised of one or more washing solution sources 22. The washing solution source may comprise a source of saline 23, and a source of a tissue disaggregation agent 24, such as collagenase. The washing solution may be any solution known to one of skill in the art, including saline or any other buffered or unbuffered electrolyte solution. Disaggregation agents that may be used include neutral proteases, collagenase, trypsin, lipase, hyaluronidase, deoxyribonuclease, members of the Blendzyme enzyme mixture family, e.g., Liberase H1, pepsin and/or combinations thereof. The types of tissue being processed will dictate the types or combinations of washing solutions used. Typically, the washing solution, such as saline, enters the collection chamber 20 after the adipose tissue has been removed from the patient. However, the washing solution may be delivered to the collection chamber 20 before the adipose tissue is extracted, or may be delivered to the collection chamber 20 concurrently with the adipose tissue. In the collection chamber 20, the washing solution and the extracted adipose tissue may be mixed by any means including the methods described above.

The containers for the saline 23 and/or the disaggregation agents 24 may be any suitable container that can hold their contents in a sterile manner, e.g., a collapsible bag, such as an IV bag used in clinical settings. These containers may have conduits 12, such as conduit 12*e*, coupled to the collection chamber 20 so that the saline and/or the disaggregation agent may be delivered to the interior of the collection chamber 20. The saline and/or disaggregation agent may be delivered to the interior of the collection chamber 20 through any art-recognized manner, including simple gravity pressure applied to the outside of the containers for the saline 23 and/or the disaggregation agents 24 or by placement of a positive displacement pump on the conduits, e.g., conduit 12*d* in FIG. 4.

The tissue and/or fluid within the collection chamber should be maintained at a temperature ranging from 30 degrees Celsius to 40 degrees Celsius. In a preferred embodiment, the temperature of the suspension inside the collection chamber is maintained at 37 degrees Celsius. In certain embodiments, if the surgical procedure or therapeutic application needs to be delayed, the selected tissue may be stored in the collection chamber for later use. The tissue may be stored at or about room temperature or at about 4 degrees Celsius for up to 96 hours.

To aid in the separation and concentration process, the collection chamber 20 allows for differentiation of buoyant and non-buoyant liquid within the chamber. In automated embodiments of the system, the collection chamber may be comprised of sensors 29 which can detect when the interface between the buoyant and non-buoyant liquids has been reached. For example, the sensor 29 may be an optical sensor which may be capable of detecting a change in the light refraction of the effluent which is flowing in the outlet fluid passageway of the collection chamber and sending a signal to the processing device of the system to thereby activate or de-activate one or more pumps and/or valves in accordance with the processing device associated with the system.

Since the buoyant layer is comprised of the regenerative cells that require further washing and concentrating, the collection chamber 20 is preferably comprised of an outlet port 22 at the lowest point of the chamber such that blood and other non-buoyant components of the tissue may be drained to the waste container. Accordingly, the collection chamber 20 may be coupled to one or more waste containers 40 via one or more conduits 12 described herein to permit waste from the collection chamber to be drained or removed from the system. The draining may be passive or active. For example, the non-buoyant components described above could be drained using gravity, by applying positive or negative pressure, by use of pumps 34 or by use of vents 32. The collection chamber may be positioned such that the outlet ports 22 are positioned at, or near, the bottom of the collection chamber. The collection chamber is preferably positioned in this orientation to allow adipose tissue fragments to float, e.g. from 15 seconds to several minutes or longer. In automated embodiments, the processing device of the system calculates various parameters, e.g., the volume of saline required for washing the tissue and the time required for washing the tissue, based on information initially entered by the user (e.g., volume of tissue being processed). Based on the control logic of the processing device, certain valves and/or pumps are activated or de-activated such that waste from the collection chamber 20 is removed from the system. Sensors 29 such as optical sensors may be placed such that they are capable of signaling the processing device of the system to proceed with the next step in the tissue processing.

In a preferred embodiment, the collection chamber 20 is comprised of a closed fluid pathway that allows saline and reagents to be added to the tissue in an aseptic manner. Accordingly, the collection chamber 20 is further comprised of conduits 12, e.g., flexible or rigid conduits, that are appropriately sized to allow for free passage of tissue and liquid. In a preferred embodiment, the conduits 12 are in the form of tubing. The conduits 12 can vary in size depending on whether passage of fluid or tissue is desired. The conduits 12 may also vary in size depending on the amount of tissue or fluid that is cycled through the system. For example, for the passage of fluid, the conduits may have a diameter ranging from about 0.060 to about 0.750 inches and for the passage of tissue, the conduits may have a diameter ranging from 0.312 to 0.750 inches. Generally, the size of the conduits is selected to balance the volume the conduits can accommodate and the time required to transport the tissue or fluids through said conduits. In automated embodiments of the system, the foregoing parameters, i.e., volume and time for transport, must be identified such that the appropriate signals can be transmitted to the processing device of the system. This allows the device to move accurate volumes of liquid and tissue from one chamber to another.

The collection chamber 20 also allows for removal of the washed adipose tissue to a processing chamber 30. Accordingly, the collection chamber 20 must be connected to the necessary tubing 12, valves 14 and pump 34 for the movement and storage of washed adipose tissue. In addition, the collection chamber 20 typically includes one or more ports 21 for permitting the washing solution to be delivered to the interior of the chamber, and one or more ports 22 for permitting waste and other materials to be directed out from the collection chamber 20. For example, the collection chamber may include one or more sealed entry ports as described herein. The collection chamber 20 may also include one or more caps (not shown), such as a top cap and a bottom cap to further ensure that the system remains sterile while washing solution is delivered into the collection chamber and/or waste is transported out. The ports 21 may be provided on the caps of the collection chamber or on a sidewall of the collection chamber.

The process of washing with fresh wash solution may be repeated until the residual content of non-buoyant contaminants in the solution reaches a pre-determined level. In other words, the remaining material in the collection chamber 20, which comprises the buoyant material of the mixture described above, including adipose tissue fragments, may be washed one or more additional times until the amount of undesired material is reduced to a desired pre-determined level. One method of determining the end point of the washing is to measure the amount of red blood cells in the tissue solution. This can be accomplished by measuring the light absorbed on the 540 nm wavelength. In a preferred embodiment, a range between about 0.546 and about 0.842 is deemed acceptable.

After a desired amount of wash cycles, a tissue disaggregation agent may be delivered to the collection chamber 20 to digest the remaining adipose tissue components. For example, saline, such as saline delivered from a saline source 23 as described above, may be added to the adipose tissue along with or immediately followed by addition of collagenase, such as collagenase delivered from a collagenase source 24 as described above. The washed adipose tissue and the tissue disaggregation agent may then be agitated in manners similar to the agitation methods described above, until the washed adipose tissue is disaggregated. For example, the washed adipose tissue and the tissue disaggregation agent may be agitated by rotating the entire collection chamber through an arc of approximately 90 degrees, by having a shaft which contains one or more paddles which pass through the solution as the shaft is being rotated, and/or by rotating the entire collection chamber which contains paddles or protrusions on the inside surface of the collection chamber.

In one embodiment, the adipose tissue fragments are mixed with a collagenase-containing enzyme solution at or around 37.degree. C. for about 20-60 minutes. In other embodiments, a higher concentration of collagenase or similar agent may be added to decrease the digestion time. Similarly to that described above, the collection chamber 20 may then be placed in an upright position so that the outlet ports 22 are located at the bottom of the collection chamber for a period of time sufficient to allow buoyant cells and tissue fragments to float. Typically, the time may ranges from about 15 seconds to several minutes but other times may be implemented in modified embodiments.

Depending on the purpose for which the adipose derived cells will be used, the adipose tissue may either be partially disaggregated, or completely disaggregated. For example, in embodiments in which the adipose derived cells are to be combined with a unit of adipose tissue, it may be desirable to partially disaggregate the harvested adipose tissue, to remove a portion of the partially disaggregated adipose tissue, and then continue disaggregating the remaining portion of adipose tissue remaining in the collection chamber. Alternatively, a portion of washed adipose tissue may be removed and set aside in a sample container prior to any digestion. In another embodiment, harvested adipose tissue is partially disaggregated to concentrate cells before being reintroduced back into the patient. In one embodiment, the adipose tissue is mixed with a tissue disaggregation agent for a period of time generally less than about 20 minutes. A portion of the partially disaggregated tissue may then be removed from the collection chamber, and the remaining partially disaggregated tissue may be further disaggregated by mixing the adipose tissue with a tissue disaggregation agent for another 40 minutes. When the adipose derived cells are to be used as an essentially pure population of regenerative cells, the adipose tissue may be fully disaggregated.

During the washing and/or disaggregation, one or more additives may be added to the various containers as needed to enhance the results. Some examples of additives include agents that optimize washing and disaggregation, additives that enhance the viability of the active cell population during processing, anti-microbial agents (e.g., antibiotics), additives that lyse adipocytes and/or red blood cells, or additives that enrich for cell populations of interest (by differential adherence to solid phase moieties or to otherwise promote the substantial reduction or enrichment of cell populations). Other possible additives include those that promote recovery and viability of regenerative cells (for example, caspase inhibitors) or which reduce the likelihood of adverse reaction on infusion or emplacement (for example, inhibitors of re-aggregation of cells or connective tissue).

After a sufficient settling time has elapsed, the non-buoyant fraction of the resulting mixture of washed adipose tissue fragments and tissue disaggregation agents will contain regenerative cells, e.g., stem cells and other adipose derived progenitor cells. As discussed herein, the non-buoyant fraction containing the regenerative cells will be transferred to the processing chamber 30 wherein the regenerative cells of interest, such as the adipose derived stem cells, will be separated from other cells and materials present in the non-buoyant fraction of the mixture.

Accordingly, the processing chamber 30 is positioned within the system such that the rinsed and digested tissue suspension moves from the collection chamber 20 to the processing chamber 30 by way of tubing 12, valves 14 and pump 34. The processing chamber is sized to accommodate tissue/fluid mixtures ranging from 10 mL to 1.2 L. In a preferred embodiment, the processing chamber is sized to accommodate 800 mLs. In certain embodiments, the entire regenerative cell composition from the collection chamber 20 is directed to the processing chamber 30. However, in other embodiments, a portion of the regenerative cell composition is directed to the processing chamber 30, and another portion is directed to a different region of the system, e.g., the sample chamber 60, to be recombined with cells processed in the processing chamber 30 at a later time. As previously set forth herein, the regenerative cell composition of the present invention is a composition of cells typically present in a volume of liquid after a tissue, e.g., adipose tissue, is washed and at least partially disaggregated. In other words, the regenerative cell composition that is transferred from the collection chamber 20 after being mixed with a tissue disaggregation agent, comprises multiple different types of cells, including stem cells, progenitor cells, endothelial precursor cells, adipocytes and other regenerative cells described herein. The regenerative cell composition may also contain one or more contaminants, such as collagen and other connective tissue proteins and fragments thereof, which were present in the adipose tissue fragments, or residual collagenase from the tissue disaggregation process.

Figure 6:
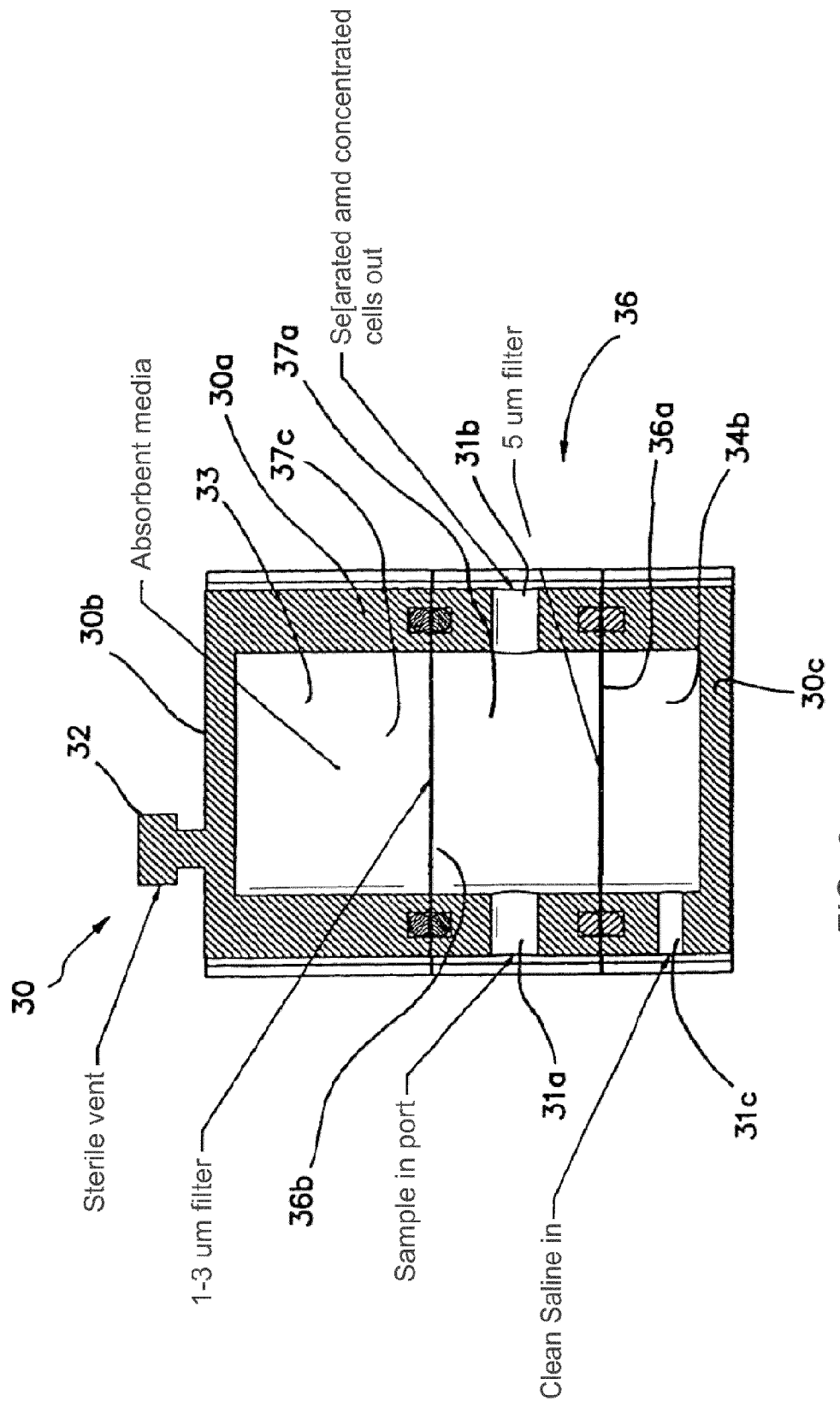
FIG. 6 is a sectional view of a processing chamber of a system for separating regenerative cells from tissue utilizing a percolative filtration system.

The processing chamber 30 may be constructed using any suitable biocompatible material that can be sterilized. In a preferred embodiment, the processing chamber 30 is constructed of disposable material that meets biocompatibility requirements for intravascular contact, as described in the ISO 10993 standard. For example, polycarbonate, acrylic, ABS, ethylene vinyl acetate or styrene-butadiene copolymers (SBC) may be used. In another embodiment, the fluid path of the disposable processing chamber is pyrogen free. The processing chamber may be in the form of a plastic bag, such as those conventionally used in processing blood in blood banks; or in other embodiments, it may be structurally rigid (FIG. 6). In one embodiment, the processing chamber 30 may be similar to the processing chamber disclosed in commonly owned U.S. application Ser. No. 10/316,127, filed Dec. 7, 2001 and U.S. application Ser. No. 10/325,728, filed Dec. 20, 2002, the contents of which in their entirety are hereby incorporated by reference.

In certain embodiments, the regenerative cell composition from the collection chamber 20 is introduced into the processing chamber 30 where the solution can be filtered to separate and/or concentrate a particular regenerative cell composition. Cell filtration is a method of separating particular components and cells from other different components or types of cells. For example, the regenerative cell composition of the invention comprises multiple different types of cells, including stem cells, progenitor cells and adipocytes, as well as one or more contaminants, such as collagen, which was present in the adipose tissue fragments, or residual collagenase from the tissue disaggregation process. The filters 36 present in the processing chamber 30 may allow for separation and concentration of a particular subpopulation of regenerative cells, e.g., stem cells or endothelial progenitors cells etc.

Some variables which are associated with filtration of cells from a liquid include, but are not limited to, pore size of the filter media, geometry (shape) of the pore, surface area of the filter, flow direction of the solution being filtered, trans-membrane pressure, dilution of the particular cell population, particulate size and shape as well as cell size and cell viability. In accordance with the disclosure herein, the particular cells that are desired to be separated or filtered are typically adipose derived stem cells. However, in certain embodiments, the particular cells may include adipose derived progenitor cells, such as endothelial precursor cells, alone or in combination with the stem cells.

Figure 2:
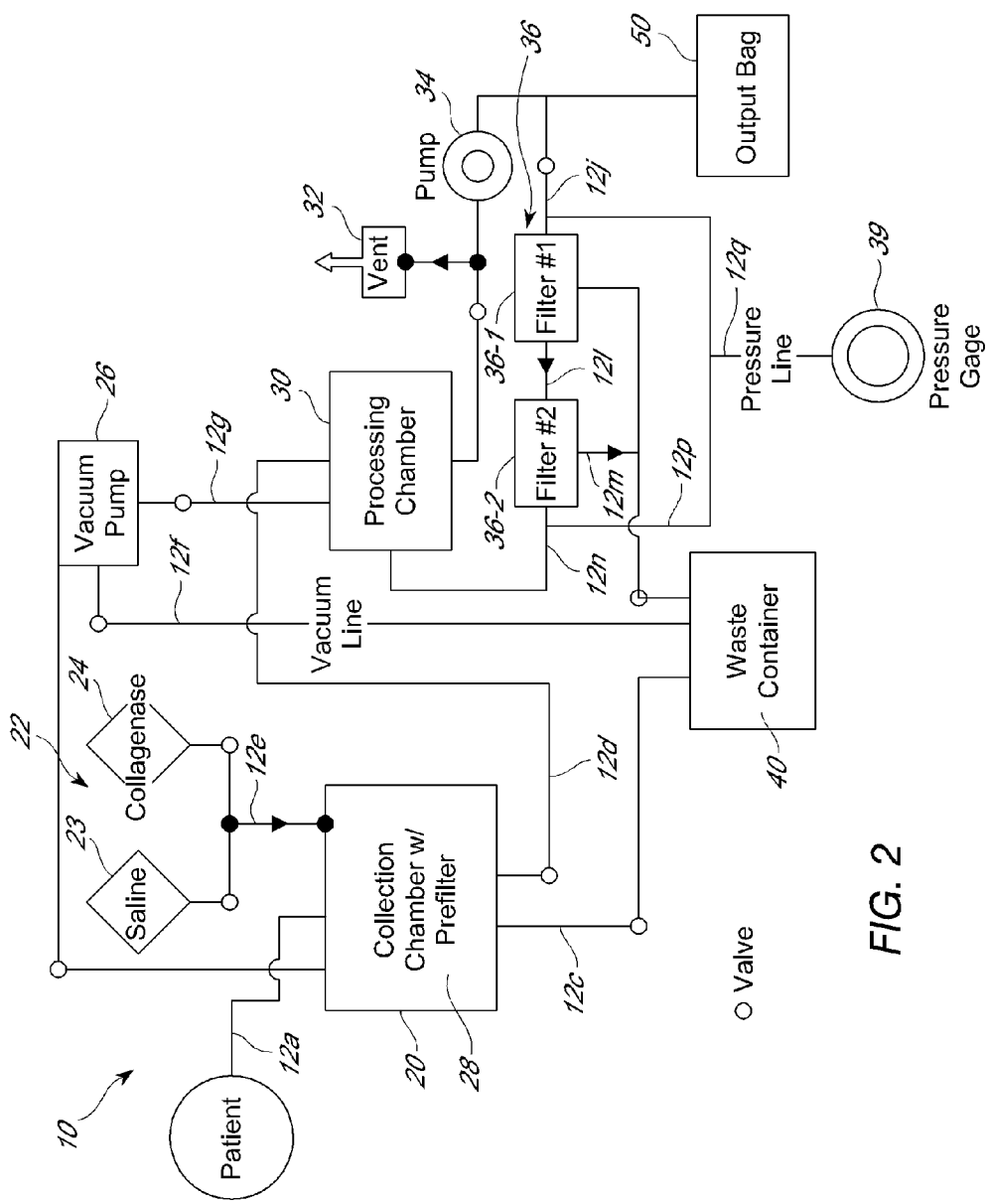
FIG. 2 is an illustration of a system similar to FIG. 1 having a plurality of filter assemblies in a serial configuration.
Figure 3:
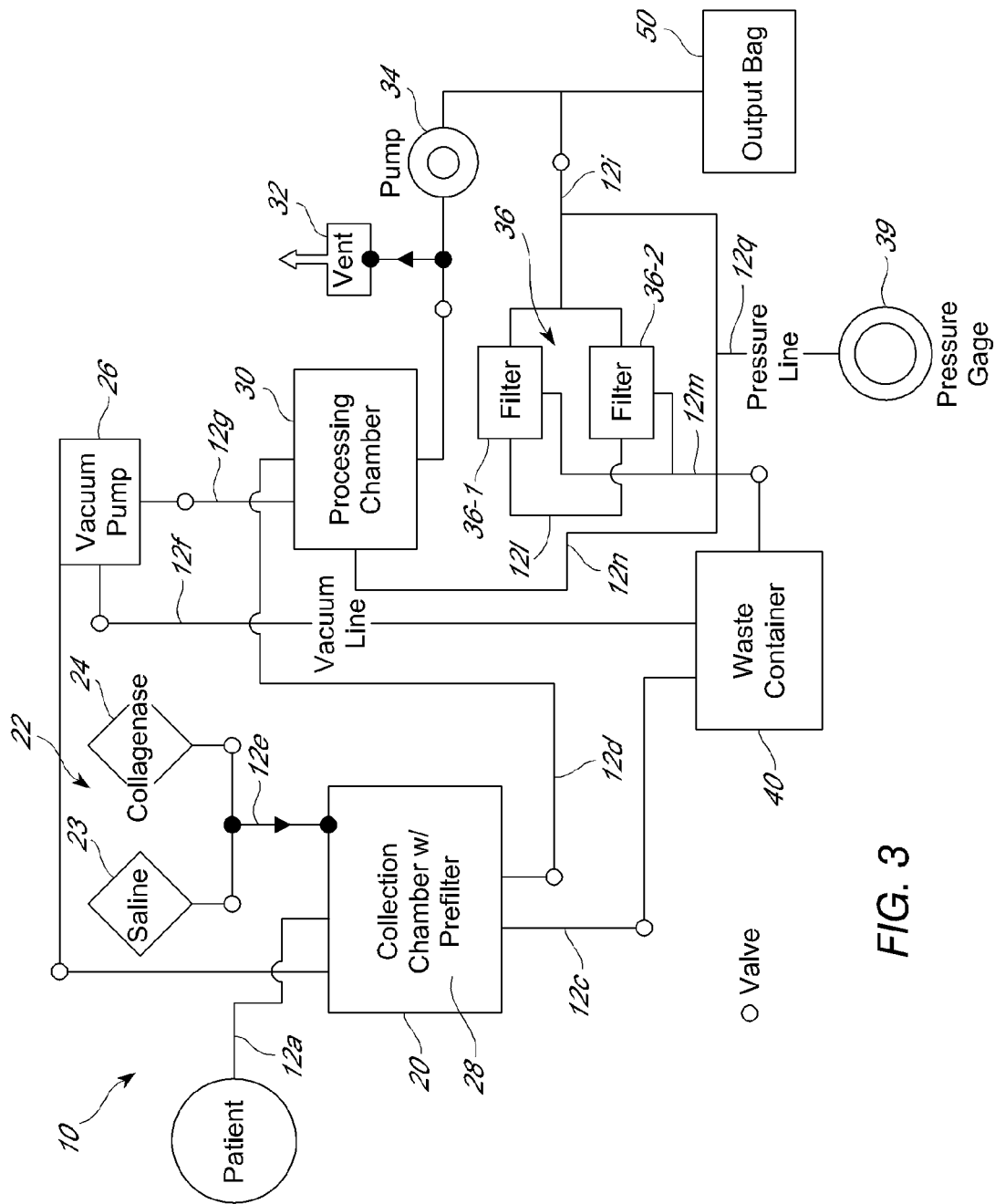
FIG. 3 is an illustration of a system similar to FIG. 1 having a plurality of filter assemblies in a parallel configuration.

The regenerative cell composition may be directed through a filter assembly, such as filter assembly 36. In certain embodiments, the filter assembly 36 comprises a plurality of filters which are structured to perform different functions and separate the regenerative cell composition into distinct parts or components. For example, one of the filters may be configured to separate collagen from the regenerative cell composition, one of the filters may be configured to separate adipocytes and/or lipid components from the regenerative cell composition, and one of the filters may be configured to separate residual enzymes, such as the tissue disaggregation agent, from the regenerative cell composition. In certain embodiments, one of the filters is capable of performing two functions, such as separating collagen and the tissue disaggregation agent from the composition. The plurality of filters are typically serially arranged; however, at least a portion of the filters may be arranged in parallel, as well. A serial arrangement of the filters of the filter assembly 36 is shown in FIG. 2. A parallel arrangement of the filters of the filter assembly 36 is shown in FIG. 3.

In one embodiment, the filter assembly 36 comprises a first filter, a second filter, and a third filter. The first filter is configured to remove collagen particles present in the regenerative cell composition. These collagen particles are typically approximately 0.1 microns in diameter and can be up to 20 microns long. The collagen particles may be of varying sizes depending on the digestion. They also may be fibrils, meaning they have twists and turns. Any of the filters described herein may be made from polyethersulfone, polyester, PTFE, polypropylene, PVDF, or possibly cellulose. There are two possibilities for filtering the collagen. One is to try to remove the larger particles first, letting the cells go through, which would require for example a filter probably in the 10 micron range. The second method is to use a smaller size filter, such as 4.5 micron, with the intent that the collagen would be well digested, so as to trap the cells, and let the collagen pass through. This would require a means to float the cells back off the filter. There may also be a possibility of implementing a filter which would attract and hold the collagen fibers.

The second filter is configured to remove free immature adipocytes which are not buoyant in the regenerative cell composition. In one embodiment the second filter can be constructed of polyester and have a pore size between about 30 and about 50 microns with a preferred pore size being about 40 microns. Although referred to as a second filter, placement of such a device may be in a first, rather than second, position to facilitate an initial removal of larger cells and particles. The third filter is configured to remove the unused or residual collagenase or other tissue disaggregation agent present in the composition. In a preferred implementation, the collagenase may degenerate over time. In one embodiment, the third filter comprises a plurality of pores having a diameter, or length less than 1 In certain embodiments, the pores may have diameters that are smaller than 1 In other embodiments, the pores have diameters between 10 kD and 5 microns. In certain embodiments, the third filter may be configured to concentrate the regenerative cell population into a small volume of saline or other washing solution, as discussed herein. As presently preferred, only the final filter is the hollow fiber unit. It is not necessary for any of the filters to be of the hollow fiber type. The hollow fiber unit is used for the final filter in a preferred implementation because it is the most efficient in removing the collagenase with the smallest detrimental effect to the regenerative cells. In an embodiment wherein the device is a collection of off the shelf items, the three filters are in separate housings. It is feasible to have the first and second filters combined into one housing if a hollow fiber unit is used for the third filter. If the final filter is not a hollow fiber set-up then all three filters can be contained in one housing.

The filters of the filter assembly 36 may be located in the processing chamber 30 or may be provided as components separate from the processing chamber 30. In addition, the filters of the filter assembly 36 may be provided in multiple processing chambers or in an inline fashion. In certain embodiments, the conduits or tubing may act as a processing chamber or chambers. The processing chamber can be reduced in size such that it becomes the inside volume of the conduits which connect the filters. This type of system will function correctly if the volume of tissue solution is sized appropriately. Thus, the conduits may act as the processing chamber by containing the fluid with cells as it is being run through the filters. Care may be taken to minimize the volume of the conduits so that cells/tissue are not unnecessarily lost in the process of priming and running the system.

Referring to the embodiment described above, the regenerative cell composition, containing the washed cells and residual collagen, adipocytes, and/or undigested tissue disaggregation agent, may be directed through the first filter to remove at least a portion of and preferably substantially all of the collagen particles from the composition so that fewer, and preferably no, collagen particles are present in the filtered solution. The filtered regenerative cell composition containing the adipocytes and/or undigested tissue disaggregation agent, may then be directed through the second filter to remove at least a portion of and preferably substantially all of the free adipocytes from the filtered regenerative cell composition. Subsequently, the twice filtered regenerative cell composition, containing the undigested tissue disaggregation agent, may be directed through the third filter, such as a hollow fiber filtration device, as discussed herein, to remove or reduce the undigested tissue disaggregation agent from the regenerative cell composition.

The thrice-filtered regenerative cell composition (i.e., the composition remaining after being passed through the first, second, and third filters) may then be directed to multiple outlets, which may include a portion of the processing chamber 30 comprising multiple outlets. These outlets can serve to maintain the necessary pressure, as well as to provide connections via conduits to other containers which may include the collection chamber 20, the output chamber 50, and/or the waste container 40.

In one embodiment, a filter of the filter assembly 36 comprises a hollow-fiber filtration member. Or, in other words, the filter comprises a collection of hollow tubes formed with the filter media. Examples of filter media which can be used with the disclosed system 10 include polysulfone, polyethersulfone or a mixed ester material, and the like. These hollow fibers or hollow tubes of filter media may be contained in a cylindrical cartridge of the filter assembly 36. The individual tubes or fibers of filter media typically have an inside diameter which ranges from about 0.1 mm to about 1 mm with a preferred value being about 0.5 mm. The diameter and length of a suitable cylindrical cartridge will determine the number of individual tubes of filter media which can be placed inside the cartridge. One example of a suitable hollow fiber filter cartridge is the FiberFlo® Tangential Flow Filter, catalog #M-C-050-K (Minntech, Minneapolis, Minn.). Pore sizes of the filter media can range between about 10 kiloDaltons and about 5 microns with a preferred pore size being about 0.5 microns.

Figure 12A:
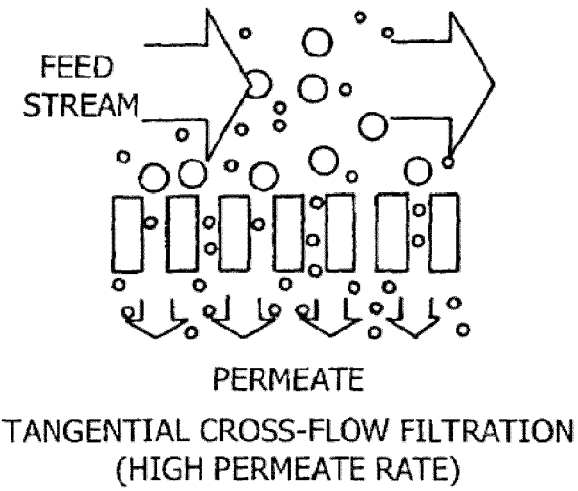
FIG. 12A illustrates a filtration process in which the feed stream of fluid flows tangentially to the pores of the filter.

In the hollow-fiber filter, each hollow tube has a body with a first end, a second end, and a lumen located in the body and extending between the first end and second end. The body of each hollow tube includes a plurality of pores. The pores are generally oriented in the body so that a regenerative cell composition is filtered by flowing through the lumen of the body, and the products to be filtered tangentially pass through the pores, as shown in FIG. 12A. In other words, the smaller particles in the liquid pass tangentially through the pores relative the flow of fluid through the lumen of the body. The composition with the regenerative cells passes through the lumen of each hollow tube when the composition is being filtered. Preferably, the flow of the composition is tangential to the pores of the body of each hollow tube.

Figure 12B:
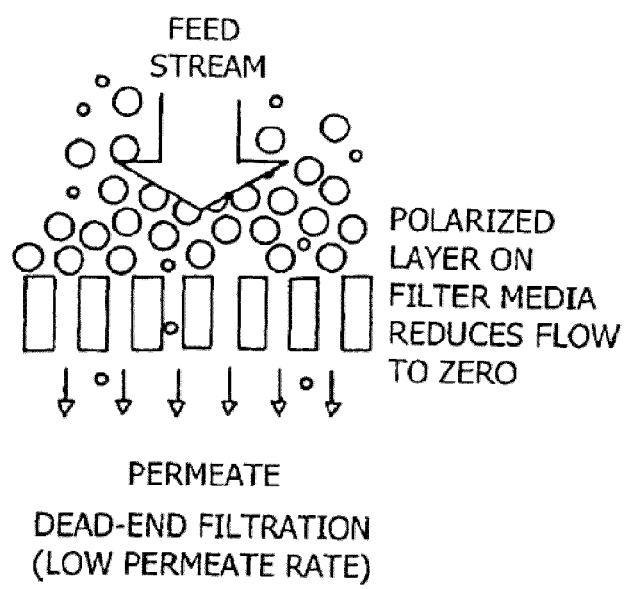
FIG. 12B illustrates a filtration process in which the feed stream of fluid flows perpendicular to the pores of the filter.

By using a tangential flow of fluid, the efficiency of filtration of the stem cells may be enhanced relative to other filtration techniques. For example, in accordance with some filtration techniques, the pores of the filter media are placed in such a manner that the filter is orientated perpendicular to the flow of the fluid so that the Filter media blocks the path of the fluid being filtered, as illustrated in FIG. 12B. In this type of filtration, the particles which are being filtered out of the regenerative cell composition, e.g., the stem cells, tend to build up on one side of the filter and block the flow of the fluid through the pores. This blockage can reduce the efficiency of the filter. In addition, the cells are constantly compressed by the pressure of the fluid flow as well as the weight of the cells accumulating on the upstream side of the filter. This can lead to increased lysis of stem cells. Thus, in such filtration techniques wherein the flow of fluid is parallel to the orientation of the pores in the filter, both large cells and small particles can be undesirably directed against the filter media as the fluid is passed through the pores. Consequently, larger products in the liquid such as cells may block the pores, thereby decreasing the filtering effect and increasing an occurrence of cell rupture or injury.

In contrast, in the hollow fiber configuration of the present system 10, the fluid which is being filtered flows inside the lumen of the hollow tube. The portion of the fluid which has the ability to pass through the pores of the body of the filter does so with the aid of the positive pressure of the fluid on the inside of the body as well as a negative pressure which is applied on the outside of the body. In this embodiment, the cells typically are not subjected to the pressure of the fluid flow or the weight of other cells, and therefore, the shear forces on the stem cells are reduced Thus, the efficiency and effectiveness of the filtration can be enhanced by the reduction in clogging rates and the reduction in regenerative cell lysis. Due to the size of the saline and unwanted protein molecules, during filtration, these molecules and other small components pass through the pores of the bodies of the hollow tubes to the outside of the hollow tubes and are directed to the waste container 40. In one embodiment, filtration is enhanced by generating a vacuum on the outside of the hollow tube filter media. Due to the size of the regenerative cells, e.g., stem cells or progenitor cells, these cells typically cannot pass through the pores of the body and therefore remain on the inside of the hollow tube filter (e.g., in the lumens of the tubes) and are directed back to the processing chamber 30 via a conduit between the filter and the processing chamber, or to the output chamber 50.

In one specific embodiment, the hollow fiber filter has about a 0.05 micron pore size, and contains approximately 550 $cm^2$ surface area of filter media. An individual media tube typically has a diameter of about 0.5 mm. In processing 130 ml of the regenerative cell composition, approximately 120 ml of additional saline may be added to the composition. The processing or filter time may be approximately 8 minutes. The differential of the pressures on either side of the body of the hollow fiber tube (e.g., the pressure inside the lumen of the body, and outside the body) is considered the trans-membrane pressure. The trans-membrane pressure can range from about 1 mmHg to about 500 mmHg with a preferred pressure being about 200 mmHg. The average nucleated cell recovery and viability using hollow fiber filtration can be approximately 80% of viable cells.

The amount of collagenase which is typically removed in such a system equates to a three log reduction. For example if the initial concentration of collagenase in the regenerative cell composition which is transferred from the collection chamber to the processing chamber is 0.078 U/ml the collagenase concentration of the final regenerative cell composition would be 0.00078 U/ml. The collagenase is removed in the hollow fiber filter, and the hollow fiber filter corresponds to the third filter discussed above.

Processing chambers illustrating one or more cell filtration methods described above are shown in the Figures, particularly FIGS. 1-3. With reference to FIGS. 1-3, between the processing chamber 30 and the filtering chamber of the filter assembly 36, a pump may be provided, such as pump 34. In addition, vent and pressure sensors, such as vent 32, and pressure sensor 39, may be provided in line with the processing chamber 30 and the filter assembly 36. Fittings for the output chamber 50 may also be provided. These optional components (e.g., the pump 34, the vent 32, the pressure sensor 39, and the fittings for the output chamber 50) may be provided between the processing chamber 30 and the filter assembly 36 so that liquid contained in the processing chamber 30 may flow to one or more of these optional components before flowing through the filter assembly 36. For example, liquid may flow through the pump 34 before it is passed to the filter assembly 36. Or, liquid may pass through the pressure sensor 39 before passing through the filter assembly to obtain a pre-filter liquid pressure in the system. In certain situations, one or more of these components may also be provided as an element of the processing chamber 30, such as the vent 32 as illustrated in FIG. 6. In the illustrated embodiment, the pressure sensor 39 is in line to determine the pressure of the regenerative cell composition which is generated by the pump 34 as it enters the filtering chamber of the filter assembly 36. This construction can facilitate monitoring of the trans-membrane pressure across the filter membrane. Additional saline or other buffer and washing solution can be added to the regenerative cell composition to assist in the removal of unwanted proteins as the composition is being filtered through the filter assembly 36. This repeated washing can be performed multiple times to enhance the purity of the regenerative cell composition. In certain embodiments, the saline can be added at any step as deemed necessary to enhance filtration.

In one specific embodiment, which is provided by way of example and not limitation, the unwanted proteins and saline or other washing solution is removed in the following manner. The composition with the regenerative cells, as well as collagen and connective tissue particles or fragments, adipocytes, and collagenase, is cycled through a series of filters until a minimum volume is reached. The minimum volume is a function of the total hold up volume of the system and some predetermined constant. The hold up volume is the volume of liquid which is contained in the tubing and conduits if all of the processing chambers are empty. In one embodiment, the minimum volume is 15 ml. When the minimum volume is reached, a predetermined volume of washing solution is introduced into the system to be mixed with the regenerative cell composition. This mixture of washing solution and the regenerative cell composition is then cycled through the filters until the minimum volume is reached again. This cycle can be repeated multiple times to enhance the purity of the regenerative cells, or in other words, to increase the ratio of regenerative cells in the composition to the other materials in the composition. See FIGS. 10 and 11.

After it has been determined that the regenerative cell composition has been cleansed of unwanted proteins and concentrated sufficiently (in exemplary embodiments, minimum concentrations within a range of about $1 \times 10$ to about $1 \times 10^7$ cells/ml can be used and, in a preferred embodiment the minimum concentration can be about $1 \times 10^7$ cells/ml), an output chamber 50, such as an output bag, may be connected to an outlet port of the processing chamber 30 and/or the filter assembly 36, depending on the specific embodiment. A vent, such as the vent 32, may then be opened to facilitate the output of the concentrated regenerative cells. In one implementation, this determination of when a minimum concentration has been reached is made empirically after experiments have been run and programmed into the electronic controls of the device. The determination can be an input into the process of what is desired to yield, i.e., how many stem/progenitor cells are desired, or range of cell concentration. Based on scientific data, a predefined amount of adipose tissue needs to be obtained and placed into the system to achieve the desired output. With the vent 32 open, a pump, such as the pump 34, can function to transfer the concentrated regenerative cells into the output bag. In one embodiment, the output bag 50 is similar to an empty blood bag which has a tube with a fitting on one end. In a sterile fashion, the fitting on the output bag may be attached to the outlet port, and the concentrated regenerative cells may be transferred to the output bag.

As illustrated in FIGS. 1-3, a vacuum pump 26 may be provided in the system 10 to change the pressure in the system, among other things. For example, the vacuum pump 26 may be coupled to the collection chamber 20 via a conduit, such as conduit 12b, to cause a decrease in pressure within the collection chamber 20. Vacuum pump 26 may also be coupled to the processing chamber 30 by way of a conduit, such as conduit 12g. Regarding the operation of vacuum pump 26 in connection with pump 34, two separate vacuum pumps or sources may be implemented, or a single one may be implemented by using valves which direct the vacuum pull to the different conduits that need it at specific points in the process. In addition, vacuum pump 26 may be coupled to the waste container 40 via a conduit, such as conduit 12f.

Figure 10:
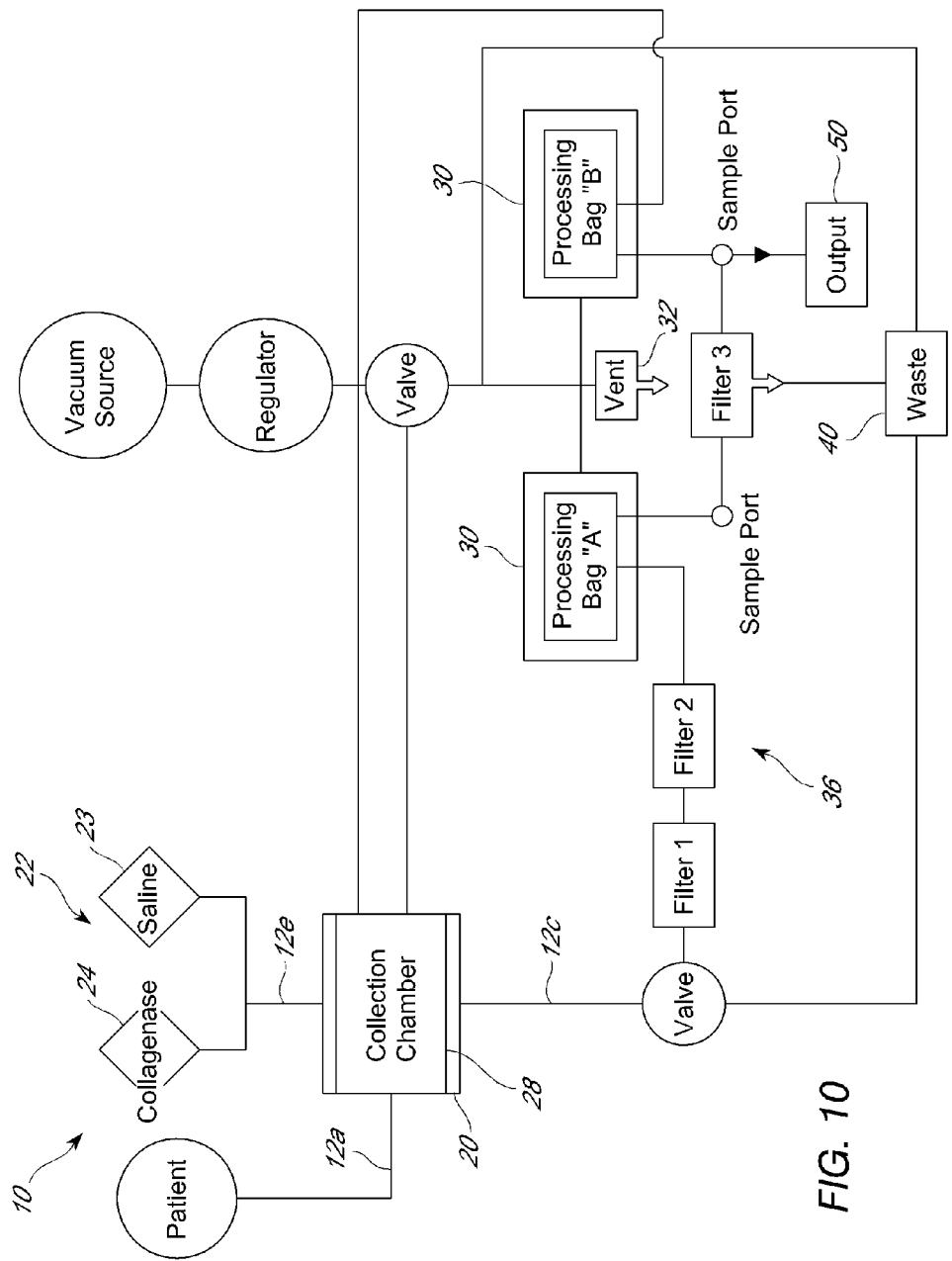
FIG. 10 is an illustration of a system for separating regenerative cells from tissue utilizing vacuum pressure to move fluids through the system. A vacuum system can be constructed by applying a vacuum pump or vacuum source to the outlet of the system, controlled at a predetermined rate to pull tissue and fluid through, using a system of stopcocks, vents, and clamps to control the direction and timing of the flow.
Figure 11:
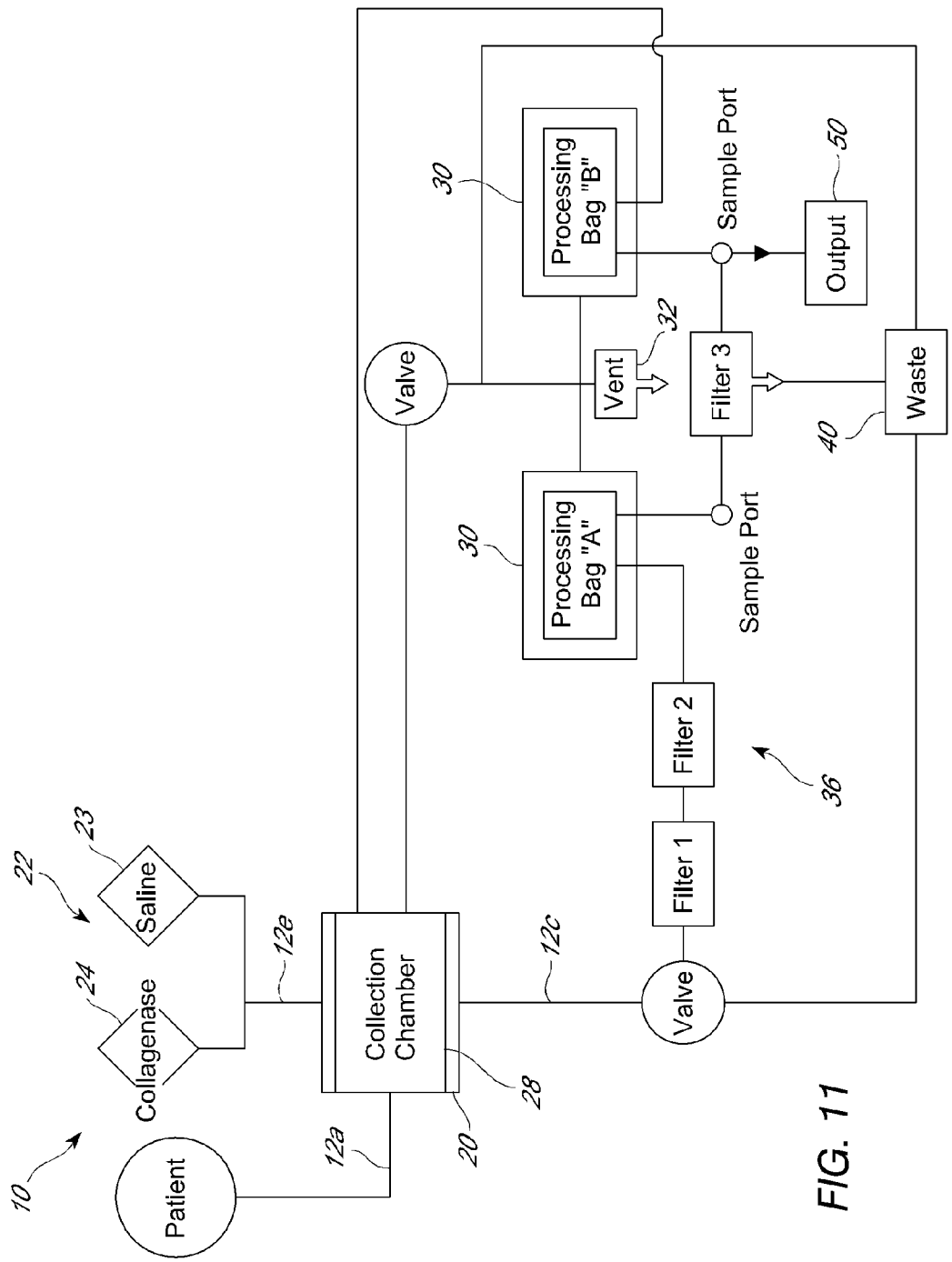
FIG. 11 is an illustration of a system for separating regenerative cells from tissue utilizing positive pressure to move fluids through the system. A positive pressure system uses a mechanical means such as a peristaltic pump to push or propel the fluid and tissue through the system at a determined rate, using valves, stopcocks, vents, and clamps to control the direction and timing of the flow.

With reference to FIGS. 10 and 11, the pressure generated by the vacuum pump 26 can be used to direct the flow of fluids, including the regenerative cells, through the conduits 12. This pressure can be supplied in multiple directions, for example, by automatically or manually controlling the position of one or more valves 14 in the system 10. The system 10 can be made to function properly with the use of positive pressure or through the use of negative pressure, or combinations thereof. For instance, the regenerative cells can be pulled through the first and second filters described above into a soft sided container which is connected to the third filter. The soft-sided container can be in line (serial) connected ahead of the third filter. The final output chamber may be a soft sided container which is on the other side (e.g., the downstream side) of the third filter. In this embodiment, pressure is used to move the regenerative cells from one soft sided container to a second soft sided container through the filter.

In another embodiment of the system 10, the filtration of the stem cells and/or adipose derived progenitor cells may be accomplished using a combination of percolative filtration and sedimentation. For example, such a system uses saline that is passed through a tissue regenerative cell composition (e.g., the composition containing the stem cells and/or adipose derived progenitor cells) and then through a filter. Some of the variables which are associated with percolative filtration of cells from a regenerative cell composition include, but are not limited to, pore size of the filter media, pore geometry or shape, surface area of the filter, flow direction of the regenerative cell composition being filtered, flow rate of the infused saline, trans-membrane pressure, dilution of the cell population, cell size and viability.

In one embodiment of the system 10, the processing chamber 30 uses a filter assembly 36 which implements percolative filtration and sedimentation to separate and concentrate the regenerative cells. By way of example, and not by way of limitation, the processing chamber 30 is defined as a generally cylindrical body having a sidewall 30a, a top surface 30b, and a bottom surface 30c, as shown in FIG. 6. A sterile vent 32 is provided in the top surface 30b.

In the embodiment of FIG. 6, the processing chamber 30 is illustrated as including a filter assembly 36, which includes two filters, such as large pore filter 36a, and small pore filter 36b. The pore sizes of the filters 36a and 36b typically are in a range between about 0.05 microns and about 10 microns. The large pore filter 36a may comprise pores with a diameter of about 5 and the small pore filter 36b may comprise pores with a diameter of about 1-3 μm. In one embodiment, the filters have a surface area of about 785 mm². Filters 36a and 36b divide an interior of the processing chamber 30 to include a first chamber 37a, a second chamber 37b, and a third chamber 37c. As shown in FIG. 6, first chamber 37a is located between second chamber 37b and third chamber 37c. In addition, first chamber 37a is shown as being the region of the processing chamber 30 having an inlet port 31a and an outlet port 31b. The illustrated processing chamber 30 includes a plurality of ports providing communication paths from an exterior of the processing chamber 30 to the interior of the processing chamber 30, such as ports 31a, 31b, and 31c. The ports 31a, 31b, and 31c, are illustrated as being disposed in the sidewall 30a of a body of the processing chamber 30. However, the ports 31a, 31b, and 31c could be positioned in other regions, as well. Port 31a is illustrated as a sample inlet port, which is constructed to be coupled to a conduit so that a composition containing regenerative cells can be passed into the interior of the processing chamber 30. Port 31b is illustrated as an outlet port constructed to be coupled to a conduit so that the separated and concentrated cells may be removed from the interior of the processing chamber 30. Port 31c is illustrated as an inlet port constructed to be coupled to a conduit for delivery of a fresh washing solution, such as saline into the interior of the processing chamber 30.

In use, the regenerative cells may be introduced into the central chamber 37a via inlet port 31a. Saline or other buffer is introduced into the bottom chamber 37b through inlet port 31c. The saline may be directed through the regenerative cell composition in chamber 37a at a rate of about 10 ml/min. The flow rate of the saline is such that it counteracts the force of gravity. The flow of saline gives the cells in the chamber the ability to separate based on the density of the cells. Typically, as the saline is forced up through the composition the larger cells in the composition will settle to the bottom of the central chamber 37a, and the smaller cells and proteins will be carried away through the second filter 36b into the top chamber 37c. This filtering is accomplished by adjusting the flow rate of the saline such that the larger cells are rolled in place which allows the smaller particles to be liberated and carried off with the saline. The sterile vent 32 is included in the chamber 30 to ensure that the correct pressure gradient is maintained in the three chambers within the processing unit. The upper chamber 37c can comprise an absorbent media 33. The purpose of the absorbent media is to trap the unwanted proteins in the solution to ensure that they do not cross the filter media back into the processing solution, if, for example, the saline flow rate decreases. An absorbent media can be a type of filter material that is absorbent, or attracts materials or components to be filtered out. An outflow port can be added above the top filter to help draw off the waste. Another embodiment of this may be to apply a gentle vacuum from the top to help pull off waste. Absorbent media can be implemented when, as in the illustrated embodiment, the flow rates are relatively small. Excess saline and proteins are then carried away to a waste container.

When the larger cells, (e.g., the adipose derived stem cells and/or progenitor cells) have been sufficiently separated from smaller cells and proteins, the composition containing the separated cells may be concentrated, as discussed herein. The composition may be further concentrated after it has been removed from chamber 37a through outlet port 31b, or while it is in the chamber 37a. In one embodiment, the concentration of cells in the composition is increased in the following manner. After the cells have been sufficiently separated the filters, such as filters 36a and 36b, may be moved towards each other. This movement has the effect of reducing the volume between the two filters (e.g., the volume of chamber 37a). A vibrating member may also be provided in connection with the processing chamber 30 to facilitate concentrating of the cells in the composition. In one embodiment, the vibrating member may be coupled to the filter 36b (e.g., the small pore filter). Vibrating can reduce an incidence of cells becoming trapped in the filters. The reduction in volume of the composition allows the excess saline to be removed as waste and the cells to be concentrated in a smaller volume.

In another embodiment, the concentration of the regenerative cells is accomplished in the following manner. After the cells have been sufficiently separated, the regenerative cell composition can be transferred to another chamber (not shown) which uses gravity to filter out the excess saline. In a preferred embodiment, the sedimentation can occur at the same time as the percolation. This sedimentation may be accomplished by introducing the composition on top of a filter which has a pore size ranging from about 10 kD to about 2 microns. In one embodiment, a suitable filter has a pore size of about 1 micron. The force of gravity will allow the saline and smaller particles to be passed through the filter while preventing the cells in the composition to flow through the filter. After the desired concentration of cells has been obtained, and after the filtered smaller particles have been removed from below the filter, the regenerative cell composition may be agitated to remove the cells from the filter and, subsequently, the concentrated regenerative cells may be transferred to the output bag. The smaller particles can be drawn off as waste through an outlet.

Figure 7:
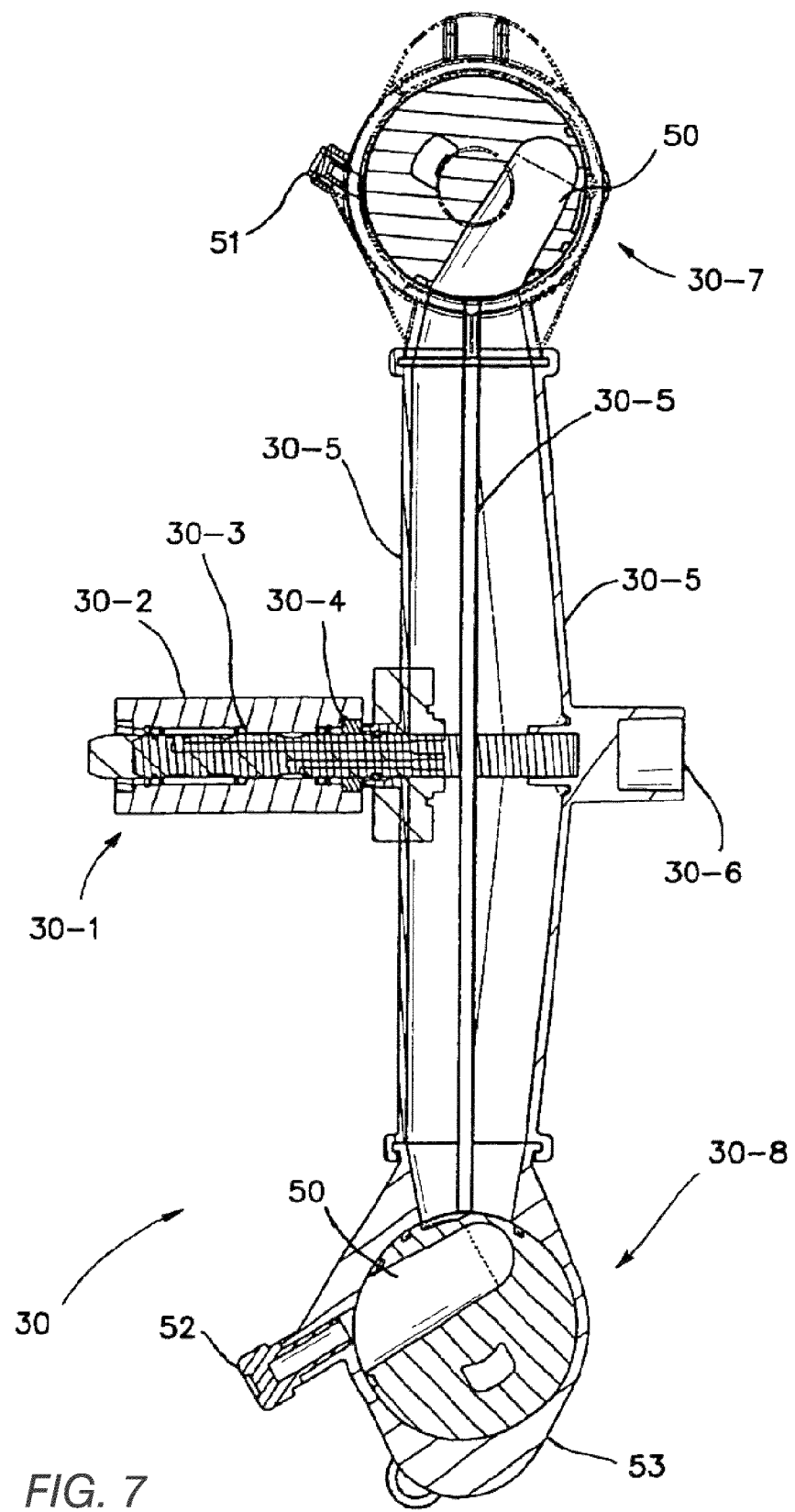
FIG. 7 is a sectional view of a processing chamber of a system for separating regenerative cells utilizing a centrifuge device for concentrating the regenerative cells.
Figure 8:
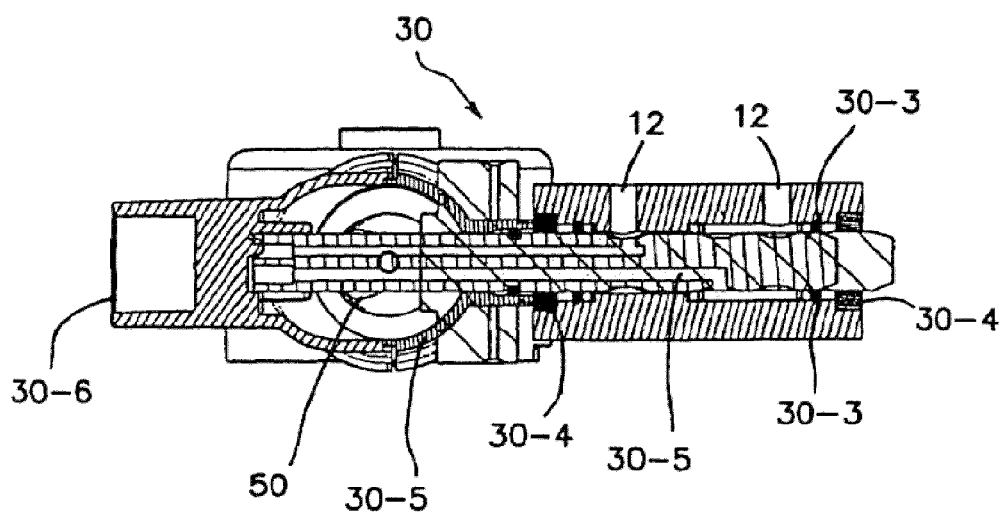
FIG. 8 is another sectional view of the processing chamber of FIG. 7.

In a particular embodiment of the invention, the processing chamber is comprised of a centrifuge chamber or a cell concentrator (FIGS. 4, 7 and 8) that facilitates separation of the regenerative cells from the regenerative cell composition. For example, the cell concentrator may be a centrifuge device or part of a centrifuge device that may separate regenerative cells from the regenerative cell composition based on, e.g., size or density (FIGS. 7 and 8). The cell concentrator may also be a spinning membrane filter.

Centrifugation is recognized in the art as a means for separating and concentrating solutions having multiple components of varying densities. This is done by imparting a centripetal force on the solution which is, for example, higher than gravity. The imparted force causes the tissue solution to separate based on the cell and or particle density. After the cells have been sufficiently concentrated the excess saline and proteins may be removed. Some of the variables which are associated with centrifugation separation of the cells from the solution include, but are not limited to, speed of the rotor, distance of the solution from the center of rotation, and time.

The centrifuge device may be a component of the processing chamber 30, or may be separate from the processing chamber. The centrifuge device may also be partially within the processing chamber and partially separate from the processing chamber (see FIGS. 14 and 15). Typically, the centrifuge device causes a container containing the cell solution, e.g., an output chamber 50, to spin around an axis thereby increasing the force on the cells in the solution to be greater than gravity. The denser or heavier materials in the solution typically settle to one end of the output chamber 50 to form a pellet. The pellet may then be re-suspended to obtain a solution with a desired concentration of cells and/or a desired volumes of cells and medium.

In other embodiments, the processing chamber 30 itself may be in the form of a centrifuge chamber or cell concentrator. Generally, such a processing chamber is constructed to separate and concentrate cells using both centrifugal and gravitational forces. Specifically, during centrifugation, centrifugal force directs the denser components of the regenerative cell composition, e.g., the regenerative cells, towards the outermost ends of the centrifuge chamber. As the centrifuge chamber slows down and eventually stops, gravitational force helps the regenerative cells to remain in the outermost ends of the centrifuge chamber and form a cell pellet. Accordingly, the unwanted components of the regenerative cell composition, i.e., the waste, can be removed without disturbing the cell pellet.

In a further embodiment of the centrifugation process, centrifugal elutriation may also be applied. In this embodiment, the cells may be separated based on the individual cell sedimentation rate such that the directional (e.g., outward)

force applied by centrifugation causes cells and solutes to sediment at different rates. In elutriation, the sedimentation rate of the target cell population is opposed by an opposite (e.g., inward) flow rate applied by pumping solution in the opposite direction to the centrifugal force. The counterflow is adjusted so that the cells and particles within the solution are separated. Elutriation has been applied in many instances of cell separation (Inoue, Carsten et al. 1981; Hayner, Braun et al. 1984; Noga 1999) and the principles and practices used to optimize flow and centrifugal parameters can be applied herein in light of the present disclosure by one skilled in the art.

FIG. 9 illustrates principles associated with an elutriation implementation in accordance with the present invention. The elutriation embodiment can be similar to a centrifugation implementation to the extent that a force is applied to the solution using a spinning rotor. Some of the variables which are associated with the presently embodied elutriation separation include, but are not limited to, the size and shape of the spinning chamber, the diameter of the rotor, the speed of the rotor, the diameter of the counter flow tubing, the flow rate of the counter flow, as well as the size and density of the particles and cells which are to be removed-from solution. As in centrifugation, the regenerative cells can be separated based on individual cell densities.

In one embodiment the regenerative cell composition, e.g., the solution containing the regenerative cells and the collagenase, is introduced into a chamber of a spinning rotor, as shown in FIG. 9A. After the solution is added to the chamber additional saline is added to the chamber at a predetermined flow rate. The flow rate of the saline can be predetermined as a function of the speed of the rotor, the cell diameter, and the chamber constant which has been established empirically. The flow rate will be controlled for example with a device similar to an IV pump. A purpose of the additional saline is to provide a condition inside the rotor chamber where the larger particles will move to one side of the chamber and the smaller particles will move to the other, as illustrated in FIG. 9B. The flow is adjusted so that, in this application, the smaller particles will exit the chamber and move to a waste container, as shown in FIG. 9C. This movement results in the solution in the rotor chamber having a substantially homogenous population of cells, such as stem cells.

After it has been determined that the stem cells have been separated from the rest of the items in the solution (with unwanted proteins and free lipids having been removed from the chamber), the counter flow is stopped. The cells inside the chamber will then form a concentrated pellet on the outside wall of the chamber. The counter flow is reversed and the cell pellet is transferred to the output bag.

An exemplary processing chamber 30 in the form of a centrifuge chamber or cell concentrator, shown in FIGS. 7 and 8, is comprised of a rotating seal 30.1 comprising an outer housing 30.2, one or more seals 30.3, one or more bearings 30.4 and an attachment point 30.6 for attaching the processing chamber to the centrifuge device of the system; one or more fluid paths 30.5 in the form of conduits extending out from the rotating seal and ending in a centrifuge chamber on each end which is in the form of an output chamber 50 housed in a frame 53 wherein the frame is comprised of one or more ports 52 and one or more handles to manually re-position the output chamber 50.

In certain embodiments, the processing chamber 30 in the form of a centrifuge chamber is comprised of one or more fluid paths 30.5 which lead into and out of the various components of the processing chamber, e.g., the output chambers 50. In one embodiment, one fluid path 30.6 radiates outward from the central axis of the processing chamber 30 and terminates near the outer ends of the processing chamber 30, i.e., within the centrifuge chambers which house the output chambers 50. Such a fluid path may be used to, for example, transport the regenerative cell composition from a collection chamber 20 to the processing chamber 30. The fluid path may also be used to re-suspend the cell pellet that is formed after centrifugation. Accordingly, the placement and size of the fluid path must be optimized. The processing chamber may also comprise a fluid path 30.5 which terminates at the bottom central portion of the processing chamber. Such a fluid path may be used to remove supernatant or waste from the output chambers 50. Alternatively, the processing chamber comprises a fluid path which terminates at the bottom central portion of the processing chamber which is used to remove supernatant or waste generated by the processing chamber 30 itself.

In certain embodiments, the processing chamber 30 has two fluid paths. Both fluid paths go through the top of the processing chamber (i.e., the center of the shaft in the rotating seal). One fluid path continues straight down to the bottom of the processing chamber and the other splits into two and extends to the outer ends of the processing chamber, i.e., towards the centrifuge chambers which house the output chambers. In a reconfigured embodiment, the processing chamber 30 has the same general shape but one of the fluid paths is moved or changed. In this embodiment, one fluid path continues straight from the shaft in the rotating seal to the bottom of the processing chamber. The second fluid path, however, splits outside the processing chamber and then connects to the outer ends of the processing chamber. In this embodiment, large output volumes may be generated as the fluid path may be used to add additives and re-suspension solutions to the centrifuge chamber and/or the output chambers directly.

Processing chambers comprising a centrifugation device described above are shown in FIGS. 4, 7-9 and 14-15. With reference to FIGS. 4 and 7-9, between the collection chamber 20 and the processing chamber 30, a pump 34 and one or more valves 14 may be provided. In a preferred embodiment, the valves 14 are electromechanical valves. In addition, sensors, such as pressure sensor 29, may be provided in line with the processing chamber 30 and the collection chamber 36. Utilizing a processing chamber 30 shown in FIGS. 7 and 8, the regenerative cell composition may be pumped from the collection chamber 20 along a pathway through the rotating seal network 30.1 comprising an outer housing 30.2, one or more seals 30.3 (e.g., lip seals), and one or more bearings 30.4.

In a preferred embodiment, the rotating seal network 30.1 which includes a rotating shaft is further comprised of two or more bearings 30.4, three or more lip seals 30.3, and an outer housing 30.2. In this embodiment, the bearings 30.4 further comprise an outer and inner shaft (not shown) referred to herein as races. These races may be separated by precision ground spheres. The races and spheres comprising the bearings are preferably fabricated with material suitable for contact with bodily fluid, or are coated with material suitable for contact with bodily fluid. In a preferred embodiment, the races and spheres are fabricated using, for example, silicone nitride or zirconia. Furthermore, in this embodiment, the three lip seals are comprised of a circular "U" shaped channel (not shown) as well as a circular spring (not shown). The circular "U" shaped channel is preferably fabricated using flexible material such that a leakage proof junction with the rotating shaft of the rotating seal network 30.1 is formed. Additionally, the lip seals are preferably oriented in a manner such that pressure from the regenerative cell composition flowing through the processing chamber causes the seal assembly to tighten its junction with the rotating shaft by way of increased tension. The seals may be secured in position by way of one or more circular clips (not shown) which are capable of expanding and/or collapsing as needed in order to engage a groove in the outer housing 30.2 of the rotating seal network 30.1. Generally, the rotating seal network 30.1 is preferably designed such that multiple fluid pathways, e.g., fluid pathway 30.5, can be maintained in a sterile condition and can be accessed while the centrifuge chamber of the processing chamber is spinning. Accordingly, an advantage of this embodiment is that all areas of the processing chamber illustrated in FIGS. 7 and 8 can be accessed at any given time during the separation and concentration phase of the system. Finally, the heat generated by or near the rotating seal network 30.1 must be controlled to prevent lysis of the cells in the solution which is being moved through the passage. This may be accomplished by, for example, selecting a hard material for constructing the rotating shaft, polishing the area of the rotating shaft which comes in contact with the seals and minimizing contact between the rotating shaft and the seal.

In one embodiment the rotating seal network 30.1 is comprised of a single rubber seal 30.3 and an air gasket (not shown). This seal and gasket provide a tortuous path for any biologic matter which could compromise the sterility of the system. In another embodiment the rotating seal network 30.1 is comprised of multiple spring loaded seals 30.3 which isolate the individual fluid paths. The seals 30.3 are fabricated of a material which can be sterilized as well as seal the rotating shaft without lubricant. In another embodiment the rotating seal network 30.1 is compromised of a pair of ceramic disks (not shown) which create the different fluid paths and can withstand the rotation of the system and not cause cell lysis. In another embodiment the fluid pathway is flexible and is allowed to wind and unwind with respect to the processing chamber. This is accomplished by having the flexible fluid pathway rotate one revolution for every two revolutions of the processing chamber 30. This eliminates the need for a rotating seal altogether.

In one embodiment the processing chamber 30 is designed such that the fluid path enters through the axis of rotation of the rotating seal network 30.1 and then divides into a minimum of two fluid pathways 30.5 each of which lead to opposite extremes of the processing chamber 30 towards the output chambers 50. Accordingly, in a preferred embodiment, the processing chamber 30 is comprised of two or more output chambers 50 as shown in FIGS. 7 and 8. These output chambers 50 are positioned such that they are in one orientation during processing 30.7 and another orientation for retrieval of concentrated regenerative cells 30.8. The two positions of the output chamber 50 may be manually manipulated through a handle 53 which protrudes out of the processing chamber 30. Once the regenerative cell composition is transferred to the processing chamber of FIG. 4, the composition is subjected to a load of, for example, approximately 400 times the force of gravity for a period of approximately 5 minutes. The output chamber 50 is constructed such that the outer extremes of the chamber form a small reservoir for the dense particles and cells. The output chamber 50 retains the dense particles in what is termed a 'cell pellet', while allowing the lighter supernatant to be removed through the second fluid path (not shown). The output chamber is further constructed such that the supernatant may be removed without disturbing the cell pellet. This may be accomplished via fluid pathway which is controlled with valves 14 and a pump 34 that help remove the supernatant. The second fluid path is along the axis of rotation of the rotating seal network 30.1. This fluid path travels from the low point in the center of the processing chamber 30 through the rotating seal to the waste container 40.

The cell pellet comprises the concentrated regenerative cells of the invention. In some embodiments, after the supernatant is removed and directed to the waste chamber 40, additional solutions and/or other additives may be added to the processing chamber 30 from the collection chamber 20 in the manner described above to thereby re-suspend the cell pellet. Re-suspension of the cell pellet in this manner allows for further washing of the regenerative cells to remove unwanted proteins and chemical compounds as well as increasing the flow of oxygen to the cells. The resulting suspension may be subjected to another load of approximately 400 times the force of gravity for another period of approximately 5 minutes. After a second 'cell pellet' is formed, and the resulting supernatant is removed to the waste chamber 40, a final wash in the manner described above may be performed with saline or some other appropriate buffer solution. The final pellet present in the output chamber 50 may then be retrieved using an appropriate syringe after the output chamber 50 is positioned in the orientation appropriate for cell removal. In other embodiments, the final pellet may be automatically moved to a container in the in the output chamber 50 which may be removed and stored or used as needed. This container may be in any appropriate form or size. For example, the container may be a syringe. In all embodiments, the final pellet is removed in an aseptic manner. For example, an output container 50 may be automatically heat sealed and isolated from the other components of the processing chamber for subsequent retrieval and use in proprietary therapeutic applications as described herein.

Figure 4:
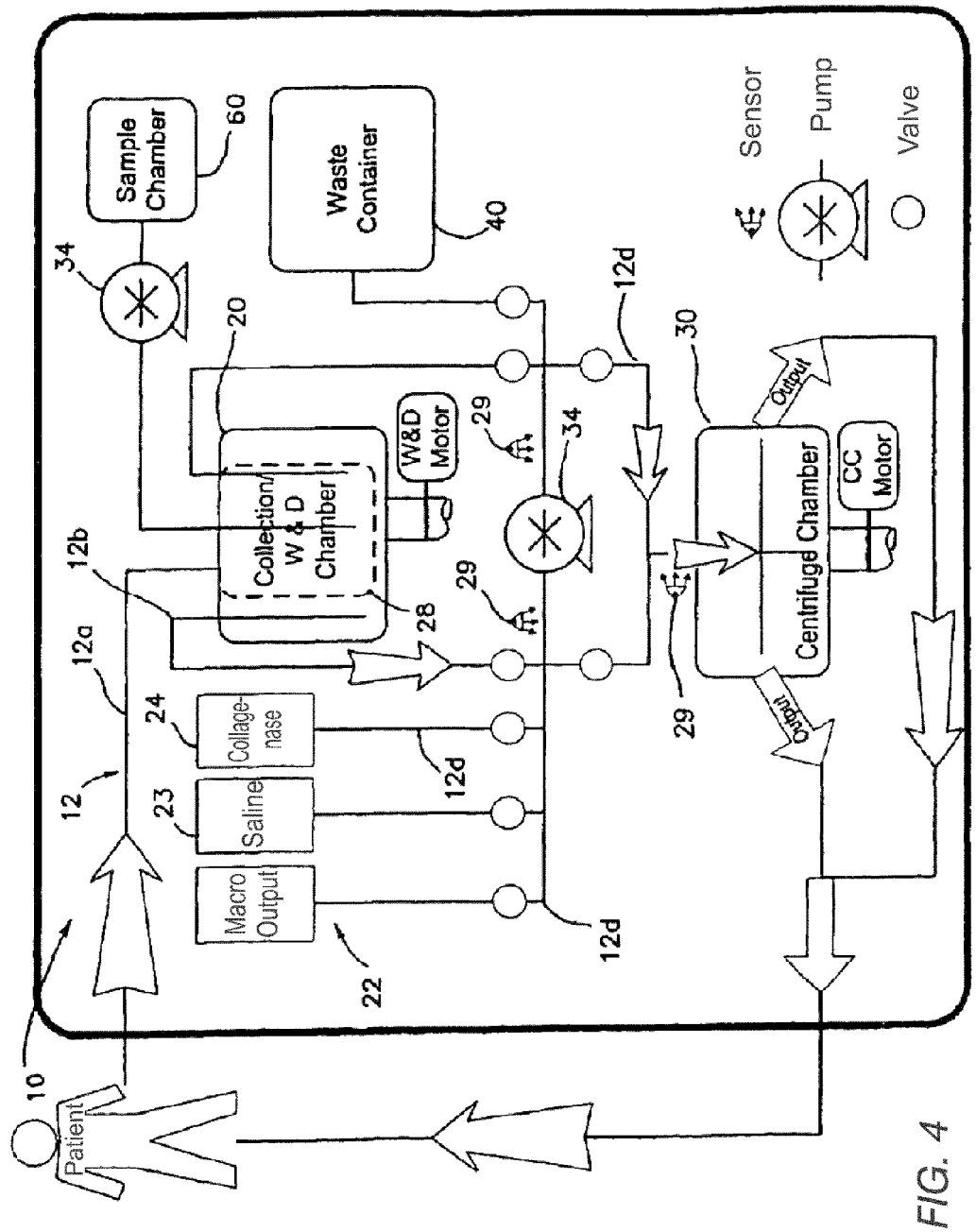
FIG. 4 is an illustration of a system for separating regenerative cells from tissue which includes a centrifuge chamber.

In the illustrated embodiment of FIG. 4, the pressure sensor 29 is in line to determine the pressure of the regenerative cell composition which is generated by the pump 34 as it enters the processing chamber 30. Additional saline or other buffer and washing solution can be added to the regenerative cell composition to assist in the removal of unwanted proteins as the solution is being processed in the processing chamber 30. This repeated washing can be performed multiple times to enhance the purity of the regenerative cell solution. In certain embodiments, the saline can be added at any step as deemed necessary to enhance processing.

In other embodiments, the processing chamber 30 or the output chamber 50 may include one or more ports, e.g., ports 51 or 52. One or more of these ports may be designed to direct the regenerative cells, or a portion thereof, to other targets such as implant materials (e.g., scaffolds or bone fragments), surgical devices, cell culturing devices or purification devices. In these embodiments, the processing chamber 30 or the output chamber 50 may additionally comprise a device to mix the regenerative cells and additives. Mixing may be achieved by any means known to those skilled in the art including but not limited to agitation, rocking, inversion or by compression pulsed or moving rollers. The ports may be also be used to add one or more additives, e.g., growth factors, re-suspension fluids, cell culture reagents, cell expansion reagents, cell preservation reagents or cell modification reagents including agents that transfer genes to the cells. Other examples of additives include agents that optimize washing and disaggregation, additives that enhance the viability of the active cell population during processing, antimicrobial agents (e.g., antibiotics), additives that lyse adipocytes and/or red blood cells, or additives that enrich for cell populations of interest (by differential adherence to solid phase moieties or to otherwise promote the substantial reduction or enrichment of cell populations).

For example, to obtain a homogenous regenerative cell population, any suitable method for separating the particular regenerative cell type may be employed, such as the use of cell-specific antibodies that recognize and bind antigens present on, for example, stem cells or progenitor cells, e.g., endothelial precursor cells. These include both positive selection (selecting the target cells), negative selection (selective removal of unwanted cells), or combinations thereof. Intracellular markers such as enzymes may also be used in selection using molecules which fluoresce when acted upon by specific enzymes. In addition, a solid phase material with adhesive properties selected to allow for differential adherence and/or elution of a particular population of regenerative cells within the final cell pellet could be inserted into the output chamber of the system.

An alternate embodiment of this differential adherence approach would include use of antibodies and/or combinations of antibodies recognizing surface molecules differentially expressed on target regenerative cells and unwanted cells. Selection on the basis of expression of specific cell surface markers (or combinations thereof) is another commonly applied technique in which antibodies are attached (directly or indirectly) to a solid phase support structure (Geiselhart et al., 1996; Formanek et al., 1998; Graepler et al., 1998; Kobari et al., 2001; Mohr et al., 2001).

In another embodiment the cell pellet could be re-suspended, layered over (or under) a fluid material formed into a continuous or discontinuous density gradient and placed in a centrifuge for separation of cell populations on the basis of cell density. In a similar embodiment continuous flow approaches such as apheresis (Smith, 1997), and elutriation (with or without counter-current) (Lasch et al., 2000) (Ito and Shinomiya, 2001) may also be employed.

In all of the foregoing embodiments, at least a portion of the separated adipose derived cells may be cryopreserved, as described in U.S. patent application Ser. No. 10/242,094, entitled PRESERVATION OF NON EMBRYONIC CELLS FROM NON HEMATOPOIETIC TISSUES, filed Sep. 12, 2002, which claims the benefit of U.S. Provisional Patent Application 60/322,070 filed Sep. 14, 2001, which is commonly assigned, and the contents of which in their entireties are expressly incorporated herein by reference.

In a preferred embodiment, the entire system is automated. In another embodiment, the system has both automated and manual components. The system may be comprised of one or more disposable components mounted on a re-usable hardware component or module. The automated systems of the invention provide screen displays (see FIG. 16) that prompt proper operation of the system. The automated systems may also provide a screen that provides status of the procedure and/or the step by step instructions as to the proper setup of the disposable components of the system. The screen may also indicate problems or failures in the system if they occur and provide "troubleshooting" guidance if appropriate. In one embodiment, the screen that allows the user to interface with the system is a touch screen.

The partial and fully automated systems may include a processing device (e.g., microprocessor or personal computer) and associated software programs that provide the control logic for the system to operate and to automate one or more steps of the process based on the user's selection. The processing device may be operably linked to one or more components or steps of the system. By way of example, steps amenable to such automation include, but are not limited to, controlling the ingress and egress of fluids and tissues along particular tubing paths by controlling pumps and valves of the system or processing device; controlling the proper sequence and/or direction of activation; detecting blockages with pressure sensors; mixing mechanisms, measuring the amount of tissue and/or fluid to be moved along a particular pathway using volumetric mechanisms; maintaining temperatures of the various components using heat control devices; washing and concentrating the cell, and integrating the process with timing and software mechanisms. The automated system may also include pressure sensors for detection of blockages and similar safety and quality control mechanisms. In one embodiment, software can control the parameters of the process to allow production of a cell population prepared to specific operator-defined parameters. For example, the processing device can control centrifuge speeds based on the tissue type being processed and/or the cell population or sub-population being harvested. Thus, the automation device or devices improve the performance of the procedures, and provide automatic harvesting of adipose tissue and processing of the adipose tissue for administration to a patient. The processing device may also include standard parallel or serial ports or other means of communicating with other computers or networks. Accordingly, the processing device can be a stand alone unit or be associated with another device.

In certain embodiments, one or more aspects of the system may be user-programmable via software residing in the processing device. The processing device may have one or more pre-programmed software programs in Read Only Memory (ROM). For example, the processing device may have pre-programmed software tailored for processing blood, another program for processing adipose tissue to obtain small volumes of regenerative cells and another program for processing adipose tissue to obtain larger volumes of regenerative cells. The processing device may also have pre-programmed software which provides the user with appropriate parameters to optimize the process based on the user's input of relevant information such as the amount of regenerative cells required, the type of tissue being processed, the type of post-processing manipulation required, the type of therapeutic application, etc. The software may allow for automated collection of "run data" including, for example, the lot numbers of disposable components, temperature and volume measurements, tissue volume and cell number parameters, dose of enzyme applied, incubation time, operator identity, date and time, patient identity, etc.

In a preferred embodiment of the device a bar code reading system would be integrated to permit data entry of these variables (for example disposable set lot number and expiration date, lot number and expiration date of the Collagenase, patient/sample identifiers, etc.) into the processing device as part of documentation of processing. This would reduce the opportunity for data entry errors. Such a bar code reading system could be easily incorporated into the processing device using a USB or other interface port and system known to the art. In this way the device would provide integrated control of the data entry and documentation of the process. A print-out report of these parameters would be part of the user-defined parameters of a programmed operation of the system. Naturally this would require integration of a printer component (hardware and driver) or printer driver in software plus an interface output connector for a printer (e.g., a USB port) in the hardware of the device.

In certain embodiments, the system is a single integrated system that does not require either user intervention to perform the various steps of the separation and concentration process or separate devices. In other embodiments, the system can be run in fully automatic mode without user input. The system can also be run in semi-automatic mode during which the system goes through certain steps without user intervention but requires user intervention before certain processes can occur. In other embodiments, the system is a single integrated system that displays instructions to guide the user to perform predetermined operations at predetermined times. For example, the processing device may prompt users through the steps necessary for proper insertion of tubing, chambers and other components of the system. Accordingly, the user can ensure that the proper sequence of operations is being performed. Such a system can additionally require confirmation of each operational step by the user to prevent inadvertent activation or termination of steps in the process. In a further embodiment, the system may initiate automated testing to confirm correct insertion of tubing, chambers, absence of blockages etc. In yet another embodiment, the system of the present invention is capable of being programmed to perform multiple separation and concentration processes through automated control of tissue flow through the system. This feature may be important, for example, during surgery on a patient where tissue that would otherwise be lost is collected into the system, and regenerative cells from the tissue are separated and concentrated and returned to the patient.

Figure 13:
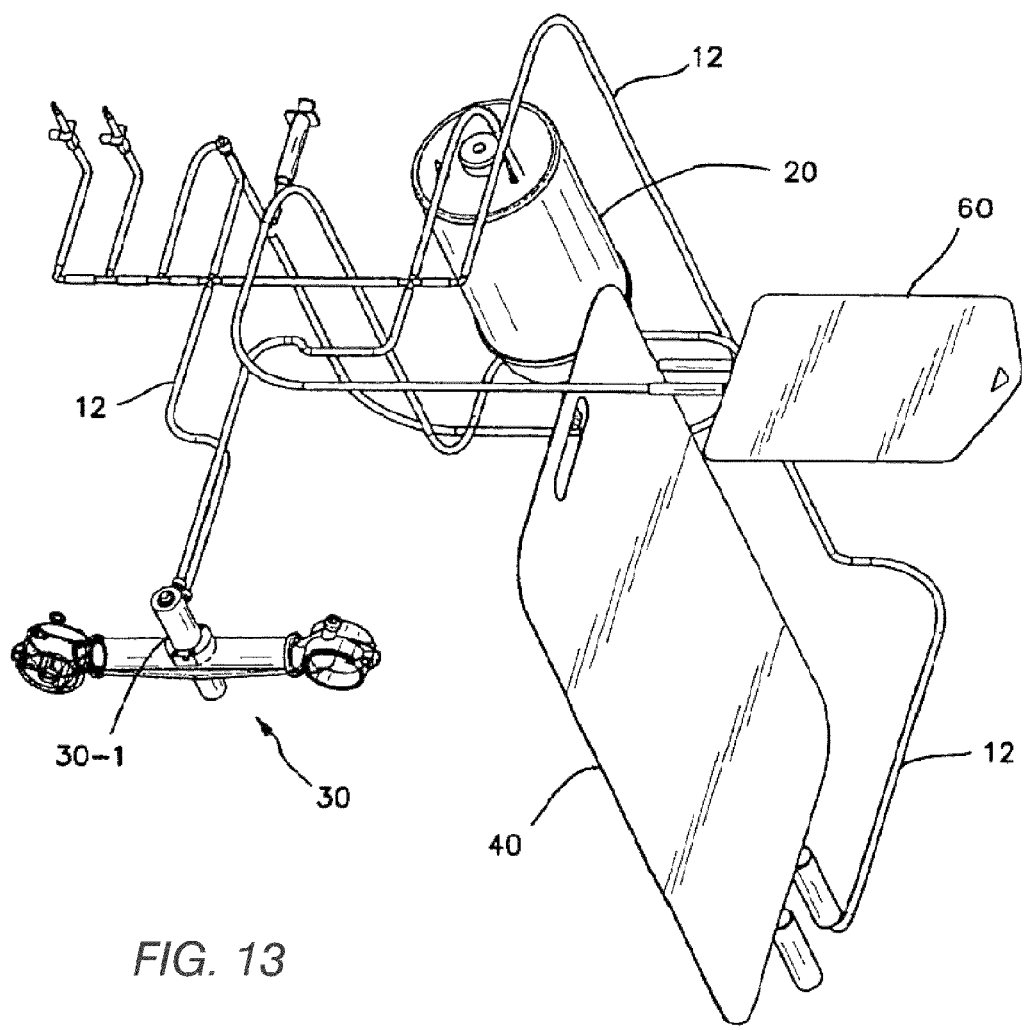
FIG. 13 is an illustration of an exemplary disposable set for a system of the invention.

As set forth above, components of the system may be disposable (referred to herein as "disposable set(s)"), such that portions of the system can be disposed of after a single use. This implementation can help ensure that any surface which comes in contact with the patient's tissue will be disposed of properly after being used. An exemplary disposable set is illustrated in FIG. 13. In a preferred embodiment, the disposable components of the system are pre-sterilized and packaged so as to be usable "off the shelf" that are easy to use and easy to load and that eliminate the need for many tubing connections and complex routing of tubing connections. Such disposable components are relatively inexpensive to manufacture, and therefore, do not create a substantial expense due to their disposal. In one embodiment, the disposable system (referred to interchangeably herein as "disposable set(s)") comprises, consists essentially of, or consists of, the collection chamber 20, the processing chamber 30, the waste chamber 40, the output chamber 50, the filter assemblies 36, the sample bag 60 and the associated conduits 12 or tubing. In preferred embodiments of the disposable sets of the system, the collection chamber 20 and the processing chamber 30 are connected by way of conduits 12 that are housed in a rigid frame. The rotating seal network (FIGS. 7 & 8) of a processing chamber 30 may also be housed in the same rigid frame. In another preferred embodiment, the various chambers and containers of the disposable set are comprised of the necessary interfaces that are capable of communicating with the processing device of the system such that the pumps, valves, sensors and other devices that automate the system are appropriately activated or de-activated as needed without user intervention. The interfaces also reduce the time and expertise required to set up the system and also reduce errors by indicating how to properly set up the system and alerting the user in the event of an erroneous setup.

The disposable sets may further comprise one or more needles or syringes suitable for obtaining adipose or other tissue from the patient and returning regenerative cells to the patient. The type number and variety of the needles and syringes included will depend on the type and amount of tissue being processed. The disposable sets may further comprise one or more rigid or flexible containers to hold washing fluids and other processing reagents used in the system. For example, the disposable sets may comprise containers to hold saline, enzymes and any other treatment or replacement fluids required for the procedure. In addition, suitable washing solutions, re-suspension fluids, additives, agents or transplant materials may be provided with the disposable sets for use in conjunction with the systems and methods of the invention.

Figures 2, 14:
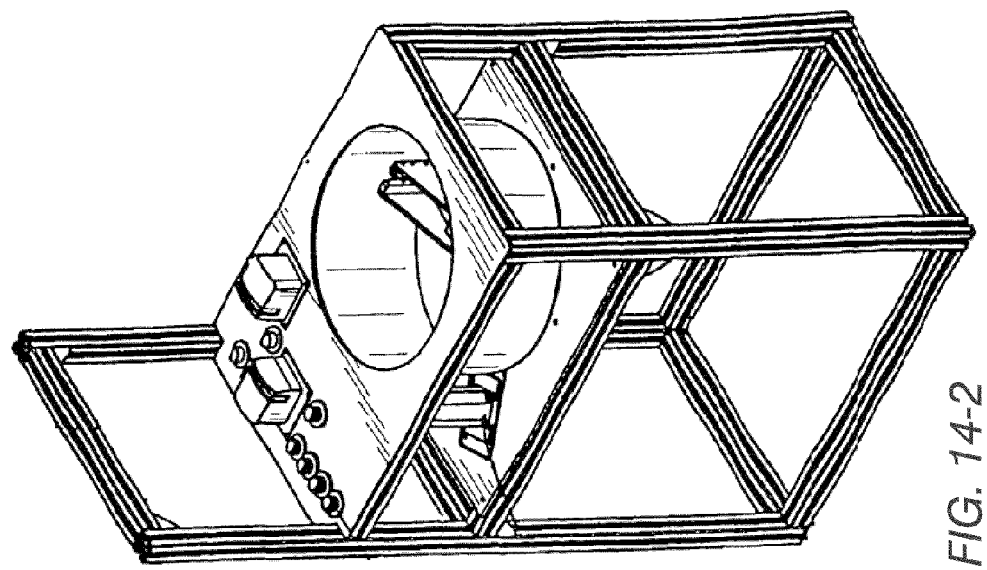
Figures 1, 14:
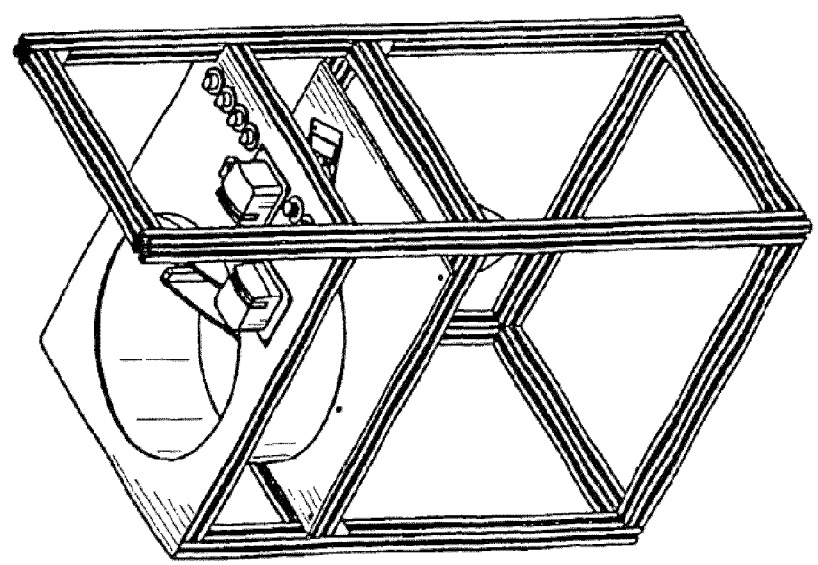

The re-usable component of the system comprises, consists essentially of, or consists of the agitation mechanism for the collection chamber, the pump, and assorted sensors which activate valves and pump controls, the centrifuge motor, the rotating frame of the centrifuge motor, the user interface screen and USB ports and other associated devices. An exemplary re-usable component is illustrated in FIG. 14. The re-usable hardware may be used with a variety of disposable sets. For example, the re-usable hardware can be used with disposable sets for separating and concentrating regenerative cells from a wide variety of tissues as described herein.

In one embodiment, a disposable set for use in the system is comprised of a collection chamber 20 which can accommodate about 800 mL of tissue; a processing chamber 30 which can process the regenerative cell composition generated by about 800 mL of tissue washed and digested in the collection chamber 20; an output chamber 50 which can accommodate at least 0.5 mL of regenerative cells; and a waster container 40 which can accommodate about 10 L of waste. In this embodiment, the hardware device is no larger than 24"L×18"W×36"H. Alternative dimensions of the various components of the disposable sets as well as the hardware device may be constructed as needed and are intended to be encompassed by the present invention without limitation.

Figures 2, 15A:
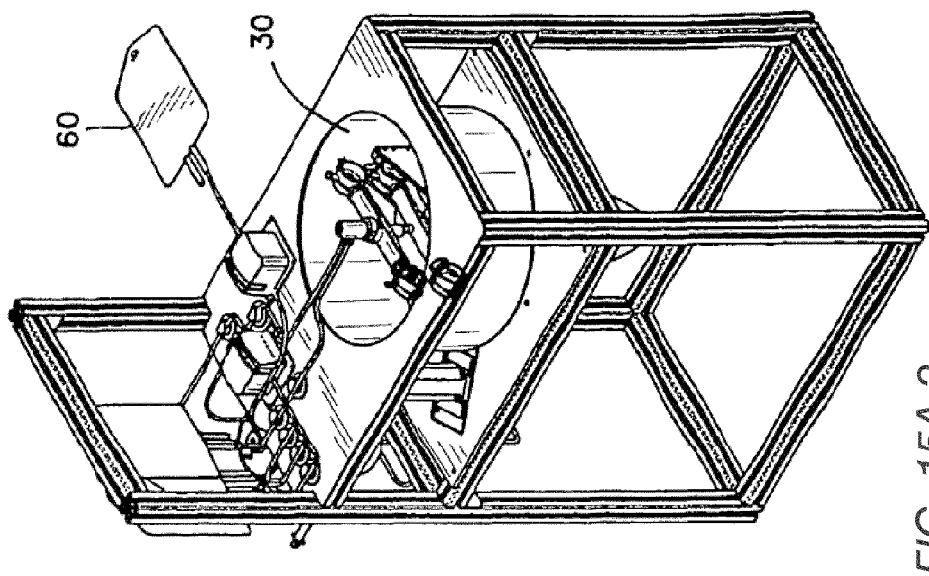
Figures 1, 15A:
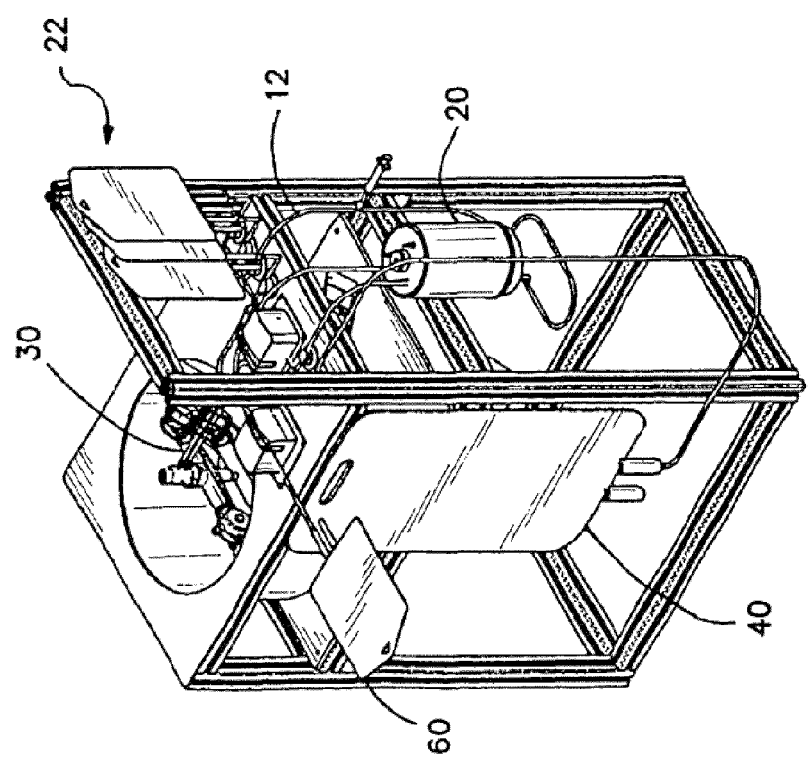

The disposable components of the system are easy to place on the device. An illustration of a disposable set utilized assembled together with a corresponding re-usable component is illustrated in FIG. 15. The system is preferably designed such that it can detect an improperly loaded disposable component. For example, the components of each disposable set may have color-guided marks to properly align and insert the tubing, chambers etc. into appropriate places in the system. In additional embodiments, the system disclosed herein is a portable unit. For example, the portable unit may be able to be moved from one location where adipose tissue harvesting has occurred, to another location for adipose tissue harvesting. In certain implementations, the portable unit is suitable for harvesting and processing of adipose tissue by a patient's bedside. Thus, a portable unit may be part of a system which can be moved from patient to patient. Accordingly, the portable unit may be on wheels which lock in place and, thus, can be easily placed and used in a convenient location in a stable and secure position throughout the procedure. In other embodiments, the portable unit is designed for set-up and operation on a flat surface such as a table top. The portable unit may also be enclosed in a housing unit. The portable unit may further be comprised of hangers, hooks, labels, scales and other devices to assist in the procedure. All of the herein described re-usable components of the system such as the centrifuge, processing device, display screen may be mounted on the portable unit of the system.

Alternate manual embodiments for obtaining regenerative cells are also within the scope of this invention. For example, in one embodiment, adipose tissue may be processed using any combination of the components of the system, equipment and/or supplies described herein.

The regenerative cells obtained by the foregoing methods may be mixed with adipose tissue fragments and administered to a patient without further processing, or may be administered to a patient after being mixed with other tissues, cells, implants or devices. In certain embodiments, the regenerative cells are mixed with one or more units of adipose tissue that has not been similarly processed. Thus, by practicing the methods of the invention, a composition comprising adipose tissue with an enhanced concentration of regenerative cells may be administered to the patient. The volumes of the various units of adipose tissue may be different. For example, one volume may be at least 25% greater than the volume of another unit of adipose tissue. Furthermore, one volume may be at least 50%, such as at least 100%, and even 150% or more greater than the volume of another unit of adipose tissue. In addition, the desired composition may be obtained by mixing a first unit of adipose tissue with the concentrated regenerative cell population, which may be a cell pellet containing the regenerative cells, with one or more other units of adipose tissue. In certain embodiments, these other units will not have an increased concentration of regenerative cells, or in other words, will have a regenerative cell concentration less than that contained in the first unit of adipose tissue. In other embodiments, one of the units is cryopreserved material that contains, for example, an increased concentration of regenerative cells.

At the end of processing, the concentrated cells may be loaded into a delivery device, such as a syringe, for placement into the recipient by either subcutaneous, intramuscular, or other technique allowing delivery of the cell/tissue admixture to the target site within the patient, for example, the periurethral region, the subcutaneous space beneath a wrinkle, or within the breast. In other words, cells may be placed into the patient by any means known to persons of ordinary skill in the art. Preferred embodiments include placement by needle or catheter, or by direct surgical implantation. In the embodiment of surgical implantation the cell and tissue admixture could be applied in association with additives such as a pre-formed matrix.

The active cell population may be applied alone or in combination with other cells, tissue, tissue fragments, growth factors such as VEGF and other known angiogenic or arteriogenic growth factors, biologically active or inert compounds, resorbable plastic scaffolds, or other additive intended to enhance the delivery, efficacy, tolerability, or function of the population. The cell population may also be modified by insertion of DNA or by placement in cell culture in such a way as to change, enhance, or supplement the function of the cells for derivation of a structural or therapeutic purpose. For example, gene transfer techniques for stem cells are known by persons of ordinary skill in the art, as disclosed in (Morizono et al., 2003; Mosca et al., 2000), and may include viral transfection techniques, and more specifically, adeno-associated virus gene transfer techniques, as disclosed in (Walther and Stein, 2000) and (Athanasopoulos et al., 2000). Non-viral based techniques may also be performed as disclosed in (Muramatsu et al., 1998).

In another aspect, the cells could be combined with a gene encoding growth factors, e.g., angiogenic growth factor(s) which would allow cells to act as their own source of the growth factor. Addition of the gene (or combination of genes) could be by any technology known in the art including but not limited to adenoviral transduction, "gene guns," liposome-mediated transduction, and retrovirus or lentivirus-mediated transduction, plasmid, adeno-associated virus. Cells could be implanted along with a carrier material bearing gene delivery vehicle capable of releasing and/or presenting genes to the cells over time such that transduction can continue or be initiated in situ.

When the cells and/or tissue containing the cells are administered to a patient other than the patient from whom the cells and/or tissue were obtained, one or more immunosuppressive agents may be administered to the patient receiving the cells and/or tissue to reduce, and preferably prevent, rejection of the transplant. As used herein, the term "immunosuppressive drug or agent" is intended to include pharmaceutical agents which inhibit or interfere with normal immune function. Examples of immunosuppressive agents suitable with the methods disclosed herein include agents that inhibit T-cell/B-cell costimulation pathways, such as agents that interfere with the coupling of T-cells and B-cells via the CTLA4 and B7 pathways, as disclosed in U.S. Pat. Pub. No. 20020182211. A preferred immunosuppressive agent is cyclosporine A. Other examples include myophenylate mofetil, rapamicin, and anti-thymocyte globulin. In one embodiment, the immunosuppressive drug is administered with at least one other therapeutic agent. The immunosuppressive drug is administered in a formulation which is compatible with the route of administration and is administered to a subject at a dosage sufficient to achieve the desired therapeutic effect. In another embodiment, the immunosuppressive drug is administered transiently for a sufficient time to induce tolerance to the regenerative cells of the invention.

In certain embodiments of the invention, the cells are administered to a patient with one or more cellular differentiation agents, such as cytokines and growth factors. Examples of various cell differentiation agents are disclosed in (Gimble et al., 1995; Lennon et al., 1995; Majumdar et al., 1998; Caplan and Goldberg, 1999; Ohgushi and Caplan, 1999; Pittenger et al., 1999; Caplan and Bruder, 2001; Fukuda, 2001; Worster et al., 2001; Zuk et al., 2001).

In another aspect, the cell population could be placed into the recipient and surrounded by a resorbable plastic sheath or other materials such as that manufactured by MacroPore Biosurgery, Inc. (e.g., U.S. Pat. Nos. 6,269,716; 5,919,234; 6,673,362; 6,635,064; 6,653,146; 6,391,059; 6,343,531; 6,280,473). In this setting the sheath would prevent prolapse of muscle and other soft tissue into the area of a defect processed adipose tissue-derived cells to promote controlled repair of the defect. This approach could be used in reconstructive surgery in which the sheath could be pre-molded to the final form desired allowing the tissue to be molded in vivo to the desired shape. In this aspect, the beneficial effect might be enhanced by supplementation with additional components such as pro-adipogenic or angiogenic protein growth factors or biological or artificial scaffolds.

As described herein, numerous defects and disorders may be treated with the regenerative cells obtained using the systems and methods of the invention. For example, in breast augmentation mammoplasty, soft tissue defect correction, and/or treatments of urinary incontinence, adipose tissue enhanced with regenerative cells may improve neovascularization and diminish necrosis in the implant, thereby resulting in improved engraftment and a reduction in the risk of liponecrotic pseudocyst formation. The regenerative cell-enhanced adipose tissue may be used to correct soft tissue defects and the like, as described above. The addition of this concentrated regenerative cell population to the normal adipose tissue graft may improve the longevity of the graft through providing a supportive microenvironment. In addition, the compositions described herein may also be used to provide structural support of the lower esophageal sphincter as well as the external anal sphincter to treat gastroesophageal reflux disease (GERD) and fecal incontinence (Bernardi, Favetta et al. 1998), respectively.

Typically, a person who is deemed a candidate for conventional augmentation mammoplasty is a candidate for breast augmentation by adipose tissue-derived cell augmented autologous fat transfer. In addition to those candidates deemed eligible for conventional augmentation mammoplasty, these methods may apply to the population of persons seeking a small/moderate enlargement, shape change or contour alteration of a breast or breasts, which may not be technically possible or aesthetically acceptable with existing implant technology. Candidates for soft tissue augmentation are similarly candidates for autologous fat transfer procedures using cell enhanced autologous adipose tissue. Examples of soft tissue augmentation procedures include, but are not limited to: contour deformities of the face including but not limited to facial (e.g., glabellar, nasolabial) folds, perioral lines, marionette lines, dermal divots; buttocks; calves; genitals; retro-orbital, and plantar fat pad. A person who is deemed a candidate for urethral bulking injection is also a candidate for autologous fat transplantation with the cell-enhanced adipose tissue disclosed herein. These procedures may include transurethral as well as periurethral injection in females, as well as transurethral or antegrade injection in males. Pre-operative evaluation typically includes routine history and physical examination in addition to thorough informed consent disclosing all relevant risks and benefits of the procedure.

After identification of a patient candidate, the patient typically undergoes adipose tissue collection. The patient's habitus may be examined for a site suitable for adipose tissue collection. The procedure may be performed at bedside or in an operating suite with hemodynamic monitoring appropriate to the patient's clinical status. Some preferred harvest site(s) will be characterized by: potential space(s) limited by normal anatomical structures, no major vascular or visceral structures at risk for damage, and ease of access. While virgin harvest sites are typically preferred, a previous harvest site does not preclude additional adipose tissue harvest. These preferred sites include but are not limited to the following: lateral and medial thigh regions of bilateral lower extremities, anterior abdominal wall pannus, and bilateral flank regions. These procedures may frequently be performed concomitantly with liposculpture. The site of adipose tissue collection may also be determined by the patient's aesthetic expectations as well as the safety profile as determined by the physician.

The area to be harvested is injected subcutaneously, for example, with a standard tumescent fluid solution, which may or may not contain a combination of lidocaine, saline, and/or epinephrine in different standardized dosing regimens. Using an 11-blade scalpel (or other standard blade), a small puncture wound is made in order to transverse the dermis near the harvest area. The blade is rotated, such as being turned 360 degrees, to complete the wound. A blunt tip 14-guage (or appropriately sized) cannula may then be inserted into the subcutaneous adipose tissue plane. The cannula may be connected to a power assisted suction device or to a syringe for manual aspiration. The cannula is then moved throughout the plane to disrupt the connective tissue architecture. The volume of aspirate obtained may range from about 0 cc to about 1500 cc. A fraction or portion of adipose tissue collected in this manner will be processed for isolation and concentration of regenerative cells using the methods described herein. The remainder of the adipose tissue may be processed for re-implantation into the patient according to the currently accepted standard of care. Alternatively, the patient may have adipose removed through a lipectomy procedure. After removal of adipose tissue, hemostasis will be achieved with standard surgical techniques and the wound closed primarily.

The collection of adipose tissue may take place 1-2 hours prior to the transplantation procedures. However, the timing of collection may vary and may depend on quality care standards. Ultimately, the practitioner responsible for administering care to the patient will determine the timing of collection. In another embodiment, adipose tissue-derived cells, which have been cryopreserved in an adipose tissue-derived cell banking facility, may be used.

The volume of adipose tissue collected will typically vary from about 1 cc to about 1500 cc. Preferred methods of tissue collection will be to follow accepted quality care standards. The volume of fat removed will vary from patient to patient and may depend on a number of factors including, but not limited to: amount of adipose tissue required for augmentation mammoplasty, aesthetic expectations, age, body habitus, coagulation profile, hemodynamic stability, co-morbidities, and physician preference.

After tissue processing is complete, the patient may be prepared to undergo adipose tissue transplantation in connection with augmentation mammoplasty, soft tissue augmentation, and/or treatment of urinary incontinence. Some issues surrounding transplantation include timing, cell dose, route, method, location, and monitoring.

In certain embodiments of the invention, the regenerative cell-enhanced adipose tissue is administered to the patient at the time of the transplantation procedures. These methods do not exclude the need for multiple injections of material over time. Ultimately, the timing used will follow quality care standards. In additional embodiments, an alternative timing regimen may exist if the cells to be applied are subject to modification, purification, stimulation, or other manipulation, as discussed above.

The cell dose to be delivered to an individual patient will typically be determined from the cell yield after adipose tissue processing. All of the cells harvested may not be required for the particular procedures, and remaining portions of cells may be cryopreserved as described herein. In one embodiment, the minimum number of cells to be delivered to the patient is expected to be $5.5 \times 10^5$ per 50 cc of transplanted fat. However, this value can be expected to change by orders of magnitude to achieve the desired effect. The injection of additional augmented adipose tissue (over-correction) is not an uncommon practice, as a percentage of the volume injected is expected to regress with time. In addition, because the methods disclosed herein do not exclude the need for a series of doses, more cells may be administered to the patient than indicated above.

In breast augmentation procedures, the route of delivery may include open delivery through a standard 14-guage blunt tip cannula inserted into the breast tissue through a axillary, periareolar, inframammary In soft tissue augmentation procedures, the route of delivery may include open delivery through a standard 14-guage blunt tip cannula inserted into the soft tissue through an appropriately placed incision. In urinary incontinence procedures, the route of delivery may include direct injection at the bladder neck and proximal urethra through cystoscopic visualization. Alternatively or in addition, the transplant may be delivered via an antegrade route. Alternatively or in addition, the cell-enhanced tissue may be delivered through an intravenous route to be accessed via currently accepted methods. In the intravenous method, controlling the directional flow of transplanted material may be achieved through endocrine and paracrine trafficking resulting from the inflammatory process initiated by surgical intervention. The routes discussed herein do not exclude the use of multiple routes to achieve the desired clinical effect., or umbilical incision. Alternatively or in addition, cell-enhanced tissue may be delivered through a transaxillary endoscopic subpectoral approach.

In one embodiment, regenerative cells obtained from adipose processing are mixed with fat to be transplanted in the ratio described above. This mixing may occur through automated means (e.g., device-controlled agitation or centrifugation) or through manual methods (e.g., luer-locked syringes, vortexing). The regenerative cell enhanced adipose tissue is preferably administered in a tear like fashion to maximize the surface area to volume ratio. In another embodiment, regenerative cells may be resuspended in an artificial or natural medium or tissue scaffold, which is then inserted into the implant region, such as the breast region, and/or the intrinsic sphincter region to bring about the desired effect. In a preferred embodiment the combined cells and tissue are injected following the process generally referred to as the 'Coleman Technique' (Coleman 1991; Coleman 1995; Coleman 2001).

Adipose tissue collection may take place in any appropriate clinical setting, such as the following locations: clinic, clinical office, emergency department, hospital ward, intensive care unit, operating room, catheterization suite, and radiologic suite. Augmentation mammoplasty is typically performed in an outpatient setting, but may be performed in the in-patient environment. Urethral bulking injection is typically performed in an outpatient setting, but may be performed in the in-patient environment.

In breast augmentation procedures, the effect of regenerative cell augmented autologous fat transfer may be manifested by one or more of the following clinical measures: increased breast size, altered breast shape, altered breast contour, sustained engraftment, decreased rate of liponecrotic cyst formation, improved patient satisfaction and decreased use of implantable foreign material. In other soft tissue augmentation procedures, the effect of regenerative cell augmented autologous fat transfer may be manifested by one or more of the following clinical measures: improved soft tissue shape, improved tissue function, improved soft tissue contour, sustained engraftment, improved patient quality of life and decreased use of implantable foreign material. In urinary incontinence procedures, the effect of regenerative cell augmented autologous fat transfer for sphincter support may be manifested by one or more of the following clinical measures: decreased frequency of incontinence, sustained engraftment, improved patient quality of life and decreased use of implantable foreign material. The effect of cellular therapy typically takes place over the course of days to weeks. However, a beneficial effect may be observed as early as several hours and may persist for years.

Patient monitoring prior to, during, and after the delivery of transplanted adipose tissue may include, but is not limited to, the following: coagulation studies, oxygen saturation, hemodynamic monitoring, and wound status. Patients may be advised that they should receive pre-operative diagnostic procedures, such as mammographies, as there may be concerns that calcifications that form may distort the ability to detect malignant calcification of the breast. However, the advice may be optional because the use of magnetic resonance imaging may overcome this limitation. Additional monitoring will be specific to the desired clinical effect. Patient monitoring prior to, during, and after the delivery of transplanted adipose tissue may include the following: urinalysis, pelvic examination, cystoscopy, and urodynamic evaluation, coagulation studies, oxygen saturation, hemodynamic monitoring, and wound status. Additional monitoring will be specific to the desired clinical effect.

The following examples are provided to demonstrate particular situations and settings in which this technology may be applied and are not intended to restrict the scope of the invention and the claims included in this disclosure.

EXAMPLES

Example 1

Expression of Angiogenic Growth Factor, VEGF, by ADC

Vascular Endothelial Growth Factor (VEGF) is one of the key regulators of angiogenesis (Nagy et al., 2003; Folkman, 1995). Placenta Growth Factor, another member of the VEGF family, plays a similar role in both angiogenesis as well as arteriogenesis. Specifically, transplant of wild-type (PlGF+/+) cells into a PlGF knockout mouse restores ability to induce rapid recovery from hind limb ischemia (Scholz et al., 2003).

Figure 16A:
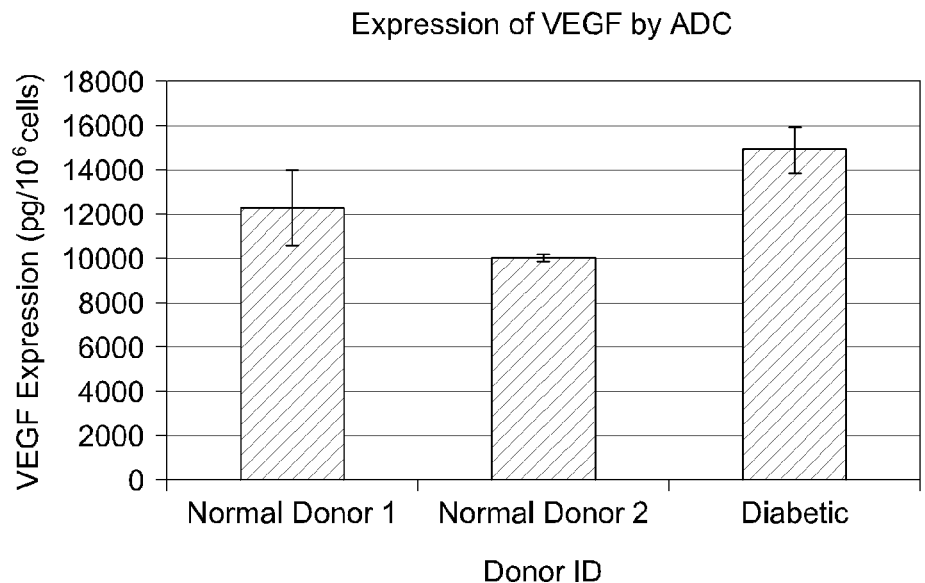
FIGS. 16A and 16B depict the expression of VEGF (5A) and PIGF (5B) protein by cultured adipose derived stem cells.
Figure 16B:
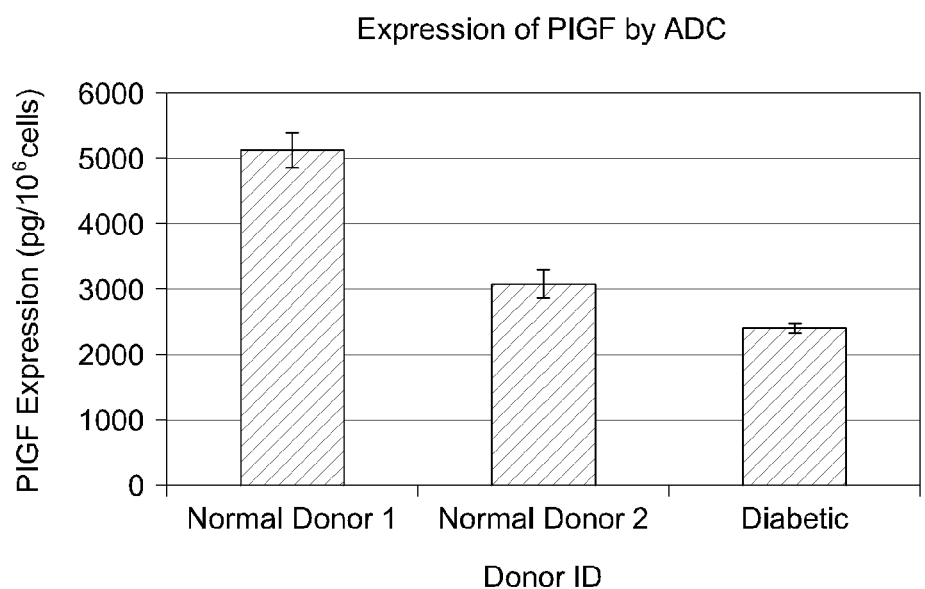

Given the importance of angiogenesis and arteriogenesis to the revascularization process, PlGF and VEGF expression by the regenerative cells of the present invention was examined using an ELISA assay (R&D Systems, Minneapolis, Minn.) using adipose derived regenerative cells from three donors. One donor had a history of hyperglycemia and Type 2 diabetes (a condition highly associated with microvascular and macrovascular disease). Regenerative cells from each donor were plated at 1,000 cells/cm$^2$ in DMEM/F-12 medium supplemented with 10% FCS and 5% HS and grown until confluent. Supernatant samples were taken and assayed for expression of PlGF and VEGF protein. As shown in FIGS. 16A and 16B, the results demonstrate robust expression of both VEGF (FIG. 16A) and PlGF (FIG. 16B) by the adipose derived regenerative cells of the invention.

In a separate study, the relative quantity of angiogenic related cytokines secreted by cultured regenerative cells from normal adult mice was measured. The regenerative cells were cultured in alpha-MEM with 10% FBS to five days beyond cell confluence, at which time the cell culture medium was harvested and evaluated by antibody array analysis (RayBio® Mouse Cytokine Antibody Array II (RayBiotech, Inc.). The following angiogenic related growth factors were detected: Vascular Endothelial Growth Factor (VEGF), bFGF, IGF-II, Eotaxin, G-CSF, GM-CSF, IL-12 p40/p70, EL-12 p70, IL-13, IL-6, IL-9, Leptin, MCP-1, M-CSF, MIG, PF-4, TIMP-1, TIMP-2, TNF-α, and Thrombopoetin.

These data demonstrate that the regenerative cells of the present invention express a wide array of angiogenic and arteriogenic growth factors. Moreover, the finding that a diabetic patient expressed VEGF and PlGF at equivalent levels to those of normal patients suggest that diabetic patients may be candidates for angiogenic therapy by autologous adipose derived regenerative cells.

Example 2

ADC Contains Cell Populations that Participate in Angiogenesis

Endothelial cells and their precursors, endothelial progenitor cells (EPCs), are known to participate in angiogenesis. To determine whether EPCs are present in adipose derived regenerative cells, human adipose derived regenerative cells were evaluated for EPC cell surface markers, e.g., CD-34.

ADCs were isolated by enzymatic digestion of human subcutaneous adipose tissue. ADCs (100 ul) were incubated in phosphate saline buffer (PBS) containing 0.2% fetal bovine serum (FBS), and incubated for 20 to 30 minutes at 4.degree. C. with fluorescently labeled antibodies directed towards the human endothelial markers CD-31 (differentiated endothelial cell marker) and CD-34 (EPC marker), as well as human ABCG2 (ATP binding cassette transporter), which is selectively expressed on multipotent cells. After washing, cells were analyzed on a FACSAria Sorter (Beckton Dickenson—Immunocytometry). Data acquisition and analyses were then performed by FACSDiva software (BD-Immunocytometry, Calif). The results (not shown) showed that the adipose derived regenerative cells from a healthy adult expressed the EPC marker CD-34 and ABCG2, but not the endothelial cell marker CD-31. Cells expressing the EPC marker CD-34 were detected at similar frequency in regenerative cells derived from a donor with a history of diabetes.

Figure 17:
FIG. 17 depicts detection of endothelial progenitor cells within adipose derived stem cell populations.

To determine the frequency of EPCs in human adipose derived regenerative cells after their culture in endothelial cell differentiation medium, ADCs were plated onto fibronectin-coated plates and cultured in endothelial cell medium for three days to remove mature endothelial cells. Nonadherent cells were removed and re-plated. After 14 days, colonies were identified by staining with FITC-conjugated Ulex europaeus Agglutinin-1 (Vector Labs, Burlingame, Calif.) and DiI-labeled acetylated LDL (Molecular Probes, Eugene, Oreg.). As shown in FIG. 17, the results indicate an EPC frequency of approximately 500 EPC/$10^6$ ADC cells.

The presence of EPCs within the adipose tissue derived regenerative cells indicates that these cells can participate directly in development of new blood vessels and enhance angiogenesis and reperfusion.

Example 3

In Vitro Development of Vascular Structures in ADC

Figure 18A:
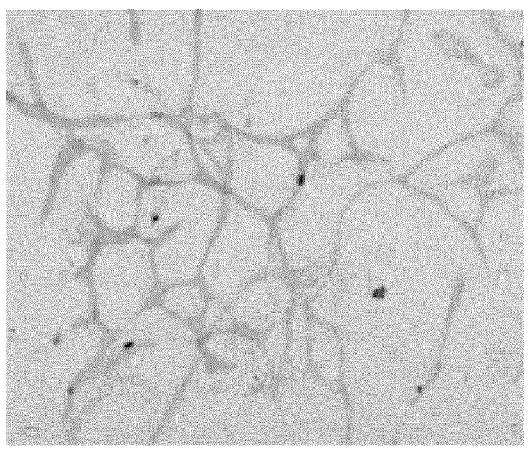
FIGS. 18A and 18B depict the in vitro development of vascular structures in both normal (7A) and streptozotocin-treated (7B) mice.
Figure 18B:
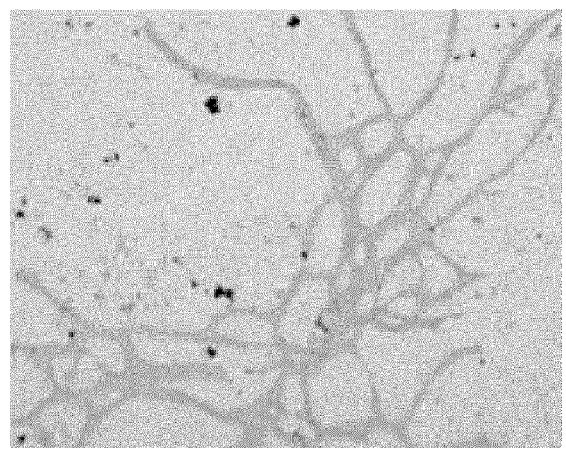

An art-recognized assay for angiogenesis is one in which endothelial cells grown on a feeder layer of fibroblasts develop a complex network of CD31-positive tubes reminiscent of a nascent capillary network (Donovan et al., 2001). Since adipose derived regenerative cells contain endothelial cells, EPCs and other stromal cell precursors, we tested the ability of these regenerative cells to form capillary-like structures in the absence of a feeder layer. Regenerative cells obtained from inguinal fat pads of normal mice developed capillary networks two weeks after culture (FIG. 18A). Notably, regenerative cells from hyperglycemic mice with streptozotocin (STZ)-induced Type 1 diabetes eight weeks following administration of STZ formed equivalent capillary networks as those formed by cells from normal mice (FIG. 18B).

In a subsequent study, adipose derived regenerative cells were cultured in complete culture medium (a-MEM supplemented with 10% FCS) and no additional growth factors. These regenerative cells also formed capillary networks. Furthermore, the vascular structures formed stained positive for the endothelial cell markers CD31, CD34, VE-cadherin and von Willebrand factor/Factor VIII, but not the pan-lymphocyte marker, CD45.

To compare the ability of regenerative cells from young vs. elderly mice to form capillary networks, regenerative cells from normal young and elderly mice (aged 1, 12, or 18 months) were cultured for 2 weeks in complete culture medium ($\alpha$-MEM supplemented with 10% FCS) and no additional growth factors. Equivalent capillary-like networks were observed in cultures of regenerative cells from all donors (not shown).

The foregoing data demonstrates that adipose derived regenerative cells from normal and diabetic, as well as young and elderly patients can form vascular structures consistent with the formation of nascent capillary networks. Accordingly, the regenerative cells of the invention may be used to treat angiogenic insufficiencies.

Example 4

In Vivo Development of Vascular Structures in ADC

In vitro angiogenic potential, while promising, is of little value if the cells do not exert in vivo angiogenic activity. Surgically inducing hind limb ischemia is an in vivo model capable of identifying the angiogenic potential of a given therapy. This model was developed in immunodeficient (NOD-SCID) mice in which the ability of human cells to drive reperfusion could be observed.

Pre-operative blood flow values were determined for both hind limbs as described below. The vasculature of anesthetized mice was tied off with a 4-0 silk ligature at the following sites: 1) iliac artery proximal to its bifurcation, 2) just distal to the origin of deep femoral artery, 3) just proximal to branching of the superficial femoral artery. After ligation, the vasculature was removed en bloc. Prior to wound closure, grossly observable collaterals branching from the ligated femoral arteries were also ligated. Twenty four hours later, 129S mice were injected with 5×$10^6$ syngeneic mouse adipose derived regenerative cells and NOD SCID mice were injected with human adipose derived regenerative cells through the tail vein. Flow was imaged immediately after surgery and at intervals following treatment using a Laser Doppler Flow Imager (Moor Instruments Inc., Wilmington, Del.). Measurements, taken three times per week for 24 days, were normalized to the pre-operative value for that limb and presented relative to the control (unoperated) limb.

The model of hind limb ischemia is extremely sensitive to the strain of mouse used. NOD SCID mice are immunodeficient animals, lacking the ability to ignite an acute inflammatory response. For these mice, this surgical approach generates severe ischemia such that two thirds of untreated animals lost hind limb structures below the site of femoral excision. No cell-treated animal lost any structures above the toe. Yet, for immunocompetent 129S mice, no untreated animals lost any structures above the phalanges and displayed an endogenous ability to partially regenerate reperfusion. This could be due to the intrinsic angiogenesis associated with an acute inflammatory response. This may explain why reperfusion was less extreme when comparing the treated versus control animals of different strains.

However, the results showed that mice treated with adipose derived regenerative cells showed significantly improved perfusion as compared to untreated mice of both strains. By Day 12, blood flow was restored to 50±11% in NOD-SCID mice treated with human regenerative cells, as compared to 10±10% in untreated mice (p<0.05). Similarly, immunocompetent 129S mice exhibited 80±12% restoration of flow at day 14, as compared to 56±4% in untreated mice In addition, gross dissection of mice revealed the appearance of collateral vessels in the hind limbs of mice treated with regenerative cells, but not in those from untreated mice or in the healthy limbs of any mice.

Example 5

Increasing ADC Dose is Associated with Improved Graft Survival and Angiogenesis

Transplant of autologous adipose tissue is a relatively common procedure in plastic and reconstructive surgery {Fulton, 1998; Shiffman, 2001}. However, this procedure is limited by the fact that the adipose tissue fragments are transferred without a vascular supply and, as a result, graft survival is dependent upon neovascularization (Coleman, 1995; Eppley et al., 1990). Thus, in a limited way, the transplanted tissue represents an ischemic tissue.

A study in Fisher rats was performed in which adipose tissue fragments were transplanted into the subcutaneous space over the muscles of the outer thigh. The right leg was transplanted with 0.2 g of adipose tissue fragments alone, the left leg with 0.2 g of adipose tissue fragments supplemented by addition of adipose derived stem cells at three different doses ($1.7 \times 10^{5-1.3} \times 10^6$ cells/graft; three animals per dose); in this way the contralateral leg acted as a control. Animals were then maintained for one month after which the animals were euthanized and the grafts recovered, weighed, fixed in formalin and embedded in paraffin for histologic analysis.

Figure 20A:
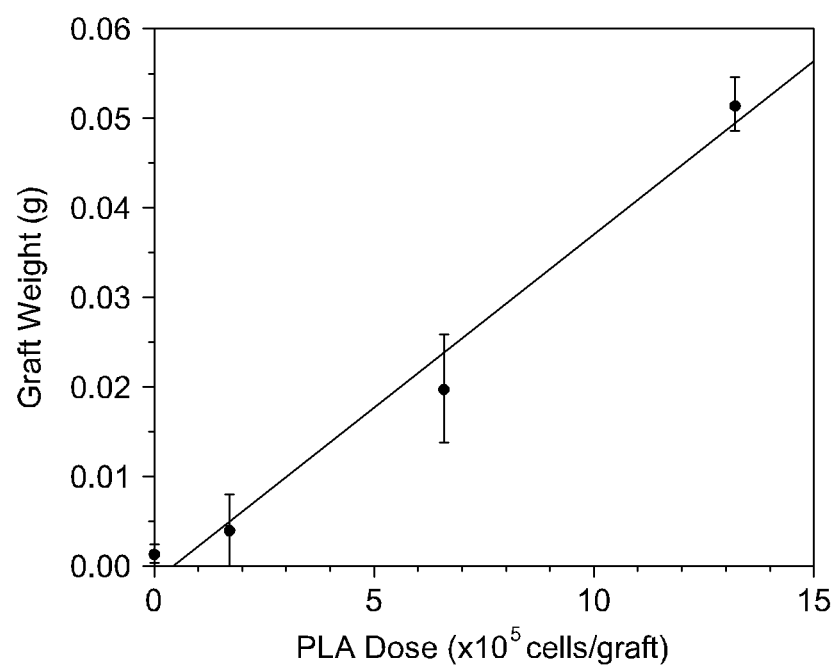
FIGS. 20A and 20B shows that increasing adipose derived stem cell dose improves graft survival and angiogenesis (20A) and depicts the retention of adipose tissue architecture in histologic specimen (20B).
Figure 20B:
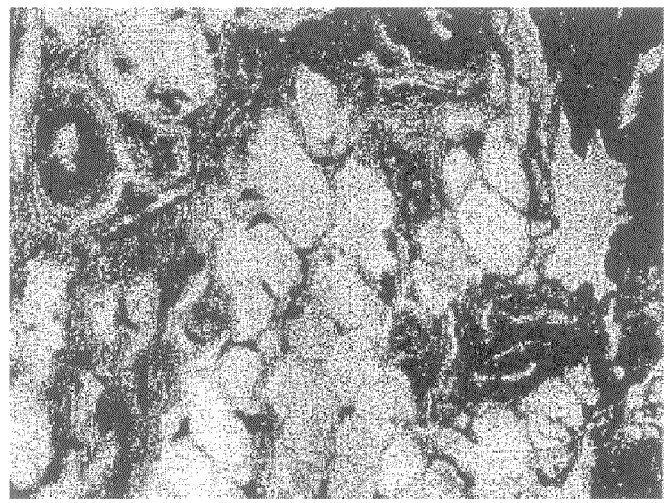

As shown in FIG. 9A, the results show minimal retention of grafted tissue in the control leg and a dose-dependent increase in retention of graft weight in the treated leg. Further, immunohistochemical analysis of the grafts showed considerable neoangiogenesis and perfusion in the adipose derived stem cell treated grafts (FIG. 20B, arrows). This was also associated with retention of adipose tissue morphology (FIG. 20B).

Accordingly, Examples 1-5 demonstrate that the adipose derived regenerative cells of the invention secrete angiogenic and arteriogenic growth factors; form nascent capillary networks in vitro; enhance survival of fat grafts; and enhance ischemic reperfusion. Thus, the regenerative cells of the invention are capable of promoting angiogenesis and arteriogenesis, and may be functional in treating multiple diseases with underlying circulatory insufficiencies.

Example 6

Augmentation of Autologous Fat Transfer by Adipose Derived Regenerative Cells in Mice The potential of adipose derived regenerative cells (ADCs) to augment autologous fat transfer was tested in mice. ADCs were obtained from mice carrying the lacZ transgene (Rosa 26 mice (B6; 129S-Gt(ROSA)26Sor); usually known as Rosa 26 mice). ADCs were admixed with adipose tissue obtained from the inguinal fat pads of histocompatible C57B16/S129F1 mice in accordance with the methods disclosed herein and implanted into subcutaneous space in the back of the skull of additional F1 mice.

After one month, the implants were retrieved and stained overnight in X-gal solution. Cells expressing the lacZ transgene (ADCs) will stain blue on exposure to X-gal. The implant showed blue staining throughout the tissue. The implant was then embedded in paraffin, sectioned, and stained with an antibody to the receptor for mouse Vascular Endothelial Growth factor 1 (VEGFR1).

Figure 19:
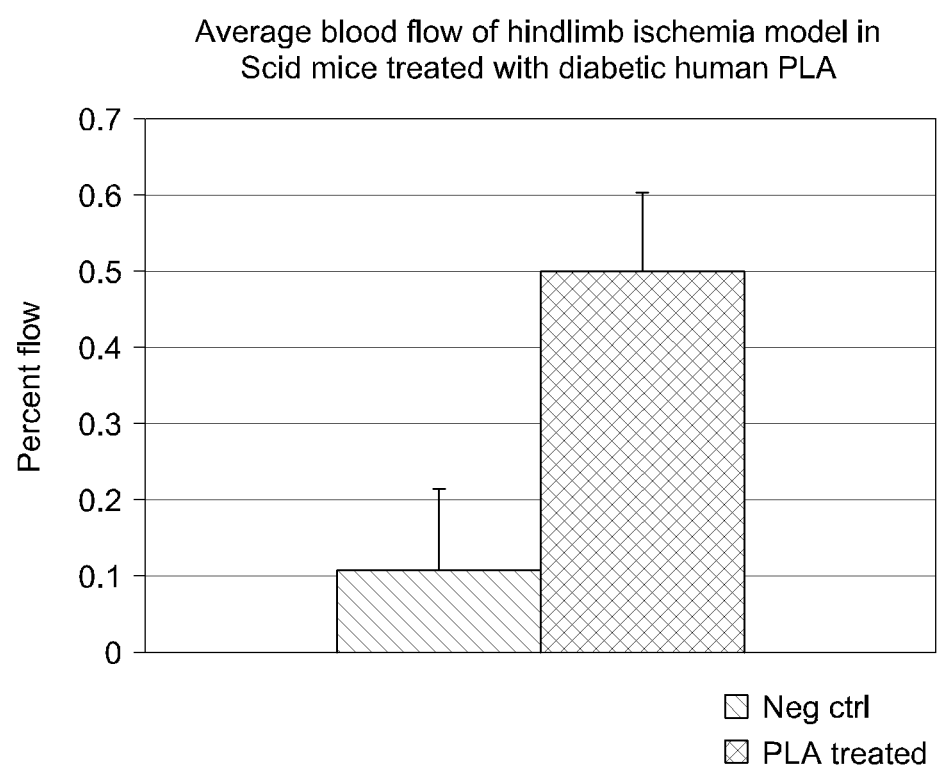
FIG. 19 depicts the increased average restoration of blood flow in hindlimb ischemia mice treated with adipose derived stem cell compared to a negative control.

FIG. 19 shows the results of staining in which the implant was shown to contain numerous circular structures comprised of cells that contained blue granules (arrows) and which were also VEGFR1-positive (dark coloration over cell cytoplasm). This data confirms the ability of processed lipoaspirate to induce the formation of new blood vessels within the implant.

Example 7

Augmentation of Autologous Fat Transfer by Adipose Derived Regenerative Cells in Rats Extracted adipose tissue fragments from inbred Wistar rats were mixed with adipose derived regenerative cells in accordance with the methods disclosed herein. This composition was then implanted subcutaneously into the thigh and under the scalp of recipient rats. As controls an equal number of animals received adipose tissue alone (no ADCs) under the scalp while animals receiving an implant in the thigh had the contralateral thigh implanted with adipose tissue alone. Grafts were harvested one month post-implantation.

The results (FIG. 20) show a trend of increasing graft weight of thigh implants with increasing dose of adipose derived regenerative cells. Histologic examination of the implants showed improved vascularity of grafts supplemented with ADC. A similar correlation was observed with scalp implants albeit with lower overall retention due to the low vascularity of the dorsal skull in these rats.

Example 8

Autologous Fat Transfer in Breast Augmentation Mammoplasty

A person wishes to have the shape of her breasts altered. Pre-operative evaluation of the patient includes routine history and physical examination in addition to thorough informed consent disclosing all relevant risks and benefits of the procedure.

To begin the procedure, the patient undergoes adipose tissue collection. The patient's habitus is examined for a site suitable for adipose tissue collection. The procedure is performed at the patient's bedside. Adipose tissue is selected to be harvested from the lateral and medial thigh regions of the patient. The area to be harvested is injected subcutaneously with a standard tumescent fluid solution, which may or may not contain a combination of lidocaine, saline, and/or epinephrine in different standardized dosing regimens.

Using an 11-blade scalpel (or other standard blade), a small puncture wound is made in order to transverse the dermis. The blade is turned 360 degrees to complete the wound. A blunt tip 14-guage (or appropriately sized) cannula is then inserted into the subcutaneous adipose tissue plane. The cannula may be connected to a power assisted suction device or to a syringe for manual aspiration. The cannula is then moved throughout the plane to disrupt the connective tissue architecture. The volume of aspirate obtained is between 700 cc and 1000 cc. A fraction of adipose tissue collected in this manner is processed for isolation and concentration of adipose tissue-derived regenerative cells using the methods described above. The remainder of the adipose tissue is processed for re-implantation into the breast. Alternatively, the patient may have adipose tissue removed through a lipectomy procedure.

After removal of adipose tissue, hemostasis of the patient is achieved with standard surgical techniques and the wound closed primarily. The collection of adipose tissue occurs about 1-2 hours prior to augmentation mammoplasty in a clinical office. However, the timing of collection is expected to vary and will depend on quality care standards. Ultimately, the practitioner responsible for administering care to the patient will determine the timing of collection.

The regenerative cells obtained from the adipose tissue processing are mixed with a unit of adipose tissue (approximately 100-300 cc) to be transplanted in the ratio described above. After tissue processing is complete, the patient is prepared to undergo augmentation mammoplasty. The cell dose delivered to the patient is determined from the cell yield after adipose tissue processing. Approximately $5.5 \times 10^5$ cells per 50 cc of autologous fat is transplanted into the breast. The composition is delivered through a standard 14-guage blunt tip cannula inserted into the breast tissue through a periareolar incision. The regenerative cell enhanced adipose tissue is administered in a tear like fashion to increase the surface area to volume ratio.

The patient is monitored, and approximately 7 days after the procedure, the transplant appears to have been successfully engrafted with the effects of the cellular therapy becoming apparent to the attending physician.

Example 9

Autologous Fat Transfer and Soft Tissue Defects

A patient presents a desire for soft tissue augmentation, in particular, treatment of dermal divots. A physician evaluates the patient by conducting a history and physical evaluation and determines that the patient is a candidate for autologous fat transfer.

To begin the procedure, the patient undergoes adipose tissue collection. The patient's habitus is examined for a site suitable for adipose tissue collection. The procedure may be performed at the patient's bedside. Adipose tissue is harvested from the patient's anterior abdominal wall pannus. The area to be harvested is injected subcutaneously with a standard tumescent fluid solution, which may or may not contain a combination of lidocaine, saline, and/or epinephrine in different standardized dosing regimens.

Using an 11-blade scalpel (or other standard blade), a small puncture wound is made in order to transverse the dermis. The blade is turned 360 degrees to complete the wound. A blunt tip 14-guage (or appropriately sized) cannula is then inserted into the subcutaneous adipose tissue plane. The cannula may be connected to a power assisted suction device or to a syringe for manual aspiration. The cannula is then moved throughout the plane to disrupt the connective tissue architecture. The volume of aspirate obtained ranges from about 400 cc to about 800 cc. A fraction of adipose tissue collected in this manner is processed for isolation and concentration of cells using the methods disclosed above. The remainder is processed for re-implantation into the soft tissue.

After removal of adipose tissue, hemostasis of the patient is achieved with standard surgical techniques and the wound closed primarily. The collection may take place 1-2 hours prior to soft tissue augmentation.

Regenerative cells obtained from the adipose tissue processing are mixed with a unit of adipose tissue to be transplanted in a manner and ratio as described above. After tissue processing is complete, the patient is prepared to undergo soft-tissue augmentation. The cell dose delivered to the patient is determined from the cell yield after adipose tissue processing. Approximately $5.5 \times 10^5$ per 50 cc of autologous fat is transplanted into the soft tissue. The composition is delivered through a standard 14-guage blunt tip cannula inserted into the soft tissue through an appropriately placed incision. The regenerative cell enhanced adipose tissue is preferably administered in a tear like fashion to increase the surface area to volume ratio.

The patient is monitored prior to, during, and after the delivery of transplanted adipose tissue. After 2 days, the patient notices an almost complete elimination of the dermal divots.

Example 10

Autologous Fat Transfer for Stress Urinary Incontinence

A person experiencing urinary incontinence requests treatment from a physician. Pre-operative evaluation of the patient includes routine history and physical examination in addition to thorough informed consent disclosing all relevant risks and benefits of the procedure.

To begin the procedure, the patient undergoes adipose tissue collection. The patient's habitus is examined for a site suitable for adipose tissue collection. The procedure may be performed in an operating suite with hemodynamic monitoring appropriate to the patient's clinical status. Adipose tissue is harvested from the patient's lateral and medial thigh regions of bilateral lower extremities, and anterior abdominal wall pannus. The area to be harvested is injected subcutaneously with a standard tumescent fluid solution, which may or may not contain a combination of lidocaine, saline, and/or epinephrine in different standardized dosing regimens.

Using an 11-blade scalpel (or other standard blade), a small puncture wound is made in order to transverse the dermis. The blade is turned 360 degrees to complete the wound. A blunt tip 14-guage (or appropriately sized) cannula is then inserted into the subcutaneous adipose tissue plane. The cannula may be connected to a power assisted suction device or to a syringe for manual aspiration. The cannula is then moved throughout the plane to disrupt the connective tissue architecture. The volume of aspirate obtained is about 1200 cc. A fraction of adipose tissue collected in this manner is processed for isolation and concentration of regenerative cells using the methods described above. The remainder of the adipose tissue is processed for re-implantation in proximity of the patient's bladder neck and proximal urethra. Alternatively, the patient may have adipose removed through a lipectomy procedure. After removal of adipose tissue, hemostasis is achieved with standard surgical techniques and the wound closed primarily. The collection of adipose tissue occurs about 1-2 hours prior to the procedure.

The regenerative cells obtained from the adipose tissue processing are mixed with a unit of adipose tissue to be transplanted in the ratio described above. After tissue processing is complete, the patient is prepared to undergo transplantation. The cell dose delivered to the patient is determined inter alia from the cell yield after adipose tissue processing. Approximately $5.5 \times 10^5$ cells per 50 cc of autologous fat is transplanted in proximity of the patient's bladder neck and proximal urethra through cystoscopic visualization.

The patient is monitored after the procedure. Approximately three days after the transplant, the patient experiences a decreased frequency of incontinence. Approximately one month after the procedure, the patient indicates that his quality of life has improved. The physician evaluates the engrafted tissue and determines that the long-term engraftment was successful.

A number of publications and patents have been cited hereinabove. Each of the cited publications and patents are hereby incorporated by reference in their entireties.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:
1. A method of augmenting autologous fat transfer to a subject, comprising:
removing a first portion of adipose tissue that comprises a cell population comprising adipose-derived stem cells and progenitor from said subject;

introducing the removed adipose tissue into a self-contained cell processing unit configured to maintain a closed pathway;

isolating said cell population that comprises adipose-derived stem cells and progenitor cells from mature adipocytes and connective tissue present in the removed adipose tissue so as to obtain a substantially isolated cell population comprising disaggregated adipose-derived stem cells and progenitor cells, while maintaining a closed pathway;

concentrating said substantially isolated cell population comprising disaggregated adipose-derived stem cells so as to obtain a concentrated cell population that comprises disaggregated adipose-derived stem cells and progenitor cells, while maintaining a closed pathway;

mixing said concentrated cell population comprising adipose-derived stem cells and progenitor cells with a second portion of unprocessed adipose tissue comprising intact, non-disaggregated tissue fragments obtained from said subject, so as to obtain an adipose tissue composition comprising a mixture of said concentrated cell population comprising disaggregated adipose-derived stem cells and progenitor cells and said unprocessed adipose tissue comprising intact, non-disaggregated tissue fragments tissue; and reintroducing said adipose tissue composition into said subject.

2. The method of claim 1, further comprising providing said mixture of the unprocessed adipose-tissue and the concentrated cell population that comprises adipose-derived stem cells and progenitor cells to a breast of the subject.

3. The method of claim 1, wherein said subject has radiation trauma.

4. The method of claim 1, further comprising providing said mixture of the unprocessed adipose-tissue and the concentrated cell population that comprises adipose-derived stem cells and progenitor cells to a soft-tissue region of the subject.

5. The method of claim 4, wherein said soft tissue defect was from irradiation or war injury.

6. The method of claim 1, further comprising providing said mixture of the unprocessed adipose-tissue and the concentrated cell population that comprises adipose-derived stem cells and progenitor cells to a urethral region of the subject.

7. The method of claim 1, wherein multiple doses of the mixture of the unprocessed adipose-tissue and the concentrated cell population that comprises adipose-derived stem cells and progenitor cells are provided to said subject.

8. The method of claim 1, further comprising providing one or more angiogenic factors to the mixture of the unprocessed adipose-tissue and the concentrated cell population that comprises adipose-derived stem cells and progenitor cells.

9. The method of claim 1, further comprising providing the one or more arteriogenic factors to the mixture of the unprocessed adipose-tissue and the concentrated cell population that comprises adipose-derived stem cells and progenitor cells.

10. The method of claim 1, further comprising providing one or more immunosuppressive drugs to the mixture of the unprocessed adipose-tissue and the concentrated cell population that comprises adipose-derived stem cells and progenitor cells.

11. The method of claim 1, further comprising culturing said concentrated cell population that comprises adipose-derived stem cells and progenitor cells prior to mixing said cell population that comprises adipose-derived stem cells with said second portion of unprocessed adipose tissue comprising intact, non disaggregated tissue fragments from said subject.

12. The method of claim 11 wherein said culturing step comprises exposing said concentrated cell population that comprises adipose-derived stem cells and progenitor cells to culture conditions that promote differentiation towards an endothelial phenotype.

13. The method of claim 11, wherein said culturing step is performed on a scaffold.

14. The method of claim 13, wherein said scaffold is resorbable in vivo.

* * * * *